US012766325B2

(12) United States Patent
John et al.

(10) Patent No.: US 12,766,325 B2
(45) Date of Patent: Oct. 20, 2026

(54) METHODS FOR TREATING THE SYMPTOMS OF NOCTURIA

(71) Applicant: EBT MEDICAL, INC., Toronto (CA)

(72) Inventors: Michael Sasha John, Larchmont, NY (US); Paul B. Yoo, Toronto (CA)

(73) Assignee: EBT Medical, Inc., Toronto (CA)

( * ) Notice: Subject to any disclaimer, the term of this patent is extended or adjusted under 35 U.S.C. 154(b) by 743 days.

(21) Appl. No.: 17/445,569

(22) Filed: Aug. 20, 2021

(65) Prior Publication Data

US 2021/0379382 A1 Dec. 9, 2021

Related U.S. Application Data

(63) Continuation of application No. 16/025,496, filed on Jul. 2, 2018, now Pat. No. 11,135,428.

(60) Provisional application No. 62/528,103, filed on Jul. 2, 2017.

(51) Int. Cl.

| | |
|---|---|
| ***A61N 1/36*** | (2006.01) |
| ***A61N 1/372*** | (2006.01) |
| *A61N 1/02* | (2006.01) |

(52) U.S. Cl.

CPC ....... *A61N 1/36132* (2013.01); *A61N 1/3603* (2017.08); *A61N 1/36125* (2013.01); *A61N 1/36142* (2013.01); *A61N 1/025* (2013.01); *A61N 1/37223* (2013.01); *A61N 1/37247* (2013.01)

(58) Field of Classification Search

CPC .. A61N 1/3603; A61N 1/3612; A61N 1/3613; A61N 1/3724

See application file for complete search history.

(56) References Cited

U.S. PATENT DOCUMENTS

| | | | | |
|---|---|---|---|---|
| 6,113,539 A * | 9/2000 | Ridenour | A61B 5/68 | 128/903 |
| 2005/0177051 A1* | 8/2005 | Almen | A61B 5/02405 | 600/509 |
| 2008/0300649 A1* | 12/2008 | Gerber | A61B 5/205 | 600/586 |
| 2014/0046423 A1* | 2/2014 | Rajguru | A61N 1/36021 | 607/144 |
| 2017/0036020 A1* | 2/2017 | Harrah | A61N 1/36007 | |

(Continued)

OTHER PUBLICATIONS

Nixon, A., Colman, S., Sabounjian, L., Sandage, B., Schwiderski, U. E., Staskin, D. R. (2005). A Validated Patient Reported Measure of Urinary Urgency Severity in Overactive Bladder for Use in Clinical Trials. The Journal of Urology, 174 (2), 604-607. doi: 10.1097/01.ju.0000165461.38088.7b. (Year: 2005).*

*Primary Examiner* — William J Levicky

(74) *Attorney, Agent, or Firm* — Rosenberg, Klein & Lee

(57) ABSTRACT

Methods for treating nocturia in a person are provided. The methods include assessing and identifying a person suffering from nocturia. A neurostimulator having a processor is connected to an electrical generator. The processor receives sensed data from the person and includes a sleep stimulation protocol. A determination is made as to whether the sensed data in cooperation with the sleep stimulation protocol indicates that a trigger event has occurred which defines a nocturia condition. When a trigger event has been determined, a therapy regimen provides electrical or magnetic stimulation to the leg of the person between the ankle and knee according to the sleep stimulation protocol.

28 Claims, 23 Drawing Sheets

(56) References Cited

U.S. PATENT DOCUMENTS

| | | | | |
|---|---|---|---|---|
| 2017/0361093 | A1* | 12/2017 | Yoo | A61N 1/36007 |
| 2021/0205619 | A1* | 7/2021 | Wong | A61N 1/0456 |

* cited by examiner

METHODS FOR TREATING THE SYMPTOMS OF NOCTURIA

REFERENCE TO RELATED APPLICATIONS

This patent application is a Continuation of U.S. patent application Ser. No. 16/025,496 filed 2 Jul. 2018 and claims the benefit of, and incorporates by reference fully herein, U.S. Provisional Patent Application Ser. No. 62/528,103 filed 2 Jul. 2017.

FIELD OF THE INVENTION

This invention relates to stimulation of peripheral nerves or any anatomic target that is modulated using transcutaneous or percutaneous stimulation, and/or stimulation provided using an implanted device.

BACKGROUND OF THE INVENTION

The invention relates to external and implanted embodiments that provide therapy while also allowing for facilitating user interaction and assessment of user behavior and user needs.

Transcutaneous electrical nerve stimulation (TENS) systems have been used for over 50 years and typically are comprised of an electrical generator, controllers for adjusting the parameters of stimulation, and electrode pads for providing stimulation. Most devices for providing TENS are not configured to provide therapy to a particular body part or target nerve, and are generic for application to many areas of the body. Recently developed wearable TENS systems for pain treatment and muscle stimulation may be configured to provide stimulation to a patient's back or leg. Aside from the prior art filed by the Inventors, there are no wearable TENS systems designed to provide treatment of overactive bladder using the saphenous nerve (SAFN) using methods such as for determining therapeutic intensity that is well chosen, even more so in patients who have difficulty reporting nerve recruitment.

Traditional TENS systems do not provide ecosystems to improve therapeutic benefit derived from providing stimulation in the treatment of a disorder such as overactive bladder (OAB). For example, compliance for treatment with TENS is a problem and the common manner of assessing user compliance is typically a user keeping a written log or the system having a counter that indicates how many treatments, or total treatment time has been provided by a user. The incorporation of features that can both track and promote compliance of a treatment schedule and other user behavior would greatly assist in providing better therapy.

A user may incorrectly use a TENS system at home by applying the electrodes incorrectly, using ineffective stimulation protocols, using "stale" electrodes that do not work as intended to provide robust stimulation to a user. Ecosystem support that assists in ensuring that therapy occurs correctly would be improve therapeutic benefit derived by users of the system.

Ecosystem support would also benefit certain types of implantable devices that provide stimulation to target tissue. Users who self-treat at home may experience a number of disadvantages when using neurostimulators that require user cooperation to provide therapy, or which may interfere with a user's daily or nightly activities if therapy is provided (when not desired) automatically according to a schedule or prompted by sensed data.

SUMMARY OF THE INVENTION

When stimulation is applied to a peripheral target such as the saphenous nerve (SAFN), tibial nerve, the posterior tibial nerve (PTN) or other peripheral nerves in regular, pre-selected dates and times as part of the therapy protocol, the stimulation may be inconvenient, and the onset surprising or dangerous. If a stimulation protocol is operating in a cycling ON-OFF schedule with long OFF periods, similar disadvantages may decrease user satisfaction. These issues are encountered regardless of whether stimulation is provided by an external, internal, or hybrid system (having both internal and external system components that are commonly used together). For example, tibial nerve stimulation may cause activation of muscles in the foot. Starting stimulation as a person is engaged in an activity such as driving a car may lead to trouble in accurate control of the gas or break pedal. Additionally, changes in the stimulation evoked sensation or pain threshold, due to electrode migration, body position, or other factors, may cause unexpected discomfort or pain when a stimulation session begins. Providing a user with advanced notification prior to starting a period of stimulation treatment is an object of the invention.

A wearable stimulator device may be worn for extended periods. If used at night, users may forget to remove it and leave it on for several hours after waking up. Additionally, users may decide to provide stimulation that exceeds a recommended duration or dose (duration×amplitude) when seeking greater symptom relief. Patient non-compliance may occur for treatment of OAB, pain, migraine, weight loss, or other symptom or condition that the modulation is intended to address. Additionally, skin located under gel electrodes should be allowed to be exposed to open air to maintain healthy skin. When electrodes or electrode gel remains in contact with an area of skin for an extended period this may cause skin irritation, inflammation, or other unwanted reaction (sores or abscess). This may be an increased risk in elderly users. Systems and methods for monitoring and regulating the time spent using and wearing a stimulator are disclosed.

BRIEF DESCRIPTION OF THE DRAWINGS

These and other objects and features of the present invention will now be more fully disclosed or rendered obvious by the following claims and detailed description of the preferred embodiments of the invention which are to be considered together with the accompanying drawings wherein like numbers refer to like parts, and further wherein:

DETAILED DESCRIPTION

The following description of exemplary embodiments is not considered limiting and modifications to the following is within the scope of the claims. The use of numbers and ranges, unless expressly indicated otherwise are approximations. Slight variations beyond the ranges may achieve the same results. As used herein "a" and "an" refer to one or more. Like numbers in the figures may connote similarity such as 24*a* and 24*b*. The ranges provided herein, such as pulse frequencies, may be based on either healthy humans or humans suffering from various disorders or animal models of pathology. Stimulation parameters derived from animal models or computer simulations are considered to relevant to treatment of humans. The stimulators such as electrode pads or implantable electrode contacts may be positioned or configured/adapted for placement on skin superficial to (overlaying) a target nerve, implanted near a nerve, percutaneously accessed or otherwise configured to stimulate the target. When referring to the position of an electrode proximate/rostral means closer to the head and distal is closest to the toe. In the figures, dashed lines may be drawn along conduits that communicate signals from system modules to sensors or electrodes, but connections between system modules are not shown to avoid cluttering of the figures. The modules described denote functionality and may be realized using portions of a number of other modules of the system. Further, modules may be realized distributed across external stimulators, user devices, implanted devices, and other system components.

Figure 1:
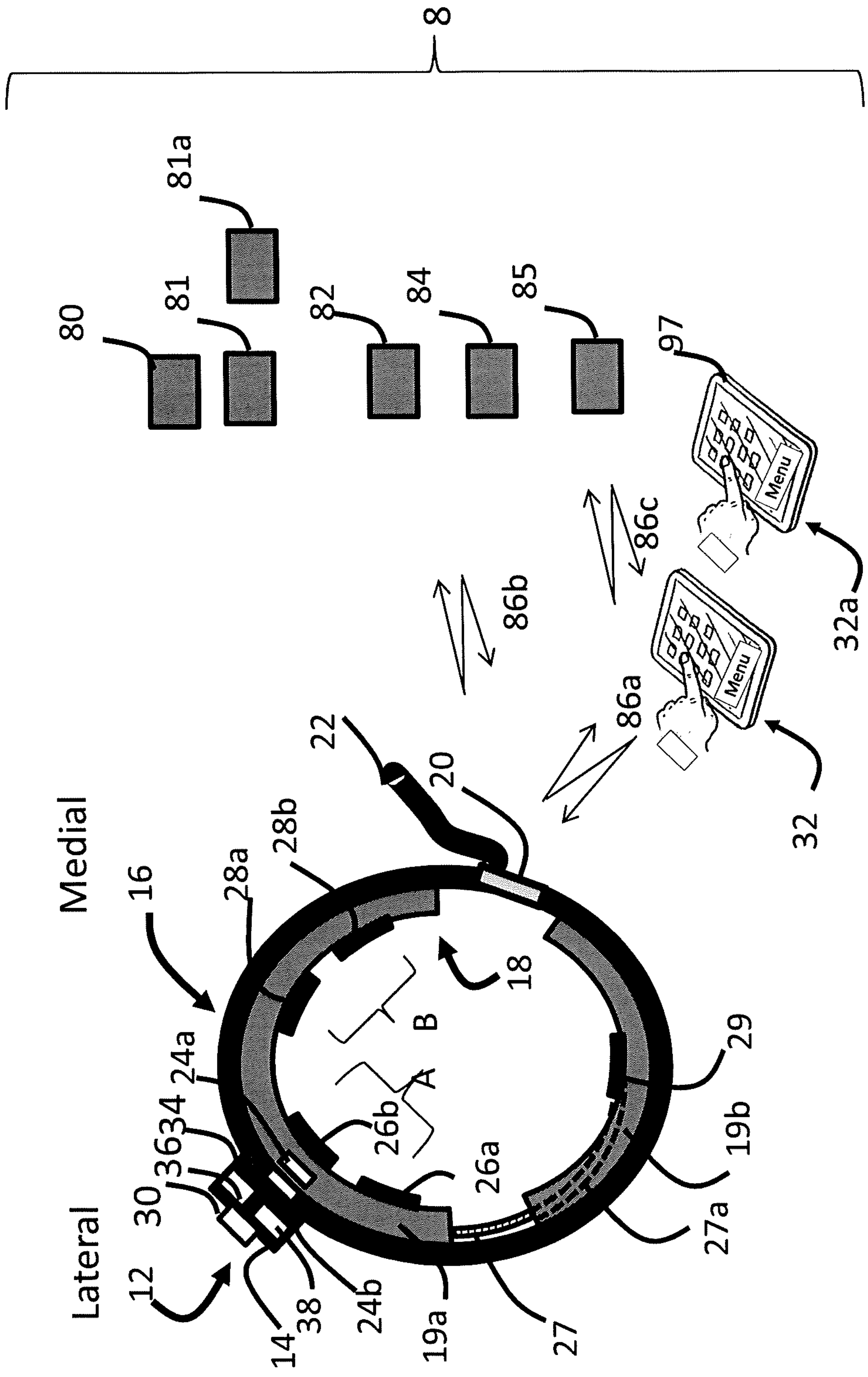
FIG. 1 is a schematic view showing a system including a wearable stimulator, two user devices, accessories and computers which provide an ecosystem of features to assist with therapy.

FIG. 1 shows a system 8 implemented as a wearable system with four components including a TENS therapy device 12, a band 16, an electrode array 18 having at least 2 electrode contacts, and a user/patient device 32. The terms electrode contacts, electrode pads, or stimulation pads all indicate a conductive surface that provides electricity to a user's skin.

The therapy device 12 is realized within in a single housing 14 (as shown) or distributed into electrically connected components each housed independently (and flexibly connected) which provide the hardware, electronics, software, and power used by the device 12. The stimulation system 8 and its components are realized to allow the system 8 to conform to a portion of the anatomy of a user such as their leg 10 (seen in FIG. 14B), and areas near the knee, upper calf, lower calf, and/or area at or above the ankle. The system can be designed to provide peripheral nerve stimulation for various therapies and other uses. The system can also be configured to provide stimulation to an individual's arm, wrist, foot, back, or other portions of the body. In embodiments, the system and its electrodes may be configured to provide stimulation to the head.

Figure 2:
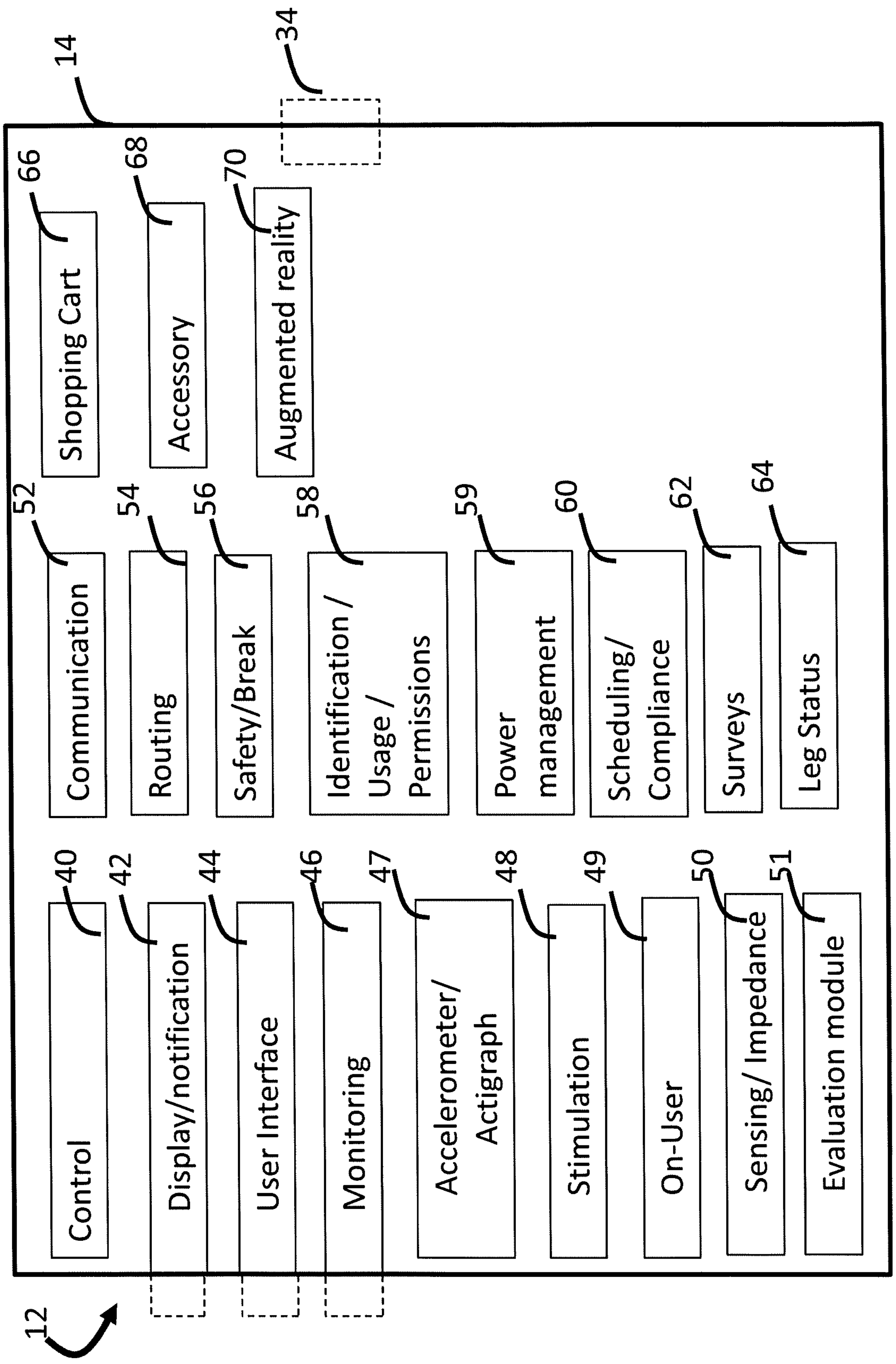
FIG. 2 is a schematic view showing example modules of a device that provides stimulation.

The device 12 contains at least one stimulus generator and circuitry (e.g., D/A, routing, multiplexing, and amplification hardware) for providing stimulation signals via its stimulation module 48 and routing module 54 (see FIG. 2). Controls 30 and hardware that serve as a user interface and are provided as part of a user interface module 44 that allows a user to control device operation. The circumference of the band 16 is adjustable to the user's limb and may include a securing element 20 such as a buckle or Velcro™ fastener that allows the circumference of the band 16 to be tightened by pulling on the tip 22 of the band.

The electrode array 18 comprises a set of at least one or more electrical pads having a first connector port 24*a* that is configured to be reversibly coupled with (e.g., "snapped onto") a second connector port 24*b* provided on the housing 14 of the device 12 to electrically communicate signals between the device 12 and the array 18 and to mechanically and electrically connect these two components of the wearable system 8. Wet or dry electrode pads 26*a*, 26*b* may be used having flat or textured surfaces.

When the system 8 is realized in a distributed manner then the connector ports, 24*a*, 24*b* can be connected by a conduit having at least two electrical paths provided therein. In embodiments, connection ports 24*a*, 24*b* have multiple contacts that allow routing to individual electrode contacts. Dynamic routing is provided by routing circuitry and/or electrical switch circuitry under control of the therapy device 12 or a user device 32. The control module 40 of the device 12 or user device 32 communicates with other components of the system, in a wired or wireless manner, to route stimulation signals to selected electrode contacts 26*a*/26*b*, 28*a*/28*b*, and 29 of the system according to a stimulation protocol. When two users cooperate to set or adjust treatment parameters, a first user (e.g. the patient) may operate a first user device 32 while a second user (e.g., doctor) operates a second user device 32*a*. Direct electromechanical connection between the device 12 and one or more of the electrode pads 26*a* can eliminate, or reduce the number of, conventional lead wires that are often used by many conventional TENS system designs. In addition to a direct electromechanical connection, or an electrode array, some embodiments disclosed herein use one or more conventional lead wires to communicate stimulation signals from the device 12 to more distally located electrode pads.

The device 12 can provide power, data, and communication connectivity with other devices using a communication port 34 (e.g. a USB port). In an embodiment, the port 34 allows for data upload (e.g., stimulation protocol values) or download (e.g., a record of stimulation use data to assess compliance). For example, a user can select a stimulation protocol on a user device 32 such as a laptop and then connect a cable to the port 34 to upload the protocol to the device 12. The therapy device 12 may be configured to not allow stimulation if the port 34 is connected: it may be configured to "break" a circuit that normally communicates signals between the array connection port 24*b* and the electrical waveform generator of the stimulation module. Systems and methods for providing patient safety are well known in the art.

The device 12 can utilize a first pair of electrode contacts 26*a*, 26*b* ("labeled A" in the figure) configured and positioned to stimulate a first anatomical region. For example, electrode contacts 26*a*, 26*b* can provide stimulation to the lateral side of the leg (e.g. upper shin area) over a portion of the sural nerve to stimulate the patient in the treatment of pain. A second pair of electrodes 28*a*, 28*b* can be used to provide stimulation of the saphenous nerve (SAFN) on the medial aspect of the leg (labeled "B"). Additionally, at least one electrode pair can be positioned vertically rather than horizontally. The provision of a first and second pair of electrodes, operated in accordance with selectable stimulation protocols, can allow for the same device to provide selective treatment for different disorders such as pain, overactive bladder, or both.

Vertical orientation may provide an advantage of allowing for a greater recruitment of SAFN fibers. For example, vertically oriented electrodes may be spaced further apart which can cause the electrical path to pass deeper with the tissue. The distance between the two electrodes may be made larger to provide for improved recruitment of the SAFN fibers. For example, the vertical distance between the closest edges of the electrode pads may be increased from approximately 1 mm or 1 inch, to 2 to 5 inches to increase the depth and area of the stimulus field.

In an alternative embodiment, another electrode pad 29 or "contact" may also be provided upon a second segment 19*b* of an electrode array. The second segment may be electrically connected to the first segment 19*a* by a conduit 27 (such as a multi-stranded wire) which runs from the port 24*a* to each of the electrodes of the array 18. A portion 27*a* of conduit 27 that resides within, or is attached to, the electrode array 18, is shown as a dashed line in the figure. Although array 18 is illustrated as relatively thick compared to the band, it may be realized as a thin rectangular pad, with electrode contacts positioned on its surface. In an embodiment the array 18 is formed upon a pad that has foam backing to increase patient comfort.

The device system is configured to communicate signals 86*a* between the device 12 and a user device 32, signals 86*b* between a device 12 and an accessory 81 or remote computer (e.g. remote computer 82 at a clinic), or signals 86*c* between a user device 32 and a remote computer (e.g. computer 84 e-commerce), or between two user devices 32 and 32*a*.

When the system 8 contains two or more stimulation devices 12, to coordinate joint operation, one device may be designated the "master" and the other the "slave", or both may be under control of a user device 32. The user device 32, may be implemented into a smartphone or may be implemented as a specialized remote-control device with dedicated displays, subroutines, and controls. A simpler user device is helpful when used in a clinical environment or by a non-technically oriented user.

In an embodiment, the system 8 operates with accessories that improve the user experience, by facilitating or automating the monitoring of user behavior, symptoms, and therapy benefit. For example, an accessory 81 may include a device or sensor that senses moisture and provides the system with an automated means to obtain and log quantitative (small or medium leak) or qualitative (wet dry) data related to incontinence (such as bedwetting). An example accessory 81 is a moisture detection and notification system which is worn in a user's undergarment or located on a bed (e.g., Rodger Wireless Bedwetting Alarm System®, Sensassure™ Talli system, with all components incorporated by reference herein). Sensed data including moisture detection and time is obtained and operated upon (or stored) by the sensing module 50 of the system 12, and the accessory module 68 permits identification of the accessory 81, so that suitable communication protocols are provided by the communication module 52. When configured for notification, the accessory 81 operates its own notification circuitry and transducers to issue an alarm signal upon detection of moisture or communicates this signal 86*b* to the external user device 32. The system 8, the device 12, or a separate alerting device is configured to receive the alarm signal and provide a notification signal according to a protocol. For example, a notification signal sent by the system 8 due to analysis of a signal containing data sent by the accessory causes a second accessory 81*a* such as a smart-watch on a user's arm to vibrate. The system 8 may also present a sonic or vibration alarm using an accessory 81*a* that awakens a child who suffers from bedwetting. Additionally, a moisture sensor can be provided on the housing 14 of the device 12 as part of the monitoring module 46 to detect the presence of moisture. Such detection can halt stimulation to prevent shorting between system components such as electrode pads, or cause other adjustment of the stimulation protocol.

In embodiments, an accessory 81 is a device that "pings" the stimulation device 12, to test the "reachability" of the device 12. Events such as bathroom visits can be automatically logged or acted upon by the accessory module 68 when the user device is in range of the "ping" signal. Such location detection capability is well-known in internet of things (TOT) technology and protocols (e.g. for identification, security, handshaking, etc.) available for achieving presence or proximity detection between two objects, and is part of the disclosed invention as part of the communication module 52. The communication module 52 of system 8 is designed to detect/communicate with multiple accessory devices that "ping" which are identified by the accessory module 68.

In an embodiment, the system provides for both user customization and physician customization of individual patient stimulation and monitoring. When this occurs remotely, functionality is provided by the relevant modules of the device shown in FIG. 2 being operated in a remote computer 82 at a clinic. The remote computer 82 allows the doctor to select what information for one or more patients should be displayed using a software program running on the remote computer 82 (check boxes on a list related to display options). The remote computer 82 may also allow the doctor to use a mobile app on a doctor oriented user device 32*a* which is a smartphone or tablet, or may communicate with the device 12 by making changes on a website hosted by a remote server computer 85 that provides ecosystem features such as clinical services related to using the wearable stimulator. Display options include, for example, which data to present as trend graphs or summary statistics (e.g., for symptom severity and frequency), graphs of stimulation compliance/usage, and/or medication compliance, and setting related to stimulation schedule, stimulation parameters, and the setting of reminder alarms.

In an embodiment, the system 8 is integrated to work with a larger e-health system that the remote computer 82 used by a clinic has access. For example, the physician can operate the remote computer 82 to import, process and operate upon demographic and medical information of electronic patient medical records or services and populate data in the device 12. The patient-specific information can be used to adjust patient therapy treatment parameters. For example, various user characteristics—DAB drug history, record of surgical procedures, symptoms (urge vs incontinence), length and severity of disorder, age, other conditions, age, race, gender, etc is used to set and subsequently adjust treatment protocol parameters.

The remote computer 82, may be realized using a cloud-based computer system. When data from multiple users, clinics, or physicians are stored and operated upon using the "cloud", patient data, including the device 12 ID, is assigned an anonymous patient ID which is stored on the user/physician device. The user (or physician) can view a particular patient (or set of patients) data stored in the cloud. When presented graphically, an individual patient's data can be plotted in a unique color to allow a user to see how their data relates to the larger population being tracked by the cloud.

The system 8 provides non-transitory computer-readable medium in the control modules 40 of the device 12, user device 32, and other system components that is configured for storing one or more instructions configured to be executed as part of system operation by at least one processor of the system. The processor can be at least one processor of control module of a stimulation device 12, an implantable neurostimulator 600 (See FIG. 20), a user device 32, or remote computers 80, 82, 84, 85 that communicate over the internet to cause the system to operate in a particular manner. It is understood that in different embodiments, selected system components are configured to provide the stimulation or participate in the stimulation include related hardware such as a stimulus generator, isolation circuitry, microprocessors, memory (e.g., RAM, ROM. Flash memory, etc.), connectors, signal routing, batteries, power transformers, amplifiers, and hardware for providing communication and accepting user input. The components run upon software instructions and can operate using, for example and without limitation: firmware, operating systems, utilities, processes, algorithms, and methods/routines that allow the system to function. In an embodiment, when the instructions are executed by a processor of the stimulation device, the device executes a plurality steps comprising delivery of at least a first electrical stimulation signal generated by the signal generator to electrically stimulate the nerve target. The electric field transmitted to the target is generated between at least a first and second electrode that form a circuit to provide at least a first electrical stimulation signal.

FIG. 2 shows an embodiment of the wearable therapy device 12 which contains modules that provide for features of system 8. Modules include any software, hardware, and circuitry that may be needed to achieve functionality of the modules. Modules 42, 44, and 46 are shown as partially dashed lines that extend outside of the housing 14 to indicate that some components of the module (e.g., buttons, displays, transducer, speaker, etc.) extend from inside to outside of the housing, or can reside on the housing and connect to circuitry inside the housing.

The device 12 includes power module 59 having a power source. The module may use a rechargeable battery and/or wireless energy harvesting circuitry.

In an embodiment, the user interface 44 elements (e.g., push button and LEDs) are physically located on device 12 housing. In alternative preferred embodiments, one or more of the user interface elements are realized on a separate user device. The separate/remote user interface elements may communicate with the device 12 through a variety of means including a physical link such as a wire, a wireless link such as a WIFI or Bluetooth connection, an optical or sonic communication, etc. The user interface elements may be remotely located on dedicated user devices 32 specifically designed to control device 12 such as a custom remote control, or may be incorporated into generic devices used by the patient such as a smart phone or tablet computer.

FIG. 2. Shows modules of the system that allow system operation. The individual modules are provided with all the hardware, software program instructions, algorithms, circuitry and power that are required to provide the functionality as disclosed herein. Modules may share resources of other modules. For example, both the display/notification module 42 and the communication module 52 may perform hardware and software operations related to sending a wireless notification signal. A control module 40 controls the other modules of the device 12, and controls the provision of therapy according to parameter settings of a therapy protocol. The control module contains the circuitry needed to control the other modules including at least one processor, readable and writeable memory, timers, clocks, signal processing circuitry, and all circuitry that is typically included in a device such as smartphone. The circuitry of a smartphone may serve as the control module if the device 12 is configured to be attached to, and controlled by, smartphone (or smartwatch or other wearable tech) which interfaces with the device 12 to control the remaining modules and hardware of the device 12. The display/notification module 42 includes displays (e.g., LCD or LEDs, touchscreen) and associated circuitry for presenting text, image information, notification signals, and a graphical user interface for obtaining user input. Notification signals can be presented using other sensory modalities such as sonically (using speaker 94, and a microphone 93 allows processing of voice commands by the user interface module 44, both shown in FIG. 5) for example, tone signals or recorded voice messages, by vibration (e.g., using a motor of the display/notification module 42 that vibrates, or an accessory 81*a* which is a haptic device). Notifications can be multi-modal and presented both by the device 12 and the user device 32. The user interface module 44, provides at least one user control for allowing adjustment of therapy (e.g. turning therapy on/off or increasing/decreasing stimulation intensity). As disclosed, in embodiments, control signals provided by a user in the form of gestures, voice commands, are used to control device operation.

The monitoring module 46, monitors user, device, and sensor information, and user input data. For example, information about the orientation of the device or activity of the patient can be monitored. Impedance data obtained by the sensing/impedance module 50 can be evaluated by the monitoring module 46 and cause the stimulation to stop, or a patient to be issued a notification, if the impedance drops below a minimum defined threshold amount using methods that will be disclosed. Visual data can also be evaluated by the monitoring module 46. For example, the monitoring module 46 cooperates with the display/notification module 42, to realize an augmented reality feature that guides the user by confirming correct electrode location and orientation using routines provided by the augmented reality module 70. For example, a digital camera 97 of the user device 32 is used to view their leg, and an image of the correct area is superimposed upon the leg by algorithms of the augmented reality module 70 so that the user can move the electrode or electrode array to the correct location.

An Accelerometer/Actigraph module 47 provides operations related to sensing and evaluation of data collected from an accelerometer (which is part of the module). In embodiments, the module operates upon accelerometer data to calculate actigraphy data. That data can be combined with other sensed data collected from other sensors and/or time information to assess user status and state. The stimulation module 48 provides stimulation waveforms according to the stimulation protocol of the treatment regimen protocol stored in the memory of the control module 40 and operates with the routing module 54 to provide stimulation signals using at least one pair of electrode pads (or other stimulators) at different moments in time. The stimulus generator, amplification, filtering, and signal conditioning hardware included in this module varies according to the type of stimulation treatment which is provided. An On-User module 49 operates according to On-User protocols and algorithms to provide sensing, analysis, classification, storage, and display of information related to whether the wearable device 12 is being worn. The On-User module 49 also operates to determine when and how the device 12 is being used. On-User module 49 also tracks information related to when the device is not on a user or is incorrectly connected (e.g. variable impedance values indicate improper electrode-skin contact). The on-user module 49 also has rules for providing user notification or user interaction according to the on-user status.

The safety/break module 56 provides operations and routines related to patient safety, such as providing for electrical isolation of the stimulation module 48 from charging circuitry, and batteries (if included) of the power module 59. The power module 59 is controlled by the control module 40 to manage power operations. The control module 40 may assess data about prior stimulation sessions and obtain a measure of power remaining to determine whether there is sufficient power to provide a defined stimulation session or if a user should charge the device 12 prior to providing the therapy session. The communication module 52 operates wired or wireless communication circuitry and protocols to provide communication between different components of the system 8, and between the system 8 and external devices, accessories 81, or remote computers 82 such as computers 82 at a doctor clinic, a computer 85 hosted by a clinical service of the ecosystem, or with computers 84 or local devices that communicate with the computers that provide voice services, distribution or other service such as e-commerce (Alexa™ or Echo™ voice service). The identification/usage/permissions module 58 enables system components to be identified (e.g. the serial number of an electrode array, a user's cellphone), usage measured, and permissions granted or denied. For example, only a doctor may be allowed permission to increase the maximum allowed amplitude of stimulation or the amount of stimulation provided within a specified amount of time. Communication between system components can occur using any suitable wireless protocol including for example, radio frequency, WIFI, IEEE 802.1, Bluetooth, infrared-based, sonic-based etc. Identity verification mechanisms can prevent crosstalk or identification issues such as when two devices are used to communicate with a device as is well known. Unique transmission wavelengths, encryption, ID, handshaking, and time-sharing schemes are well known.

The system operates to provide, assess, detect, and store therapy events. Therapy events are any event related to the provision of therapy, such as, the start and completion of a therapy session, increasing or decreasing the intensity, user input data provided by a user interacting with the system 8 to turn the device on or off, or presenting a survey item to a user according to a schedule. Therapy events are tracked, logged, and counted by the monitoring device 46.

Figure 3:
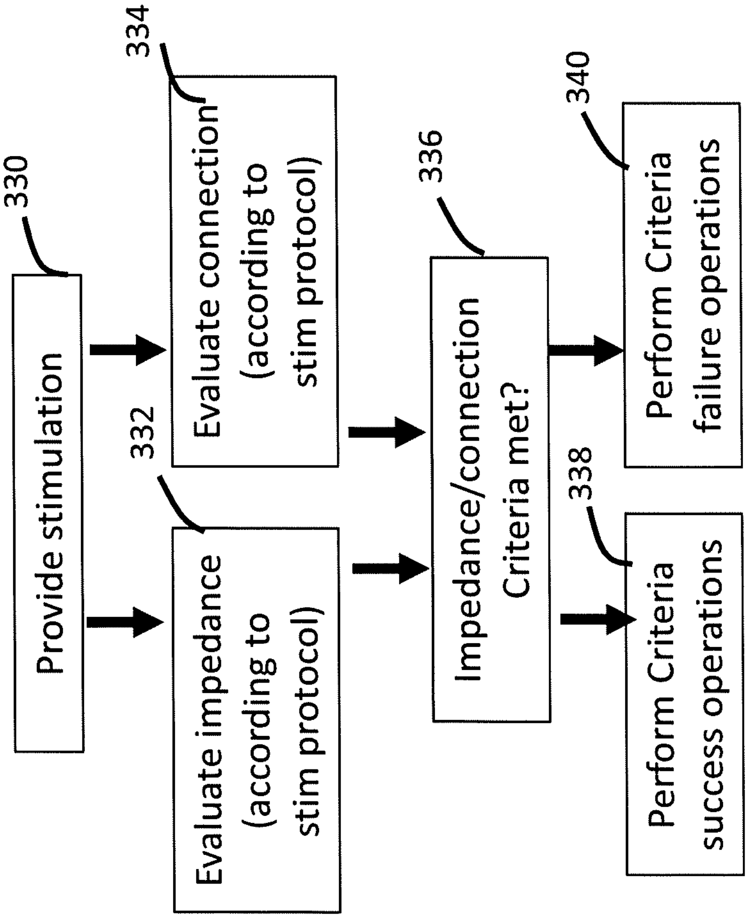
FIG. 3 is an information flow diagram of a method that operates based upon impedance/connection status of the device and/or a band that secures the device to user.

FIG. 3 shows a method for determining if impedance/connection criteria are met. In an embodiment, the device 12 is designed with a monitoring module 46 that causes stimulation treatment 330 be adjusted according to the evaluation of impedance 332 and/or connection status 334. The evaluation of impedance 332 occurs according to an impedance protocol defined for a stimulation protocol. For example, stimulation may be intermittently paused while impedance is assessed (or this can occur continuously while stimulation is provided) to ensure the impedance is within a defined normal operating range for stimulation treatment to be provided as intended. The impedance can be tested at the beginning of each therapy session (rather than after step 330), or can be tested intermittently, such as every minute, or every 5 to 10 minutes, during the provision of therapy. Connection criteria can be assessed 334, for example, pressure sensor 134 (See FIG. 5) data may indicate sufficient pressure exists between the strap 16 and the user's leg 10. If assessment of impedance/connection 336 indicates that the impedance (or connection data) is not above a minimum criterion then criterion failure operations 340 occur, such as the user is alerted. In an embodiment, the history of this assessment is recorded in the memory of the device 12 and if too many impedance values occur above a maximum programmable value across a 2 or 3-day use-period (any day when the device is used), then the failure operations 340 include prompting a user to replace the electrode array. In an embodiment, in steps 332 and 334 the device monitors for decreased or faulty skin-electrode coupling using impedance threshold criteria, or by measuring the current delivered in real-time (i.e. open circuit). In step 340 detection of bad coupling will stop stimulation. Additionally, if the average impedance over the last 10 minutes of therapy exceeds a threshold value calculated upon a previous selected duration or prior number of therapy sessions (e.g. 1 to 5) then in step 340 the user is notified that the array should be replaced. If the average impedance over a selected time interval is above a threshold, or increases by a predetermined percentage relative to session start or when it was first replaced, or if impedance is above an absolute value then, in step 340 the user is notified. Using impedance may not be a suitable indicator of electrode health since electrode conductivity may not well correlated to adhesion. Combining impedance information with information about number of uses or frequency of connection faults may improve accuracy. If the impedance/connection criterion is met then success operations can occur 338 such as continuing stimulation. Impedance/connection criteria can occur as a function of the stimulation protocol that is selected.

The device can operate if assessment of sensed data 336 indicates that an electrode has lost contact or connection to a user is unstable causing impedance/connection criteria to not be met and failure operations to occur 340. For example, decreasing or pausing stimulation, alerting the user or halting stimulation (if the condition is defined as a "break" condition). A sensor 134 such as a silicon piezoresistive pressure sensor, silicon shear stress strain gauge, resistance-type transducer, or other strain-gauge transducer can be used for such a purpose (e.g., MPXx53 Differential/Gauge/Pressure Sensor made by NXP/Freescale) and can be incorporated into a strap, device housing, or electrode array to measure pressure or strain when the system is worn. Accordingly, pressure between the electrode and the user's skin, or the tension of the band that wraps around the user's leg can be measured.

Figure 4:
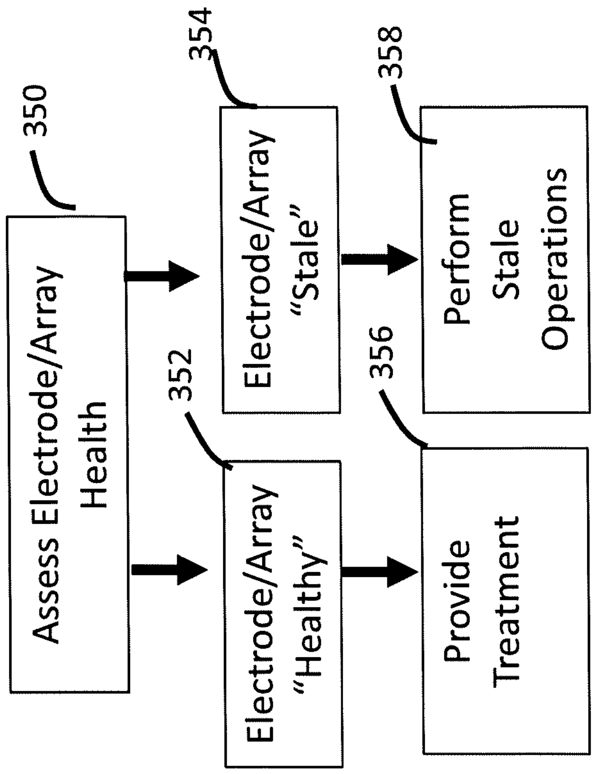
FIG. 4 is an information flow diagram of a method that operates based upon electrode/array "health" status.

FIG. 4 shows a method for assessing electrode health and operating upon the result wherein the first step of assessing health 350 is followed by a status of healthy 352 or stale 354. A healthy status leads to step 356 of providing treatment, while stale leads to performing steps defined for electrode health failure 358. The identification/usage/permissions module 58 can measure usage data to include the amount of time or number of stimulation sessions that an electrode, or an electrode array, has been used. User non-compliance for electrode replacement can decrease adhesion and increase risk of electrical shock, shorting, and device calibration. Decreased patient comfort or efficacy may also result. The monitoring module 46 can assess user data and provide alerts to a user, doctor, or distributor by modules display/notification 42 or communication 52 modules to indicate electrodes replacement is required. An electrode array may contain a memory chip, RFID, or circuitry for providing a unique ID to the device 12 so that the device can measure the duration or number of times that an electrode array has been used. In an embodiment, the system 8 automatically and wirelessly contacts an internet retailer to automatically order and ship replacement electrode pads or prompts a user to do so. In an embodiment, the control module is configured to halt operation of the device 12 if it does not detect, or receive confirmation of, an expected number of purchases within a selected timeframe. The device 12 can operate directly or via software in the user device 32 to allow shopping such as 'one click' purchasing of replacement device parts from within the device 12 "app". Step 350 includes assessing usage data and if the electrode/array health is determined to be stale 354, then performing the stale operations 358 can includes assessing if electrodes have been ordered via the communication module interfacing with a remote computer 82, prompting a user to purchase new electrodes, or deactivating the device 12 from providing further stimulation sessions until an order has been placed.

Figure 5:
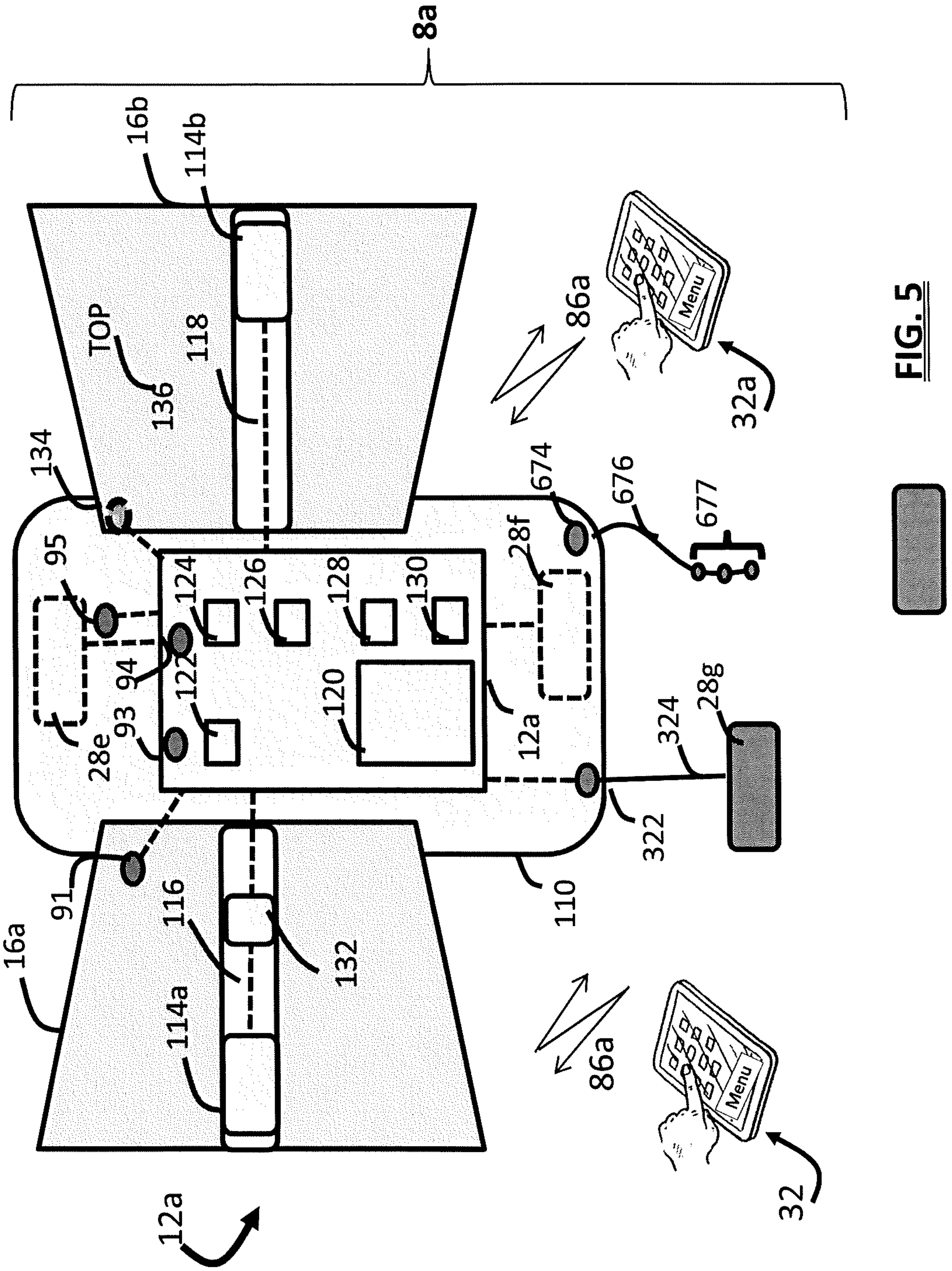
FIG. 5 is a schematic view showing an alternative embodiment of a system including a wearable stimulator, users devices, and various stimulators.

FIG. 5. illustrates an exemplary wearable system that operates with a user device 32 (which may be implemented largely within software of a cellphone or exist as a customized device, or both). When the stimulator device 12*a* operates with the user device 32 then the user device 32 may display virtual controls and display information and communicate using wireless signals 86*a*. In an embodiment, a doctor may use a second user device 32*a*. The device 12*a* is configured to reside on a base member 110 which is physically configured to receive the device 12*a* and make connection between the connector port 24*b* provided on the housing, and the connector port 24*b* provided on the base member 110. The connector port 24*b* in turn communicates electrical signals to electrode pads 28*e*,28*f* located on the bottom side of the base 110, and to conductive strip conduits 116 and 118 which conduct electricity between band connectors 114*a* and 114*b* which make electrical connection when the first strap (band) portion 16*a* is wrapped around a user's leg and connected to the second strap portion 16*b* to close a circuit. When the circuit is closed the device provides therapy since the strap portions are wrapped around the user's leg rather than having come undone. Alternatively, the conduit 118 may provide electricity to a strain gauge sensor 132 that operates with the safety/break module 56 and monitoring module 46 to ensure that the strap has a minimum strain measurement value during stimulation. Alternatively, at least one pressure sensor 134 or 95 is configured (such as between the base section 110 and the band 16*b*, or between an electrode pad 28*c* and the base section 110) to ensure that there is a minimum pressure maintained at the skin-electrode interface during stimulation. LED 91 is enables certain notifications to occur.

The system 8*a* may be configured so that when it is placed upon a leg, the cathode electrode resides more proximally on the leg than the anode electrode pad 28*e*. The consistency of this assignment may be reinforced by position labeling 136 of the device, array, or band. Further, system 8*a* components may be physically shaped to cause the anode or cathode to be the most proximate electrode pad on the leg (or arm in other embodiments). Similarly, if the device is configured to attach to an electrode array it may be shaped to fit so that the electrode selected to serve as the anode or cathode assumes a relative position on a user. At least one electrode can be marked, to enable a user to position that electrode proximally when providing stimulation. The minimum distances between electrodes 28*e*,28*f* may depend upon the application. A preferred embodiment, for stimulating the SAFN, a minimum distance is about 1-2 inches, but this can also be modified depending upon the size of the electrodes. If the cathode and the anode are too close the stimulation current may not travel deeply enough to modulate the target nerve tissue. Making the electrodes smaller can serve to increase the charge density especially near the electrodes, making the maximum output setting level (e.g. current amplitude) which a user may tolerate to be lower than that which would be output by the device if a larger electrode was used. In addition to the size of the surface electrode, the shape and/or configuration of the electrode can be modified to control current density. For example, a plurality of independently controlled concentric rings can be activated.

The system is configured to provide stimulation to the upper calf, and when stimulating the SAFN it may use at least 2 electrodes which are oriented and configured to be separated vertically and typically by at least 1 inch.

To facilitate operation as an independent device, the device 12*a* can have a display 120 which displays information and also virtual controls. Additionally, user controllers located on the device housing may include Button control #1, 122: "on/off/pause"—pressing the button 122 for 3 seconds will turn the unit on or off, pressing button twice (rapidly in succession) will pause/restart the stimulation. In an embodiment, the default stimulation program for treatment of a pelvic floor disorder is defined as: Frequency=20 Hz; Pulse Width=200 ms; Waveform=Asymmetric biphasic; Mode=Constant (stimulation strength does not oscillate); Timer=30 minutes. The device may provide a timed stimulation session where the timer automatically starts counting down when the stimulation intensity is greater than zero, or exceeds a minimum defined amplitude. The timer value can be displayed on the display 120. Upon start of the timed session, the timer can cause a speaker 86 to beep twice and will subsequently beep four times when the session is over.

Button control #2, 124: "intensity increase", will cause the stimulation strength to be increased, via signal amplitude, pulse width or other characteristic of the stimulation waveform. Button #3, 126: "intensity decrease", will cause the stimulation strength to be decreased. Alternatively, Button 124 can be used to either increase or decrease intensity by pressing for at least 1 second, while a short (i.e. less than 0.5 second) will cause the intensity to decrease.

Button control #3—126 "electrode montage". Will cause the electrodes (e.g. electrode 1, 28*e*; electrode 2 28*f*) that are activated to switch combinations such as setting electrode 1 (cathode)-electrode 2 (anode) or electrode 1 (anode)-electrode 2 (cathode). When three or four electrodes are provided (not shown) the montage can alternate between 1-3, 1-4, 2-4, 3-4. If there is an LCD 120 then it can provide an indication of what montage is set. Alternatively, the electrode pads or the housing of the device 12 may have diodes that light up when an electrode is activated. Pressing the button for 5 seconds may cause the device to automatically scroll through different electrode montages until the user pushes the button again to indicate a desired montage is selected.

Button control #4—128 "mode" can cause the device to switch from a default mode to a pre-programmed mode with selected parameter values settings. For example, pre-programmed mode #1 defines a stimulation program that ramps up to a selected intensity and stimulates for 60 minutes.

Button control #5—130 "Multi" can operate various components of the system and is dynamically assigned. For example, if a user wants to use the microphone 93, then they may assign this button as a timed latch control that provides an interval for the user to issue a verbal command. In an embodiment, the device 12*a* is voice controlled. For example, a user depresses button 130 on the device and states "increase 2" to increase the amplitude of the stimulation signal by 2 units.

In an embodiment, the microphone 93 operates as part of the monitoring module 46 to detect night time voiding. If accelerometer data sensed by an accelerometer module 47 during a sleeping protocol indicates either that a user transitions from a sleeping state and is upright (standing, as indicated by leg orientation) or walking, then the device 12 measures sound until analysis of accelerometer data indicates a return to bed (e.g., return to horizontal leg orientation, etc). Sound data is digitized, and processed by the evaluation module 51 such as being band bass filtered, and analyzed to detect the sound of a toilet flushing. For example, an increase in the spectral band associated with the sound of the toilet flushing. Each user may flush their toilet during a calibration period to "train" the device with a spectral template to enable automatic detection of trips to the bathroom.

In an embodiment, stimulation is only provided contingently upon the "closed" status electrical circuit that resides in the band. For example, the device housing has electrical contacts that communicate signals through the base portion 110, to conductive connectors 114*a*, 114*b* of the strap. Each contact is connected to a flexible conductive strip 116 that extends to each end of the band portions 16*a*,16*b*. The two ends of the band are configured so that when wrapped around the user's leg 10 the two end strips make contact and close an electrical circuit. This confirms the band is not unwrapped. Instead of 2 conductive connectors 114*a-b* the band may be designed with a pin and pin-receptacle, respectively, that connect when the band is wrapped: if the circuit is open the device stops providing therapy. Alternatively/additionally, the electrode array or conduits that relay electrical signals to the stimulation pads may have 1 more pressure switches 95 which only close when the pressure on the band is above a certain amount. For example, two deformable contacts may only be pressed together when there is at least a minimum amount of pressure on the pads. When any condition relating to pressure, impedance or tension indicates that the device may have become uncoupled or that there is an increased risk of this, and the sleeping protocol is active, this may serve as a "break" (see 272 of FIG. 13) condition which stops stimulation until it is re-established by a user. These features are important for safety reasons. For example, they deter the band unwrapping during the night, and the electrode array adhering to a user's chest and stimulation continuing.

The nerve stimulator 8*a* may only have one electrode pad 28*e* on its bottom surface. An electrode connector port 322 for connecting to a plug of a conduit 324 that leads to a conventional TENS electrode pad 28*g*. This system design only requires 1 wire rather than 2 used by some conventional TENS stimulators. This allows for greater flexibility than a fixed/rigid electrode array structure. For providing SAFN stimulation, length of the conduit 324 should only be between 1 and 5 inches to avoid unnecessary slack. A connector port 674 can provide stimulation signals to a temporary lead 676 with a distal end having electrode contacts 677 which are temporarily implanted in a user during a screening assessment.

Figure 6A:
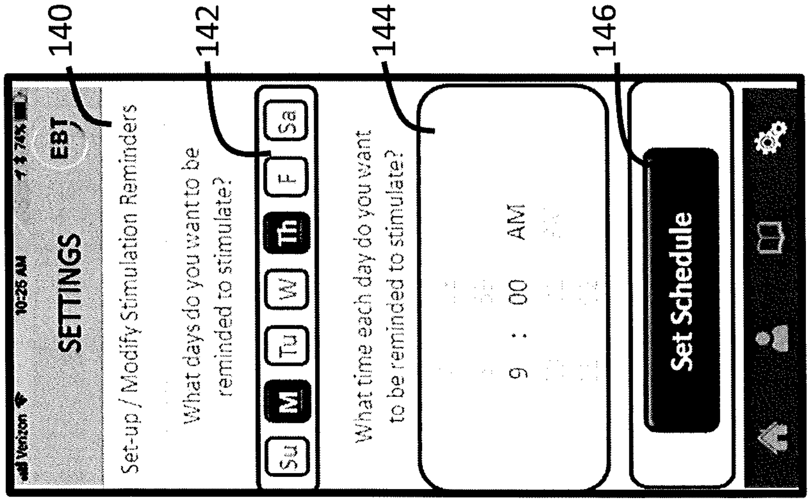
FIGS. 6A, 6B, and 6C illustrates a screen for scheduling reminder notifications for events related to providing therapy; a screen for allowing compliance assessment; and a screen for allowing compliance assessment, respectively.

FIG. 6A, shows a stimulation reminders screen 140 under control of the scheduling and compliance module 60 that has a day-select menu 142 that allows a user to select dates which will be used for stimulation as well as a time widget 144 that allows the user to set the time on each day. When a user finishes selecting a stimulation regimen, the schedule is confirmed with the set schedule button 146 and used to store a schedule of reminder alarms in the scheduling and compliance module 60. Upon the clock of the control module 40 indicating that the scheduled time has occurred the module 60 will present the user with a reminder alarm. If the module 60 is realized in a user's smartphone, then it will allow a "pop-up" on the smartphone display, and provides auditory, vibrational alerting as well if so configured. Reminder alarms for recharging, changing electrodes, or other relevant reminders can be set by user or automatically set based upon a treatment schedule.

Figure 6B:
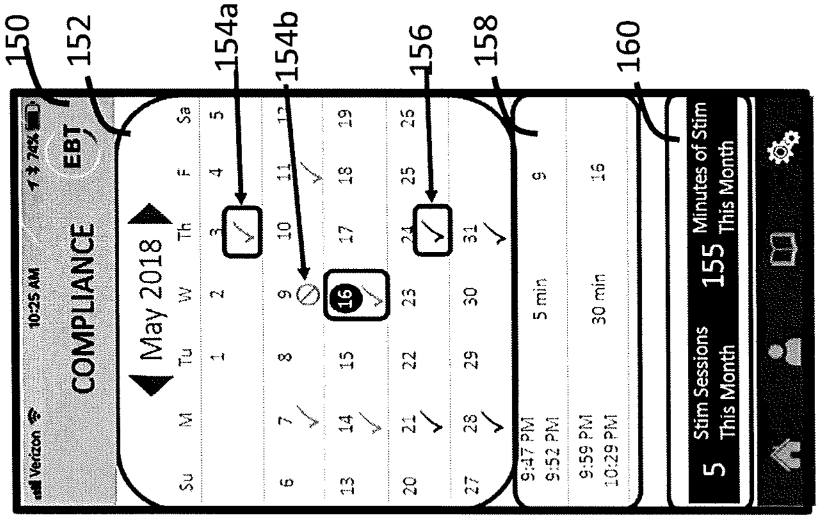

FIG. 6B shows a compliance screen 150 generated by the scheduling and compliance module 60. The screen can be configured for different views, but here shows a monthly view 152 with days of the week and uses symbols (or text) to indicate compliance 154*a*, lack of compliance 154*b*, and future days scheduled for therapy 156. A table of session information 158 enables the collection of information for sessions that occurred on a date, including for example, start-end times, duration of therapy, and session characteristics such as average intensity, total number of pulses, or total amount of electrical charge/energy outputted by device. The screen 150 permits selection of any day to obtain further details on therapy provided. A summary statistics section 160 shows information related to compliance such as sessions completed during that month, total minutes of stimulation, number of scheduled therapies which were missed, number and duration of virtual or in person consults with a health professional, etc. The data and summary statistics are obtained from a lookup table in the module 60 that stores all information related to scheduled sessions and which can be presented for a selected period such as a month. The log of device usage in the device 12 holds data for at least 100 30-minute sessions. If the device is used without a user device 32 or remote computer it wirelessly communicates with, the data can be downloaded every 3 months in a clinic. The data can be stored in the flash memory of the Control module 40. The log file can also time and date stamp open circuits related to the electrode pads detaching and also events related to on-skin/off skin, etc. Although screens shown in FIGS. 6A,6B relate to treatment, scheduling can be related to any other aspect of device operation and events related to treatment including the provision of surveys, taking medication, reminders to go to the bathroom before leaving the house in the morning, questions about fluid intake, virtual or in-office doctor appointments, etc. The usage data of the identification/usage/permissions module 58 can also be assessed for a particular patient's compliance. Measures can be calculated in comparison to treatment goals and report measures such as the percentage of weeks for which stimulation was at least equal to a value parameter set as the minimum number of expected sessions per week.

Figure 6C:
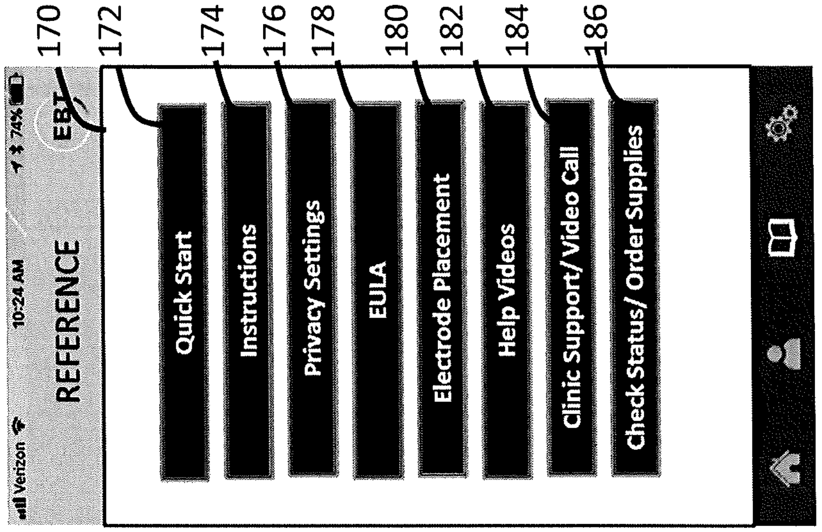

FIG. 6C: Shows a reference screen 170. Selecting the "Quick Start" option 172 provides user with an overview of the therapy. Selecting the "Instructions" option 174 provides user with an instructions and allows presentation in at least one of printed, audio, or multimedia format. Selecting the "Privacy Settings" option 176 provides user with screens for selecting what information is shared with a manufacturer, a selected doctor or clinic, Caretaker, insurance company, or other third party. For example, the user can determine if data is shared or not for categories including: demographics, user identification information, insurance policy information, symptoms, treatment schedule, compliance, purchasing behavior, or responses to categories of survey questions. A user can also individually select data elements that are shared, kept private, or not even stored. Selecting the "EULA" option 178 provides user with an end user license agreement for the system. Selecting the "Electrode Placement" option 180 provides user with various methods for determining if electrode placement is correct for a selected treatment. Additionally, a doctor may use this feature to operate a cellphone serving as an external user device 32 and can take between 1 and 4 pictures of the device or electrodes on a user's leg so that they can return to this reference and view it if they have trouble placing the device. Selecting the "help videos" option 182 provides user with videos about different aspects of the therapy and can serve to provide training or reminding. The viewing of the videos may be scheduled by a user or a physician to occur periodically (once every month during treatment to improve patient compliance and chance for correct home use. Selecting the "Clinic support" option 184 provides user with various methods for interacting with technical/clinical support including sending certain information to a third party (e.g. usage statistics) or having a video call with a nurse practitioner who can help a user to operate the system 8 correctly and answer questions. Audiovisual information may be incorporated into augmented reality devices (smartglasses) to visually guide users to correctly place surface electrodes or may occur under the guidance of the Augmented reality module 70. Selecting the "Check status/Order supplies" option 186 provides user with shopping cart functionality using the shopping cart module 66 and also allows tracking of orders, viewing and adjusting of payment information and history, etc.

On-User Monitoring and Measurement.

The amount of time the device 12*a* is worn is the "on-user" or "on skin" duration. This includes both periods when stimulation is provided (stimulation status=ON or OFF). The on-user module 49 senses, stores, tracks, displays, assesses, and/or acts upon the "on-user" measures such as duration, site of stimulation (left/right), temporal pattern of on-user status changes, and tension (band). For example, it can turn off stimulation and provide an alert to a user (or caregiver) when evaluation of on-user data fails a criterion (e.g., duration exceeds a selected interval). This feature decreases the risk of problems, including skin irritation, due to frequent use or failure to remove the device after use (e.g. forgetting it is worn).

Figure 7:
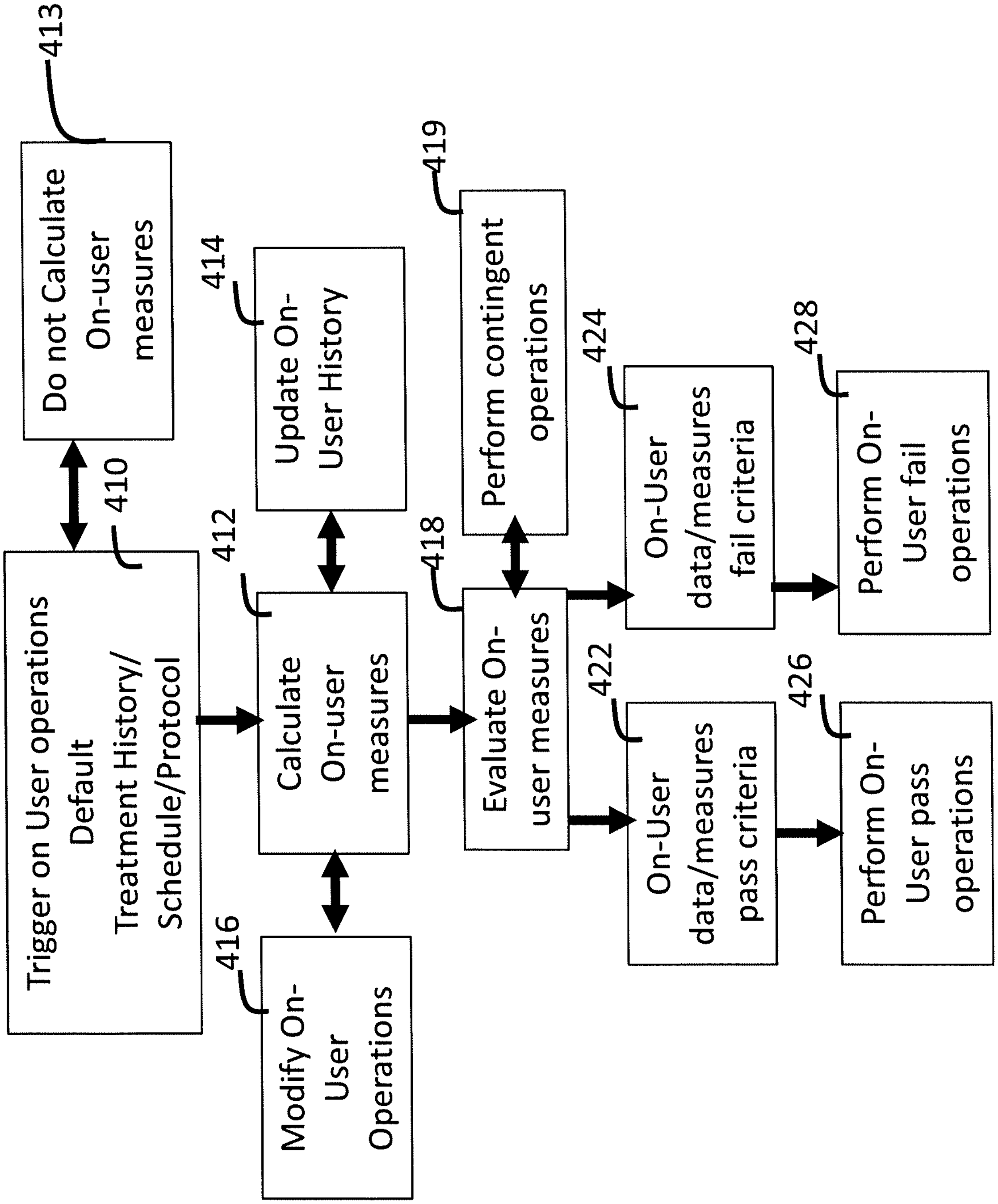
FIG. 7 is an information flow diagram of a method that calculates and operates upon on-user measures.

FIG. 7, shows an embodiment of a method in which on-user duration measurement is selectively or contingently activated in step 410. For example, this is activated if a recent history of stimulation indicates the total time or number of uses exceeds a selected threshold. For example, assessment of calendar data in the Scheduling/Compliance module 60 may indicate a rate of treatment or defined treatment schedule includes frequent or long stimulation sessions. Alternatively, if stimulation history or treatment schedule data indicate infrequent stimulation (twice a week) then the on-user operations remain inactive as part of step 413. Additionally, a user may select whether to activate this feature in step 410. When multiple users share a device, the user-specific history or schedule data are assessed. Depending upon the algorithm, when on-user measurement is active by default, increased use of battery power can occur.

In an embodiment, on-user duration is calculated in step 412 across a period (days or weeks). The measure can be weighted based upon stimulation status (off/on), stimulation intensity, and pressure measurement since this may increase risk of skin irritation. For example, 1 minute of stimulation at higher amplitude can be counted as 2 minutes of on-user time. The on-user time threshold used in steps 422 or 424 can be adjusted based upon a user characteristic such as skin sensitivity. A skin sensitivity value is set based upon a user's response to a question or prompt presented by the survey module 62 related to skin sensitivity, history of skin allergy, etc. User can be asked to rate skin sensitivity (e.g., 1=not very sensitive 10=extremely sensitive) or by periodically asked about occurrence of skin irritation after treatment (Yes/No). On-User time thresholds can be adjusted if a user provides user input data on one or more times that their skin is irritated at a selected time after a therapy session. When a user operates a selected type of stimulation session (session exceeds 3 hours) or protocol (sleep stimulation protocol), or if on-user time over a selected period exceeds a defined threshold value, then the on-user module can contingently 419 operate the survey module 62 to present a user with a skin sensitivity question.

In an embodiment, calculation of on-user measures 412 uses leg status data and calculates measures independently for left or right leg. The on-user history 414 can be calculated separately for awake and sleeping intervals. Leg classification can occur based upon the leg which the user has been instructed to use during therapy by the device, the treatment schedule defined for each leg (based upon data or algorithms of the Scheduling/Compliance module 60), user input data, or otherwise. In step 416, on use operations may be modified by adjusting what measures are calculated based upon system values for parameters such as patient position or activity.

On-user measurement can be calculated 412 when the device determines attachment to a user even when stimulation is off. A user may continue to wear the device after treatment is provided or wear the device, but delays several hours prior to starting therapy. In an embodiment, the on-user module 49 is configured to calculate on-user measures 412 by periodically waking up from a low power state and sensing orientation and activity to determine if on-user status is true. If the status is true, the module 49 extends the time during which it monitors on-user status. Further, if the on-user status is true contingent operations are defined 419. For example, at selected times (30-minute intervals) the device 12 is programmed to emit a set of tones intended to remind a user to remove the device. On-user algorithms are designed to evaluate 418 on-skin measures in steps 422,424 using different criteria before or after treatment is provided, and may be selected or adjusted based upon the selected treatment protocol, or data related to patient demographic (e.g. age), or time of treatment.

Pre-therapy on-user measurement. In embodiments, the system is designed to calculate, evaluate, and determine on-user status, by, for example, a. periodically doing a wake-up and assess accelerometer, impedance, and/or tension data to determine if a user is wearing the device. If sensor data do not meet criteria then the device returns to its low power mode and measuring on-user duration does not occur.
b. detecting the time that an electrode array is attached to the unit. Upon detection its checks for candidate on-user status for a period such as 30 minutes. If candidate on-user status is not confirmed, then the device returns to its low power mode.
c. Operating so that on-user candidate assessment only occurs if the device has at least enough power left to provide a 30 or 60-minute treatment session. This ensures that the device does not become completely depleted simply by checking to see if the device is being worn.

During Therapy On-User Time.

a. On-user time is calculated during stimulation OFF and ON periods during the stimulation protocol for a session which includes both stimulation-ON and stimulation-OFF. Accordingly, a stimulation session includes 3 intervals of 30 min ON, 60 min OFF, then these are calculated separately. On-user measurement also includes "pause" intervals when the user pauses stimulation and then restarts it.

Post-therapy on-user time. On-user time that occurs when a user continues to wear the device after the end of stimulation.

a. Accelerometer wakes up periodically (every 5 minutes) starting after a stimulation session has ended and assess an interval (15 seconds) to determine if the stimulator is vertically oriented and/or if there is movement such as walking;
b. Impedance/strain data is assessed by the on-use module 49 which compares the sensed data to a threshold to determine if the device is still attached to the user.

In an embodiment, the device may be configured to periodically provide a visual, sonic or vibrational notification using the display/notification module 42 if the accelerometer module 47 determines the user is wearing the device. This can also occur if the on-user module 49 is configured to perform contingent operation in step 428 after a selected time has passed from the last therapy session to remind the user to remove the device. The notification can be timed or the user may push and hold a button on the housing 14 of the device 12 to turn off the alarm. Alternatively, if the device is removed the impedance values will increase and this detection will turn off the alarm in step 419. The on-user monitoring module 49 is further configured for comparing the on-skin measurement to a threshold to determine if it exceeds the threshold. The control module 40 is configured to operate upon the result of the comparison such as to adjust device operation and/or operate the display/notification module 42 for alerting the user.

In an embodiment, the monitoring on-user module 49 records values in an on-user history 414 corresponding to start and stop times, stimulation on/off times, sensor data used to assess on-user status (e.g. accelerometer data or user input). The module 49 is configured to operate upon the values to obtain statistics in step 418 such as the total on-user interval across a defined window of time such as a day, 2 days, week, month, or other defined duration. In an alternative embodiment, the summation is a weighted summation which adjusts the on-user time or threshold according to a value such as stimulation intensity or stimulation intensity in relation to a user's sensation threshold or pain threshold.

In embodiments, the on-user module 49 operations are implemented by the device 12, by external patient/user programmer 32, or both. The on-user module 49 also can monitor duration that meets a criterion, such as stimulation above a selected intensity level. The on-user module 49 may operate with the permissions module 58 to restrict use. For example, if the system is used for 3 days, then the stimulation is restricted for 2 days before the system 8 allows the next provision of therapy.

The on-user module 49 can provide user notification including display of on-user time and a visual, a sonic, vibration notification provided by the device 12 or the external user device 32. The system 8 may simply notify a user that an on-user threshold has been exceeded, indicate the next time the device should be used, suspend device operation for a defined time (e.g. until the on-user threshold is no longer true), send a notification to a remote computer at a clinic that monitors user usage, instruct the user to decrease the stimulation amplitude, or may limit the stimulation amplitude. The on-user module 49 may also simply cause the system 8 to instruct the user to use a different stimulation site, such as switching from the left leg to the right leg. Depending upon device permission settings of the permissions module 58, the user may be allowed to simply acknowledge the warning and use the device. Limiting on-user time when stimulation is provided can deter unwanted side effects such as user habituation to stimulation.

In embodiments, on-user status is monitored by sensor on a band such as a strain gauge 132, or by a pressure sensor 134 situated, for example, between the device and the electrode array, or electrode array and skin. The sensed data can be evaluated by the evaluation module 51 to measure the amount of time that the pressure is at least above a selected value that is associated with the user wearing the device. The value can be calculated by instructing a user to wear the device and confirm with user input. At least one summary statistic value related to wearing the device (such as average and standard deviation) is stored in the on-user module 49 and subsequently used for reference and comparison to determine if the device is being worn. Pressure sensor data can also be used to determine if a user applied the band using a tightness level defined as too tight for either awake or asleep therapy session (and increases risk of restricting blood flow) and the system is operated to notify the user. The on-user module 49 can combine strain/pressure, force, impedance, and accelerometer data to determine on-user status measures.

In an embodiment a method for monitoring the on-user duration comprises the steps of: applying a stimulator such as an electrode array 18 to the surface of the user's skin to provide electrical contact between the electrode array 18 and the skin, monitoring the on-user status as a function of whether the stimulation is on or off and storing this to provide a history of on-user status; analyzing the history of on-user status data to determine an on-user result such as the total on-user duration across a defined recent time window, and operating based upon a comparison between an on-user result and an on-user threshold value. In an embodiment, the on-user status is monitored by impedance circuitry using a load value that approximates the electrode-skin interface created by the electrode array placed on the skin of the user when the device is worn, by pressure circuitry using a value that approximates the electrode-skin interface when the unit is worn, or by accelerometer data compared to a value and range that approximates the normal activity of a user. The on-user measurement data can be compared to a baseline reference value obtained from on-user historical data, to a value derived at therapy start or at subsequent intervals (e.g., an expected reference impedance value be adjusted to decrease after a defined interval as the session continues due to the electrodes or other system component "settling in").

Left Leg/Right Leg.

During therapy a user stimulates the left or right leg. In embodiments, the side of stimulation may be indicated by the leg status module 64 providing a signal to the user indicating the device 12*a* should be used on the left or right leg. The indication includes providing a visual or sonic indication by the device 12 or user device 32. This can occur when the therapy is first started and/or afterwards. The indication signaling can include an LED 91 located on at least one of the left or right side of the band. Leg status can also by indicated with a color—for example, red on days that the right leg should be used and blue on days where the left leg should be used, or by presenting text ("L" or "R") on the LCD 120. The leg status module 64 operates to adjust the leg status parameter value of the treatment program provided by the control module 40, the On-User module 49, and scheduling/compliance module so that all of these may operate by taking this information into account.

The leg status module 64 algorithm operates upon the usage history of the scheduling compliance module 60 and determines and displays via the display/notification module 42 leg status information. This information includes the leg used for the last treatment or the leg which should be used for the current treatment. The module may obtain user input or prompt user input about which leg is being used for the present treatment session. The leg status module 64 algorithm may operate to instruct a user to use an alternate leg at selected intervals such as every other day or week, or after selected number of sequential treatments. The leg status module 64 may only signal a leg to be used when stimulation is provided for extended periods of time (e.g. >1 hour per day). The leg parameter value can be operated upon by the system to set, retrieve, or adjust parameter values differently for left or right.

It can be important to set the left/right leg parameter value accurately so that algorithms used by the system 8 operate correctly. For example, the measurement of leg orientation relates to body orientation and can suggest whether a user is supine or otherwise recumbent. For example, when the device is oriented to be worn with a particular angular disposition relative to the leg (e.g. vertically on front of leg), then when the accelerometer/level detector indicates it is horizontal and facing upwards this will suggest either that the user is supine or the person has their leg extended (e.g. the leg is elevated on a chair). In an embodiment, the user interface module presents a graphical representation of the user's body or presents a list including a) front of leg, b) back of leg c) inner leg, d) outer leg, e) left leg or right leg and the user can choose the device location where the device is worn. The device then operates according to the device location for the remainder of the therapy session.

In an alternative embodiment, the device operates upon user movement data to determine and/or confirm device location or orientation. For example, a walking algorithm implemented by the accelerometer actigraph module 47, will 'expect' a particular signature on the x-y-z axes, when the device is located on the front leg. For example, more force should be measured along the positive y-axis direction when the user walks forwards. If during walking the force is greatest in the positive Y-axis direction then this indicates the user is wearing the device on the right, (i.e., inner-leg of the right leg or outer-leg of the left leg), while if the measurements are greatest on the negative Y-axis direction, then the device is on the lateral surface of the right leg (or medial-aspect of the left leg). The system 8 may prompt the user to confirm the estimated position at which the device resides, or may simply prompt the user to input this information if it is not estimated from sensed data.

One or Both Legs.

When providing treatment and monitoring, combining operation of at least two devices located bilaterally (for treatment sites on arms, legs, or otherwise), rather than operating each independently, has advantages. With respect to assessment, for example, actigraphy using data sensed from two legs, may provide assessment or statistics for the two legs separately or in combination. With respect to stimulation, jointly operating two bilaterally located devices allows coordinated stimulation so that the at least two devices stimulate at the same time, in an interleaved pulsing fashion, alternating, or otherwise (with respect to either the stimulation signals or the periods during which each device provides stimulation). Advantages of combination stimulation include decreased stimulation (e.g., number of pulses) provided at each leg (when alternating) or increasing the strength of signal received at the level of the spine or brain (when synchronous). In some users, using 2 stimulators to provide stimulation concurrently may allow benefit to occur using a lower stimulation intensity than needed when only stimulating 1 leg. When two devices are operated jointly, they communicate with each other, and/or with a user device 32 operated by a user or physician.

The system 8 provides stimulation or assessment using 1 or 2 legs using one of the 1-leg or 2-leg treatment protocols defined in the control module 40. In an embodiment, at least two wearable stimulation devices 12 are configured to cooperate in providing combination stimulation such as alternating stimulation intervals provided to each leg. During synchronous stimulation, the stimulation may combine at the level of the spine or centrally. This integration can cause a 20 Hz signal applied to each leg to combine to net frequency 40 Hz at a more rostral location which receives input from both stimulation locations. The net stimulation signal can be adjusted using a delay or lag parameter value to provide synchronization of the stimulation waveforms of the two devices. In an embodiment, 10 Hz stimulation occurs on each leg to produce a net stimulation signal centrally as a single signal then 10 Hz, while an alternative stimulation protocol causes the pulses of the signals to arrive more centrally (to the sites of stimulation) at different times so that 20 Hz is net signal drives these more central targets. The lags of the two signals may be set using population normative data, sensed data from the user, or user input.

During treatment of OAB, pain, addiction, cardiac disorders, obesity, or other disorders at sites on the legs or arms, alternating sides of the body or stimulating bilaterally may offer advantages compared to consistently using the same location.

Accelerometer Usage

Figure 7A:
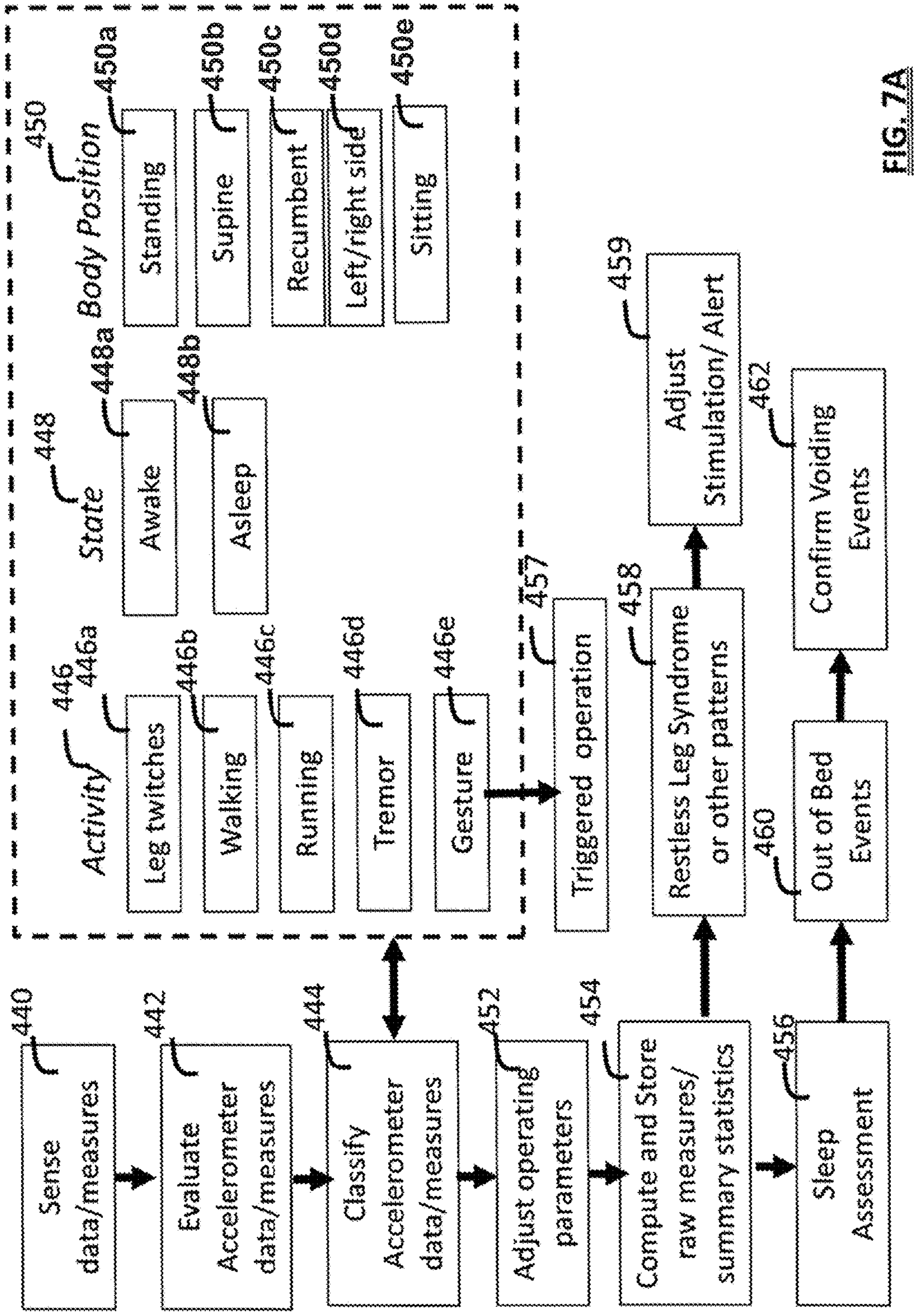
FIG. 7A is an information flow diagram associated with user activity, state and body position.

Measurement of data related to, for example, movement, direction, acceleration, and orientation can provide advantages such as adjusting therapy in response to user activity. In an embodiment, the accelerometer/actigraph module 47 includes a FXLS8471Q accelerometer (made by NXP/Freescale) which allows 3-axis measurement. The accelerometer can measure acceleration (including the static gravitational field, which can be removed using high-pass filtering) and also provides embedded DSP functions for measurement of acceleration-vector magnitude detection, freefall/motion detection, transient acceleration, single/double pulse (tap) detection, and orientation detection. There is also active mode and an active sleep mode. As shown in FIG. 7A, either raw data output or measures output from DSP functions can be obtained 440 and used to detect user behavior such as tapping or double tapping the device 12, transient motion, walking or detect body position such as an upright or horizontal leg (i.e. is not walking).

The detection of a transient motion of a user can relate to acceleration which exceeds a threshold for a minimum duration, for at least one of the axes. The sensed data including accelerometer readings can be evaluated 442 using an algorithm operated by the accelerometer/actigraph module 47 and/or by algorithms native to the accelerometer. The sensing 440 or evaluating 442 may include low-pass or band-pass filtering (e.g. filtering between 1 and 60 Hz), creating data windows for analysis (which may last 1 to 10 seconds or even 1 minute or longer), and rejecting noisy data windows that meet artifact rejection criteria. Histograms, counts, and summary statistics are calculated only based upon data of acceptable quality. To save memory, data can be down-sampled at any step prior to step 454 (400 Hz truncated to 50 Hz).

Next classification of the raw data/measures 444 occurs. This can be adjusted based upon data related to clock time, the stimulation protocol selected by the user, or a recent history of activity data assessed by evaluating a series of accelerometer measurements over a time selected interval. For example, during a clock time when the user is typically sleeping (e.g. 3 a.m.) the thresholds used by the actigraph algorithm related to duration and acceleration may be decreased to measure leg "twitches", rather than using those defined to detect walking or other activities that occur when the user is likely awake.

A lookup table of parameter values or thresholds for durations, orientations, forces, and acceleration can be provided in the accelerometer/actigraph module 47 and used to classify the raw data and derived measures 444 into user behaviors such as leg twitches and other body movements. In an embodiment, the accelerometer data is classified into three classes: activity 446, user state 448, and body position 450, which are not mutually exclusive (e.g., a user may be both lying down and asleep). For example, user activity is classified into leg twitches 446*a*, walking 446*b*, running 446*c*, tremor 446*d*, or gesture 446*e*, and each of these has its own derived measures. User State 448 includes, for example, classification awake 448*a* or asleep 448*b*. Body position for example, includes standing 450*a*, supine 450*b*, recumbent 450*c*, left/right side 450*d*, or sitting 446*e*. The classification of sensed data to determine the activity, state, and body position of the user is used to adjust operating parameters 452 including stimulation protocol parameters, and therapy events such as presenting a survey, changing criteria used to evaluate subsequent data, etc.

The table values used during classification 444 can be based upon correlating leg electromyogram (EMG) data collected on a group of users who are sleeping with accelerometer data to detect useful parameters for detecting movements such as leg twitches. Classification and assessment of other activity (behaviors), such as walking are similarly based upon normative values obtained using study data while having users do certain actions. Alternatively, the values can be self-normative and obtained by having a user perform a set of calibration operations when they first use the device, and/or periodically thereafter. Accelerometer data allows the system 8 to obtain actigraphy summary statistics 454 and operate to provide sleep assessment 456 (i.e., polysomnography, which may include other sensed measures such as EMG). When pairing with a user/patient device 32, the system may prompt what body part a device is being used on so that it can assess sensed data correctly (e.g. left leg or arm). The data obtained from at least one device can be combined with data from other sensors such as EEG to provide measures typically used in polysomnographic assessment.

Actigraphy

In an embodiment, the device 12 may be worn while the user is sleeping to assess sleep-related measures 456 such as sleep quality or duration. User activity that is measured during sleep by the accelerometer/actigraphy module 47 can be used for various purposes. For example, it is possible to measure "restless" leg movements (strength, frequency, etc.) which may often occur prevalently at sleep onset. These can be measured for an interval defined by time to include a period at sleep onset, and/or may be assessed for 1 or more intervals that occur during the night.

Actigraphic data can be assessed both prior to the start of stimulation therapy (baseline reference) and at 1 or more defined times that occur as therapy progresses. These actigraphic data can be stored 454 in periods segregated into, for example, baseline, induction, maintenance, and post-treatment as part of step 454. A remote computer in a clinic can be used to download, compute summary statistics, and display data related to each of these periods. In an embodiment, baseline summary statistics are obtained during an assessment which includes operating the system 8 to monitor these sensor data. The actigraphic data can be combined with data from other sensors, such as a microphone 93 included in the sensing module 50 of the system. The control module 40 is configured 474 to operate in a "non-stimulation" or "actigraphic-only" mode 470*a*. When "actigraphic-only" mode 470*a* is selected, the circuitry and software instructions that might otherwise typically be used by the device 12 to assess system status and confirm for example, impedance is below a selected acceptable threshold (or to perform other types of status checks normally provided during stimulation) are not implemented by the processor of the control module 40. For example, the system 8 is configured with a baseline protocol that collects baseline actigraphy data for several days or weeks prior to starting therapy.

Figure 8:
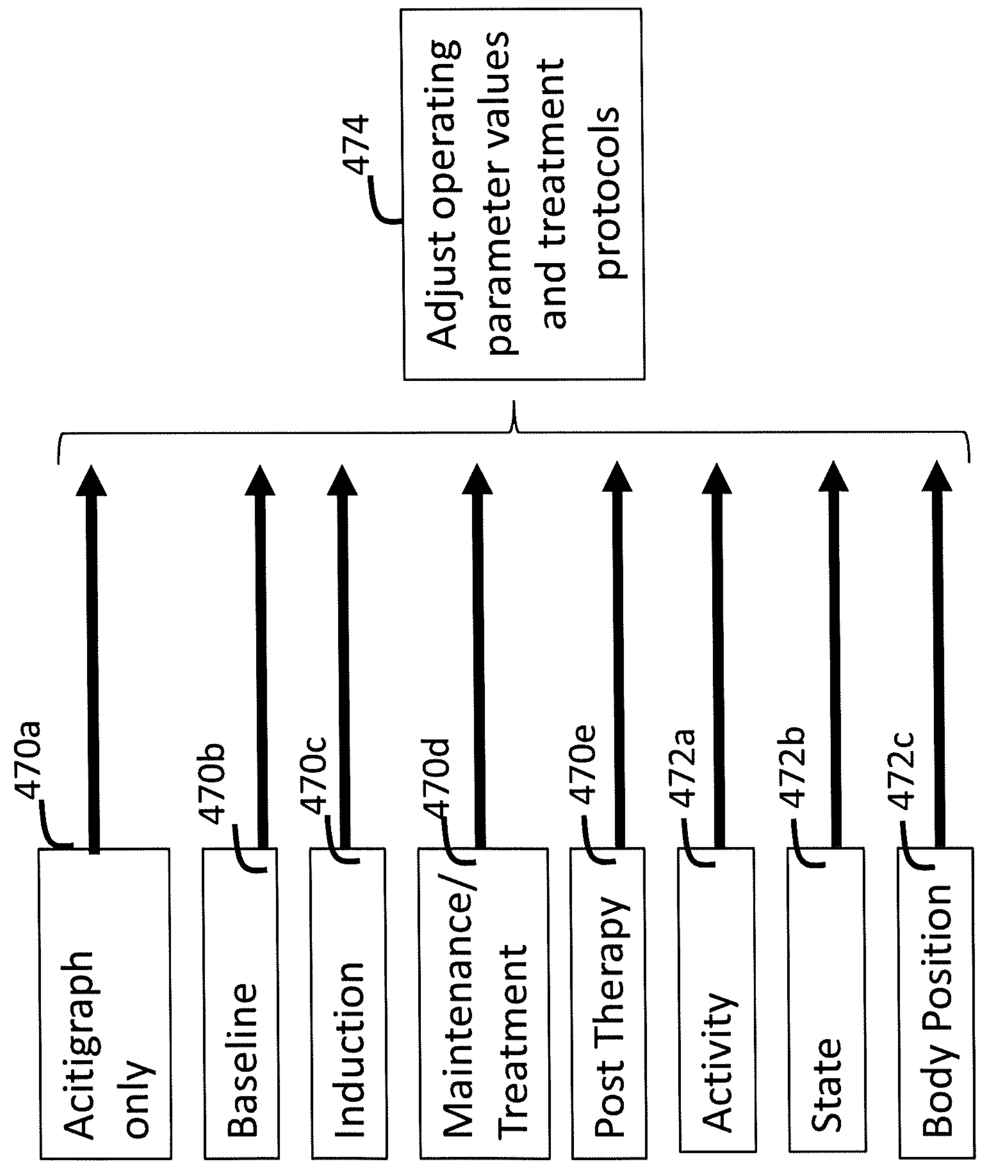
FIG. 8 is an information flow diagram of operating modes used to adjust system operation and protocols.

As shown in FIG. 8, modes are not mutually exclusive, for example, an actigraph-only mode 470*a* and a post-therapy mode 470*e* can occur at the same time. In baseline mode 470*b* the user may be assessed until a stable baseline meeting baseline criteria are obtained, for example, if the urgency or frequency score computed upon measures shows too much variability then the baseline mode may be extended in time. The induction mode 470*c* can operate to provide a more intensive therapy dosage using both increased frequency and duration of treatment sessions, and will not transition into the maintenance mode 470*d* until user data suggests symptom improvement has been detected, or a minimum amount of time has passed with the user in the induction mode. Each mode may have its own schedules, surveys, and criteria for adjusting operation and evaluating use input data.

Further, user status 472 including activity 472*a*, state 472*b*, and body position 472*c* can serve to adjust system operation and parameter values 474. For example, during the actigraphy-only mode 470*a*, the electrodes do not have to be attached to the device, no minimum is required for stimulation amplitude, and the system provides an indication in at least one modality that stimulation is turned off. This mode saves battery power, prevents the On-User history classified for "stimulation on" from being updated (since no electrodes are in contact with the user's skin), and allows collection of a pre-treatment baseline in which collected data is classified and stored as a baseline dataset. The control module protocols are configured so that raw data and summary statistics of the baseline dataset is not combined with data measured and/or assessed during the provision of therapy and is not included when summary statistics are computed upon the treatment-related data (except to provide a reference dataset for comparison). This feature can be extended to different disorders and the measurements (e.g. heart rate, blood pressure, frequency of voiding, urgency, number of night-time bathroom trips) obtained and stored as user baseline data.

Some users have increased sleep interruption due to incontinence or urgency. This may occur more frequently in the period soon after falling asleep or just before waking up. Accordingly, in an embodiment, the control module 40 is programed with a sleep stimulation protocol that stimulates (or increases stimulation strength) during those intervals (e.g., for 1 to 2 hours after sleep onset is detected). The intervals may be defined by times normally going to sleep, times defined by user input (a button press indicates a person is going to bed and stimulation should start 30 minutes later and last for 1.5 hours), or evaluation of sensed data 442. Leg movement patterns that precede bedwetting may have a signature for certain users (one or more distinctive characteristics such as sudden increase in density of movements). Upon detection of this leg movement activity 458 characteristic the device is programmed to perform a contingent operation 459 such as adjust, increase, or start stimulation to provide acute inhibition of bladder activity. Additionally/alternatively, the contingent operation 459 can be defined as providing an alert signal such as sonic alert to wake up the user and permit voiding in the toilet rather than in the bed. Instead of a sonic alert a signal can be sent via communication module 52 to an accessory 81 such as vibration device provided on the wrist (bracelet, smartwatch) or upon a mattress of a child.

During nighttime use, the therapy protocol can provide stimulation continuously or for defined intervals (60 minutes) during sleep, with stimulation off intervals (30 minutes). The actigraph module 47 can classify 444 measures calculated upon sensed activity according to whether the stimulation was on or off, and as a function of stimulation protocol. For example, rather than stimulation-OFF, the stimulation protocol can include both Stimulation-higher and a Stimulation-Lower condition, where stimulation is set at two intensity levels. For example, the stimulation low protocol provides stimulation that is slightly above the nerve recruitment threshold (or otherwise lower than that used during the stimulation-high interval). In users who have incontinence during the night, some low amount of stimulation provided during the entire night can be helpful. In an embodiment, stimulation intensity is varied as a function of classified sleep state.

Sleep-wake states and sleep stages, or at least a measure associated with depth or quietness, can be determined 456. If bedwetting is associated with certain (e.g., deeper) stages of sleep then the device can implement a treatment protocol which adjusts stimulation according to defined protocol.

Sleep actigraphy data calculated using module 47, to analyze sensor data provided by the accelerometer, allows sleep assessment (Marino et al, Measuring Sleep: Accuracy, Sensitivity, and Specificity of Wrist Actigraphy Compared to Polysomnography, Sleep 2013). An accelerometer is located within the housing 14 or in an accessory 80, such as a device worn on the wrist (e.g. on the user's dominant or non-dominant arm) that communicates data to the system 8. The actigraph module 47 is configured to classify sleep patterns or other patterns (diurnal rhythms), and derive measures such as latency before falling asleep, and duration, quantity, and severity of restless leg syndrome. This allows measurement of interventions (such as OAB medication) on sleep quality or restless leg syndrome. Restless leg syndrome severity may be scored 458 using number, size or duration of movements, periodic limb movement index, or International Restless Legs Severity Scale.

In an embodiment, when long stimulation sessions (e.g. >1 hour) are provided then continuous or real-time communication between the device 12 and system components such as the user device 32 is paused to decrease battery usage and avoid disadvantages including perceived health concerns. Wireless communication is enabled for an interval (e.g., the first 15 minutes after a sleep program starts) and is then suspended for the device 12. Wireless communication is restarted due to a defined trigger such as time, user input, or sensed data. For example, the module 47 is programmed to recognize a user providing a gesture such as a selected number of taps on the device housing, or standing up, and to contingently operate 457 based upon detection of the gesture. Pushing a button on the device housing 14 or determining clock-time is within 30 minutes a time defined for a user to wake up can also trigger communication restart. The user device 32 can also emit a sonic signal such as sound pulses that are not audible to a user, which serves to restart RF based wireless communication if detected by the microphone 93 operated by the device 12.

In an embodiment, the device is programmed to respond to user gestures defined to cause adjustment of device operation. User-selected or defined gestures such as stomping their leg 2 times are programmably incorporated into operation. For example, during a training period the accelerometer/actigraph module 47 interacts with a user who performs a gesture so the system 8 can derive an associated template for the gesture. Gesture templates are subsequently compared to sensor data to determine if a user gesture has occurred which is a type of classification that occurs in step 444.

In an embodiment, the device 12 detects candidate "bathroom events" as part of a treatment protocol 460. The number of times that accelerometer data registers walking can be counted. At a selected time the next morning, a list or summary of out-of-bed events is presented to the user by the user device 32, and may include times and durations of the out-of-bed events. The user is prompted to confirm the number of these which were voiding events 462. For example, the information "You had 5 out-of-bed events, please indicate how many were bathroom related". The user can enter the number of that were bathroom events, and may also provide a score for urgency or incontinence for each.

Treatment of OAB should avoid interfering with sleep quality and should even improve sleep quality. Allowing for the quantification of sleep quality and quantity 456 allows such assessment. Improvement in measures related to sleep disorders or sleep quality may incentivize compliance. Stimulation of the SAFN for the improving sleep quality and quantity, even in non-OAB users, is an objective of the invention. Support for this use is derived from OAB-studies conducted by the inventors that show improvement in sleep related measures, which may be independent of improvement in OAB symptoms (MacDiarmid, Yoo, and John, 2018). Stimulating other nerves in the leg may also improve sleep. Trend measures can be stored and displayed across a period of days, weeks, months, or years to show a history of patient symptoms 454.

User Interaction, Surveys, and Questions.

In embodiments, the system 8 interacts with the user upon first use under control of the user interface module 44 working in conjunction with the survey module 62. When used under medical supervision, a doctor can set what questions are presented to a user by interacting with the setting parameters in the identification/usage/permissions module 58. A doctor may work with a version of the user device 32 that serves as a physician programmer to adjust the parameter settings related to user surveys.

Figure 9:
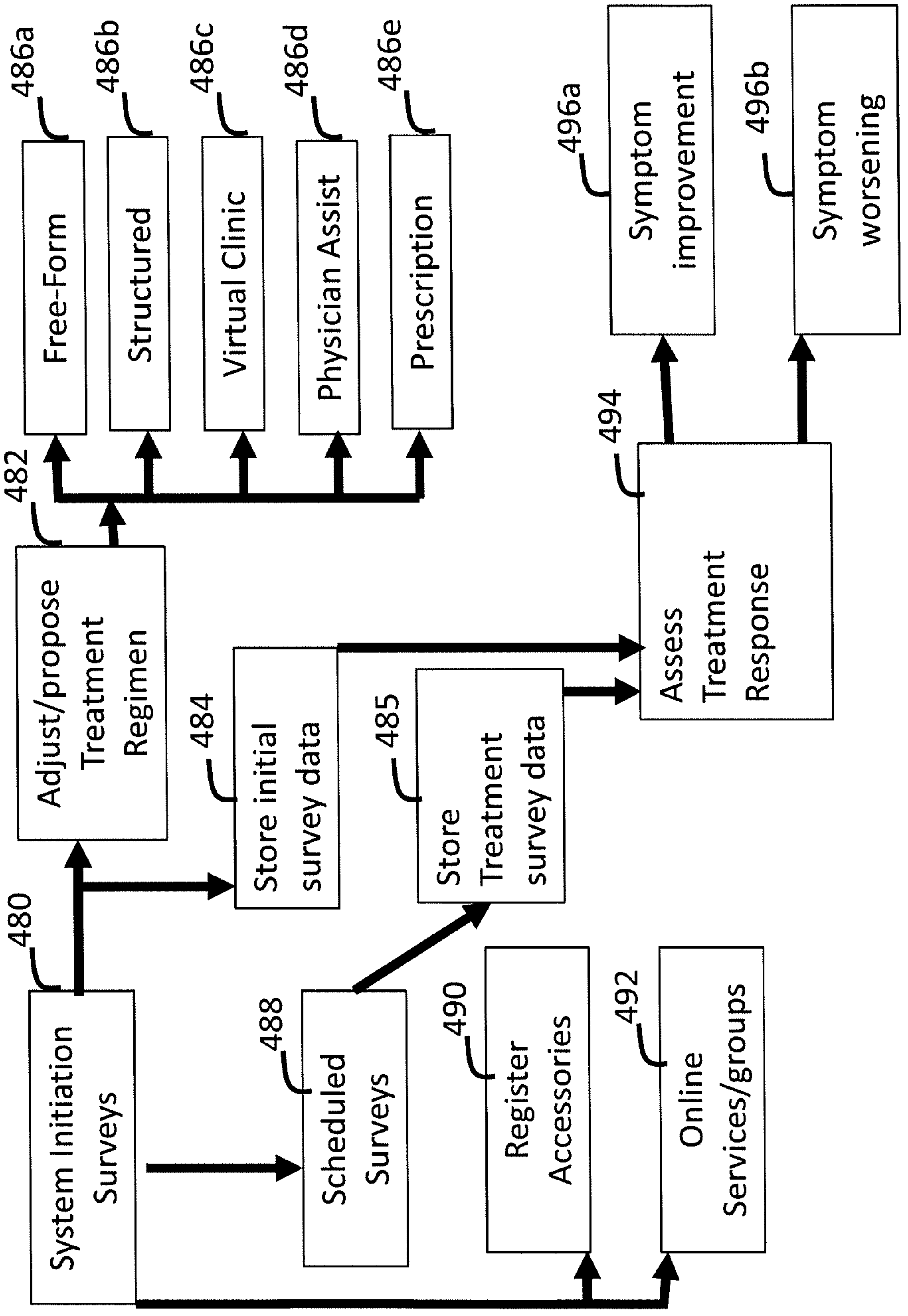
FIG. 9 is an information flow diagram of a method for providing user surveys and operating responsively to user input data.

FIG. 9 shows that upon first use, a user is prompted to create a nickname/profile and is asked to answer some background survey items 480. Background survey items can include for example, questions about demographics (age, gender, weight), treatment history (past-present drug types and dosage), history of their disorder (time since onset of symptoms), comorbidities, recent trends (stable, better, worse) and characteristics of the disorder. Users can opt to answer each category of survey questions or not (e.g., No; Yes, answer now; Yes, answer later).

In the treatment of OAB, the initial survey items may include items of the OAB-q which allows assessment of different quality of life categories such as "coping", "concern", "sleep", "social" and "health related quality of life (HRQL) total". The system may prompt the user to complete a digital bladder diary covering 3 or 4 days and OAB-Q prior to providing the first stimulation session. A schedule for presenting these items at increments thereafter such as at 4 weeks, 8 weeks, and/or 12 weeks may also be proposed. The system can operate in Study mode, which allows for questions associated with a study protocol to be imported into the system for presentation to the user in a customized manner. Rather than using survey instruments with many questions, the user may simply be asked to estimate the severity of their disorder by indicating number of daily/nightly voids, urgency, severity of incontinence, presence of nocturia and enuresis. Symptoms related to other pelvic floor disorders may also be assessed such as fecal incontinence, pelvic pain, etc.

The treatment regimen, which includes treatment protocols, schedule of prompting a user to respond to survey questions, and any other operation related to the treatment and assessment of the user may be adjusted 482 based upon the user responses to survey questions presented during system initiation 480. The user data input in response to the survey items are also stored to create a reference dataset 484.

In step 482, the system 8 adjusts therapy parameters according to the severity of the symptoms as is assessed by user input data provided in response to the survey questions posed to the user. For example, in treatment of OAB, a protocol having more frequent or longer stimulation sessions may be selected or proposed to a user who voids, for example, 20 or more times per day. Less frequent or shorter stimulation sessions will be used for a user who only has, for example, 10 bathroom trips per 24-hour period. The system can simply prompt the user to rate their condition as mild, moderate, or severe (with some brief explanation about what each entails) and can adjust or suggest a corresponding treatment protocol schedule. The criteria for assessing OAB severity and the corresponding treatment protocols can be stored in a look-up table, and simple logic used by an algorithm of the survey module 62 to adjust or propose a treatment protocol 482. In addition to severity and presence of selected symptoms, the survey module 62, may alter the regimen 482 according to the timing of symptoms. For example, users who indicate they suffer from sleep disturbance or bedwetting may cause the module 62 to suggest to the user that therapy occur during the night, just before bed, or while sleeping.

The system may initially, and/or periodically, allow the user to select one of several modes for the treatment. The control module 40 will then operate in a specific treatment mode. For example, a free-form mode 486*a*, which is unstructured and the user provides therapy at will, with little or no surveying, compliance notification, or interaction. A structured mode 486*b*, in which the user is provided with, or otherwise establishes, a schedule for stimulation and is prompted for input periodically. A Virtual Clinic mode 486*c*, in which the user is provided with a schedule for stimulation and also has regular interaction with the device including answering questions for evaluation and management purposes related to treatment response. A Physician Assist mode 486*d*, in which user data is provided to a physician who may be located remotely and who works with the user to adjust therapy based upon user provision of treatment and therapy progress over time.

In an embodiment, the user can simply adjust what operations are provided as part of therapy by selecting desired features of therapy from a list which includes, for example, survey, compliance reminders, instructional videos, symptom tracking, etc. The system may also operate in an assessment mode (or baseline mode 470*b*) where the user is assessed over a 3 or 4 day period without the provision of therapy and interacts to provide baseline data related to symptom severity. When the system is used as a prescribed therapy mode 486*e* that is reimbursed by insurance, the mode 486*e* of the device may restrict parameter values and survey items to those set by a physician and include operations such as remote monitoring to assess compliance.

Survey questions presented at system initiation 480 can be used to determine the content, schedule, and type of questions that are presented to the subject during treatment. The survey can occur using rules, algorithms, look-up tables, logic-trees, or machine learning techniques. For example, if a user indicates that they do not get out of bed at night to urinate, then the survey module 62 could set a flag so that the steps of the treatment program related to evaluating out of bed events to determine if they are bathroom events 462 can be de-activated. Accordingly, even if the user gets out of bed during the night, the user is not burdened with questions about voiding the next morning. In another example, if a user indicates that they do not have sensitive skin then the system suspends, or decreases the rate, of surveying the user about skin sensitivity/irritation. Control laws, machine learning, and other algorithmic solutions that operate upon sensed data or user input can be implemented as therapy progresses.

Example survey items (and sample and choices) presented to a user initially 480 or as treatment progresses 488, by the survey module 62, or by a physician who is programing the system 8, include the following categories:

1) Frequency of interaction. The user is prompted to select from options such as daily, several times a week, once a week, every other week, once a month, or only during initial set-up. Additional survey items determine the schedule and times of interaction and what topics will the user be surveyed on. Screens for customizing a schedule for surveys may be realized similar to screens 140, 150.

2) Survey Modality: the user is prompted whether survey items should be presented visually on the screen, sonically by audible survey items which are verbally responded to with speech recognition, or accomplished using a voice service interface such as Apple Siri or Amazon Echo, that the system interacts with to register itself 492 and become integrated (e.g. integrations “Alexa skills”, “Home Connect Line”) using IOT protocols.

3) Security: the user is prompted to add security features that enable access to settings and data on their user device 32 or remote cloud based account?

4) Privacy: the user is prompted to determine what user/survey data (e.g. health information) is shared, for example, a manufacturer may wish to track symptom change over time and compliance.

5) Level of Instruction: the user is prompted view instructional videos about set up, provision of therapy, lifestyle changes, and other topics and to set a schedule for periodically being prompted to view these as therapy progresses.

6) Accessories. the user is prompted about use of accessories 80 such as a bathroom sensor that measures flushes or when the user enters the bathroom? If the user indicates that accessories (e.g. 81, 81*a*) will be used, then it can be selected from a list or IOT/RFID technology and protocols enable device recognition of accessories 490 such as an accessory 81 that “pings” the device if it is within a selected radius such as 5 feet. The system can then monitor frequency of bathroom visits.

7) Report generation. Do you want to be shown reports related to symptom improvement (sleep quality) that might be affected by your treatment?

8) OAB symptom and lifestyle assessment survey items can include those which ask the use to rate the presence/absence, or frequency (e.g., 1-10: 1=never; 10=many times daily), and then severity (e.g., 1-10: 10=most severe) of symptoms, such as:

Urge incontinence sudden onset causing incontinence

Urgency

Stress incontinence (i.e. laughing or sneezing makes you pee unintentionally)

Bedwetting (enuresis). If this is present the user can be prompted whether operations should occur upon detection of moisture (e.g., vibrate device, emit a tone, or send an alert signal)

Nocturia

If a user indicates nighttime voiding then the survey module 62 used pre-defined logic tree rules to contingently prompt a user to provide further information:

a) Number of nightly bathroom trips b) Bedwetting episodes per week c) Willingness to stimulate at night while sleeping? (Y/N)

(1) If the user responds “Y” the system may prompt the user to indicate typical times for going to sleep and waking up.

(2) Otherwise the user is prompted about allowing stimulation at a time near going to bed, and may prompt the user to provide typical times for going to sleep and waking up.

d) Increased likelihood for voiding/incontinence just prior to waking—would you allow a night-time stimulation protocol (e.g., begins 2 hours before wake up)?

Symptom timing. When do OAB symptoms occur most frequently: a) at night, b) just after going to sleep, c) upon waking, in the morning, d) during the day, e) about the same regardless of time, f) it changes on different days (for each the user selects 1-10: 1=seldom and 10=frequently)

Are particular days worse than others? M, T, W, TH, F, Sat, Sun.*

Induction Schedule. The survey module 62 displays a candidate induction schedule (and session duration or stimulation “dosage”) based upon an OAB severity score calculated upon user data input to the above survey items and/or Background survey items. For example, “You have indicated a symptom severity of 7 on a scale of 1 to 10, with 10 being severe. For a user rating of 7-10 it is best to stimulate every day for the first 2 weeks, are you willing to do this?” (Y/N). If the user selects “N” then the user is prompted their preferred rate of stimulation. This user input data is used to adjust the minimum required data accepted by the scheduling screen 140 and associated compliance statistics displayed 160 during treatment.

9) Stress-anxiety. A user is prompted to indicate increased period of stress or anxiety so that these can be tracked on the calendar and reviewed by a physician to understand if symptom become worse during a particular interval. During a stressful period the user can also be prompted to increase their stimulation dose. Environmental factors such as hot weather can also be used to update the calendar by having the communication module 52 obtain information from a remote computer 80, such as days when local temperatures above 95.

10) Medication. Length of medication for overactive bladder and current medication status.

a) If a user indicates positive current medication status, they may be surveyed about type and dosage using a menu drop-down increased accuracy.

b) A user with positive medication status may be prompted to permit reminder notifications. If this is allowed, the user is presented with a schedule screen 140 to set a reminder schedule.

c) Each day the system 8 can prompt the user to confirm if medication was taken. The system can incorporate both the medication and stimulation schedule into the compliance screen 150 to measure combination drug-stimulation compliance.

11) Online services/groups. The user is prompted about use of bathroom-location and pharmacy mapping or membership in OAB online communities. If the user is an existing users/members the control module 40 links functionality (e.g. measures how many times a bathroom finding application such as "Sit or squat" or "where to wee" is used), if not then it may prompt a user to join the service/group 492 or link the user to an internal user group or database (with map-guide locations of public bathrooms).

12) Sleep Improvement. A user is prompted to indicate whether they suffer from apnea/snoring. The survey module 62 prompts a user who snores to confirm whether snore detection should be provided using the microphone 93, and if/how the system 8 should respond. For example, if the actigraph module 47 analysis indicates the user is sleeping on their back and snoring is detected: then the device vibrates, issues sonic notification, or other notification signal.

13) Fluid intake and user behavior. The user can be prompted, for example, about number and timing of 8 oz cups of coffee consumed (on average), wine, water, soda, and alcohol consumption, remembering to use the toilet prior to leaving the house and driving to work in the morning, etc.

a) Measuring and tracking fluid intake is important since OAB symptom improvement may be reflected, or obscured, by increased intake rather than decreased voiding.

14) Comorbidities. Users are prompted to indicate comorbidities such as: arthritis, diabetes, diabetic neuropathy, sciatica, neuropathy, fibromyalgia, restless leg syndrome, shingles, cancer, multiple sclerosis, spinal compression/injury, paralysis below the waist, accident/injury, epilepsy, migraine, or "other". A list with checkboxes allows user selection, or indication "do not wish to answer".

When used in a clinical setting a physician can download the survey data from the device when the patient is in the clinic, or can upload data about the patient that has been entered into the electronic data records of the clinic or entered using a web interface. Accordingly, when the system is initialized 480 it can prompt the user whether survey data will be manually entered or whether this should be uploaded.

Periodically as treatment progresses the system presents the user with additional surveys 488 which are scheduled or triggered based upon user input data. The survey data obtained during treatment is stored 485 and is compared 494 to treatment survey data from an earlier time or initial survey data. The results of this comparison can determine if there is symptom improvement **496*a* which can trigger symptom improvement operations 496*a*, or symptom worsening 496*b*, or no change in symptoms (not shown). Steps 496*a* and 496*b* can lead to adjusting treatment 482**. Accordingly, therapy adjustment occurs according to the response to therapy as is assessed by the questions posed to the user over time.

In a clinical environment, patients typically undergo induction once per week during induction, and for "responders" this is followed by treatment once every 3 or 4 weeks during "maintenance". Increasing therapy "dosage" to more than 1× per week can reduce delay before benefit occurs. In a TENS (or implantable) therapy that is provided in a home setting, the user may be asked questions about symptoms once a week, starting after week 3. After benefit is reported by the user that meets one or more selected treatment criteria, the system can prompt a user to transition to a "maintenance schedule". Maintenance therapy sessions may be less frequent, or shorter, or otherwise have less overall amount of stimulation than the induction therapy. The type and degree of symptom improvement required to trigger transition from induction to maintenance can be defined, for example, using criteria of a look-up table. Improvement criteria may be based upon initial symptom characteristics, severity, and/or size of symptom improvement. The table may be selected according to an appropriate aged- and gender-matched population. An algorithm may simply use a treatment benefit criterion of 30% improvement in OAB, for one or more measures of urge, frequency, or incontinence.

Setting and/or Adjusting Stimulation Parameter Values

In embodiments, systems and methods are used to algorithmically assess/set an intensity parameter value (or other stimulation parameter value such as pulse width). Setting intensity parameter values can include determining multiple thresholds and ranges. A therapeutic level used during an awake protocol should often be set between a minimum effective level (recruitment threshold) and a maximum level that is less than the level at which a subject experiences pain or discomfort. Given the subjective nature of stimulation-evoked sensations, the dynamic range between the minimum and maximum stimulation levels may vary significantly among patients.

In an embodiment, systems and methods operate according to four pre-defined or user-defined levels of electrical stimulation. A sensation/perception threshold level is defined as the lowest level of electrical stimulation causing a user to report any sensation of stimulation at the location of the electrodes. A recruitment threshold level is defined as the lowest level of electrical stimulation that indicates or confirms nerve recruitment. For the SAFN at or below the knee, this may be associated with a paresthesia experienced as radiating away from the site of stimulation. The evoked sensation may be experienced as one that radiates down the leg, or into the foot/toes. If stimulating lower towards the medial malleolus, a person may report radiation upwards within the medial aspect of the leg. The sensation and recruitment thresholds may occur at the same intensity, but the latter will typically be higher than the former. Although the two terms maybe used interchangeably in some embodiments, the distinction is important when made as part of the current invention (especially for TENS or percutaneous embodiment using SAFN stimulation). In the case of the PTN, the recruitment threshold is associated with a motor response. A pain or "maximum" threshold is defined as the level of stimulation which causes pain or severe discomfort to the patient. Lastly, a discomfort threshold is defined as the maximum level of electrical stimulation which the user finds strong enough that it would be too uncomfortable to apply throughout treatment. For stimulation of the SAFN, a therapeutic TENS stimulation intensity is located between the sensation threshold and the pain threshold, and more specifically this should be at least greater than the recruitment threshold and below the discomfort threshold. These thresholds can vary as a function of different stimulus characteristics, and assessment may be done uniquely for different stimulation therapy signals used during treatment.

Figure 10A:
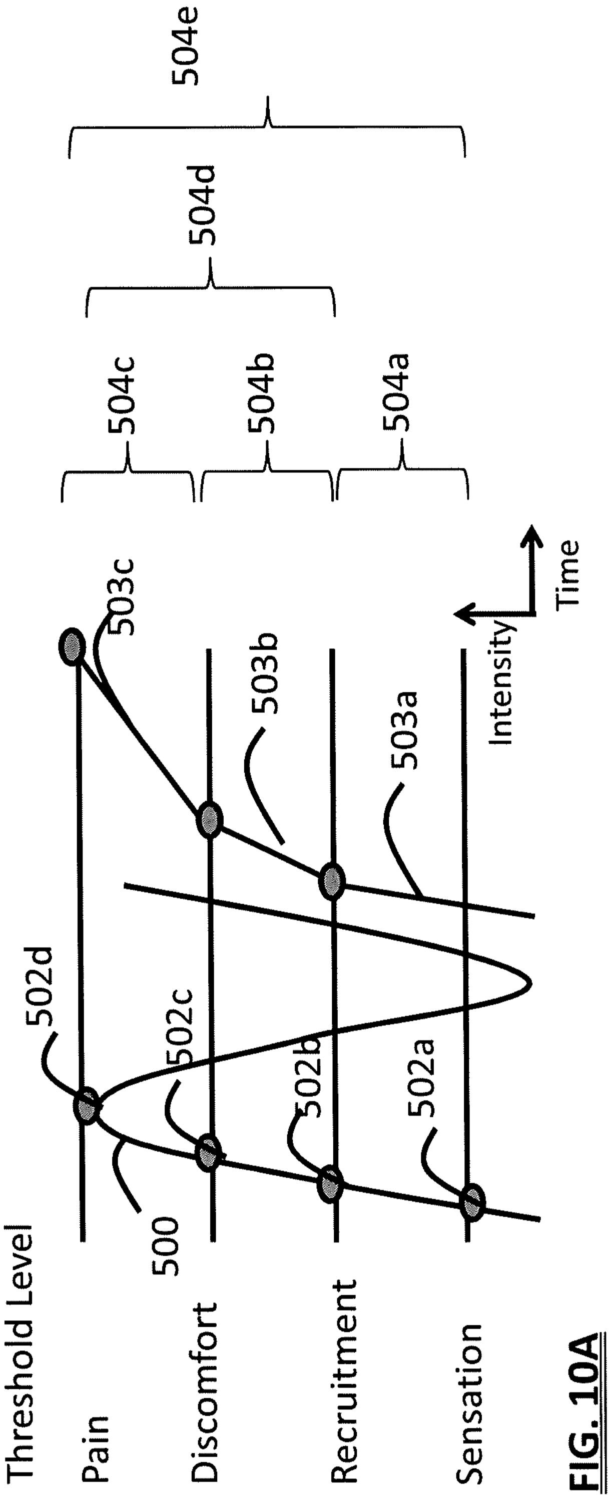
FIG. 10A is graphical diagram providing the relationship of several threshold types and associated ranges which are relied upon during selected methods of stimulation assessment.

As Shown in FIG. 10A, in an embodiment, the system operates to provide an assessment protocol that automatically adjusts stimulus intensity by using a ramping stimuli intensity function 500 (which is sinusoidal, but which can also be linear or exponential) and obtains at least one user input response related to at least 1 of the 4 thresholds, and typically at least 2 of the thresholds. For example, intensity adjustment varies as a function of time and the users provides user input indicating when the thresholds are met. In the figure these threshold levels are shown graphically as 502*a*, 502*b*, 502*c*, and 502*d*. When the user indicates a pain threshold has been reached 502*d*, the stimulation intensity is then decreased. The user can then be asked to indicate thresholds as the intensity decreases from pain towards sensation, or patient input is only prompted for by the user device 32 on the upward slope. These thresholds can also be derived by a user operating the device 12 manually and pressing a button to indicate when a selected threshold such discomfort occurs. In a preferred embodiment, after each assessment trial or at the end of the assessment procedure the external user device 32 will prompt the user to indicate if the assessment occurred correctly and will allow the user to reject the results and redo the assessment.

In an embodiment, therapeutic intensity is set within the range of 504*b*, or greater. Additionally, when using a varying or non-continuous signal, the therapeutic intensity (e.g., amplitude) used during treatment may match or exceed the pain threshold intensity level 502*d* determined for a continuous stimulus since discontinuous stimulation results in less pain. Not to be limited by theory, brief periods of stimulation in which the amplitude briefly exceeds the discomfort or pain threshold of a user may be both tolerable to user and more clinically effective. Using stimulation protocols that define stimuli characterized by bursting, intensity ramping, or modulation can allow larger nerve recruitment for shorter periods. For example, the pulse rate and width are automatically varied in a cyclic pattern of 200 to 600 msec. During the cycle, the amplitude of the waveform can rove or the pulse width is decreased by for example, 10% to 50% from the width defined for the continuous stimulus.

In an embodiment, as the intensity moves into a range normally associated with user discomfort, the rate of intensity growth can be lower 503*b* so that the increase in intensity does not rise too quickly. Accordingly the rise function can be linear, geometric, asymptotic, or discontinuous and multi-sloped 503*a,b,c* where changes in slope occur a predefined intensities or due to user input. In an embodiment the first ramping of the stimulus occurs slowly (e.g. 1 mA per second) and the subsequent ramping occurs faster 2 mA per second, until it is within a value such as 20% of the pain threshold found on a prior trial. In other words, assessment protocols can be adaptive and stepwise.

Figure 10B:
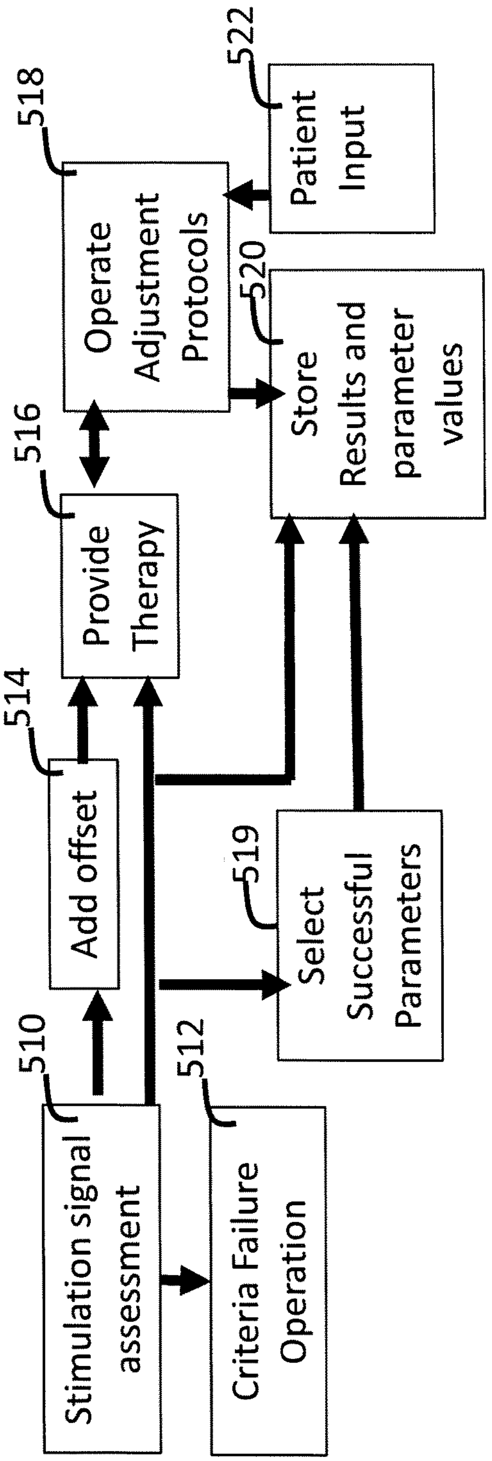
FIG. 10B is an information flow diagram of a method for assessing stimulation signals and operating upon assessment results.

As shown in FIG. 10B, regardless of whether the thresholds are determined using threshold assessment protocols of the system 8 or whether the user indicates one or more thresholds manually, stimulation signal assessment 510 occurs and may lead to several outcomes.

In embodiments, if the stimulation signal assessment protocol indicates any of the following then a criteria failure operation 512 occurs. The user may be instructed to move the position of at least one electrode and repeat the assessment, if for example one of the following occurs: A) If the assessment protocol indicates the difference between the sensation threshold and recruitment threshold is too large, in relation to a criterion using an amount selected from values in a lookup table. B) If the sensation threshold is obtained but the recruitment threshold does not occur before the maximum threshold. C) If the recruitment threshold is obtained and is too close to, or the same as, the maximum threshold (i.e. 504*b* is too small). D) If the difference between two or more of the four thresholds 504*a*, 504*b*, 504*c*, 504*d* are deemed to be too close by the system 8 such as by comparing the difference between thresholds to those found in a lookup table. The look-up table values may be based on the expected differences using population data as reference.

Alternatively, in step 512 which occurs if criteria are not met, the system 8 may programmatically adjust the location of stimulation by adjusting which electrodes from a set of electrodes used during stimulation, or by steering of the electrical stimulation field. Additionally, the user may be instructed to do this according to system prompts or by written instructions. Alternatively, the system may suggest, or patient may be instructed to, adjust a stimulation parameter such as frequency (e.g. from 20 to 10 Hz) or pulse width.

In an embodiment, a therapeutic stimulation intensity that provides therapeutic benefit and is estimated to be comfortable to a user is calculated by incrementing an intensity parameter an offset value 514 above a value determined to be a recruitment threshold intensity value (i.e. minimum value resulting in recruitment) to determine the initial intensity used during therapy 516. For example, the incremental offset level is an amount that is slightly above recruitment threshold such as 15%, increase the likelihood of recruitment (or decrease 15% from discomfort 502*c* or painful threshold 502*d*) If this initial intensity is then decreased by the patient input 522 during the current session, and/or a selected number of times on subsequent therapy sessions, then the treatment level is adjusted to the decremented level that the user selected and the stimulation parameters set for therapy are updated and stored 520. During patient adjustment 518 due to user input 522, the system 8 will warn a patient if they decrease the intensity of stimulation below the level defined as recruitment threshold.

In an embodiment, the system sets the stimulation intensity provided during therapy 516, by incrementing an intensity value 514 above sensation threshold 502*a* with an offset 514 designed to set the intensity above the recruitment threshold level of a user by an amount that is based upon population data, or population normative data that is matched on one or more demographic variables related to the user, or physical or sensed characteristics of the user.

In an embodiment, an assessment procedure 510 can be repeated across a plurality of trials to obtain a statistically based assessment of the intensities associated with at least one of the 4 thresholds shown in FIG. 10A. The mean or median results of the 2 or more trials can be used, while measures of variance (e.g. standard deviation) may serve as important indicators of the variability of a user, and can be used in setting the offset 514. In patients who are more variable in one of their threshold responses, a selected therapy may use a lower stimulation intensity. The user can then increase the therapy based upon their comfort 522 rather than starting with a stimulation setting that is too high. Additionally, the size of adjustments made when a user presses a button to increase or decrease intensity may be adjusted based upon this variability. During the assessment 510 or during an initial interval of the therapy session (e.g., the first 10 second of therapy) if the device's accelerometer module 47 detects a strong tap or stamp by the patient it will immediately pause stimulation to deter patient discomfort.

In an embodiment, an intensity assessment 510 determines an intensity setting that is strong but not painful to a user who is remains in a sitting position. If the user transitions to an active state (walking) then the amplitude may be automatically adjusted 518 so they receive adjusted stimulation 516 while staying active (walking). This latter mode of stimulation could enable SAFN stimulation sessions to last longer than 30 minutes while the stimulation characteristics remain well chosen. A sleeping protocol may use the stimulation intensity set for the sitting protocol to adjust the stimulation 518 to a lower intensity, such as setting intensity to the lowest threshold sufficient to modulate nerve activity 502*b*. When stimulating the PTN, the nerve recruitment threshold 502*b* is defined as the minimum amplitude that causes an evoked motor response. When stimulating a sensory nerve there is no such motor response (unless there is co-stimulation of motor nerves). Accordingly, the SAFN recruitment threshold 502*b* is defined as the lowest stimulation amplitude at which paresthesia that radiates distally away from the stimulation site occurs, or is the lowest amplitude found to evoke a physiological response such as a nerve action potential which can be measured with a recording electrode located proximal or distal to the stimulation site.

In an embodiment, stimulation protocols used for treatment during sleep are initially derived from a user's awake threshold values or other parameter values set for a user's daytime protocol. For example, if recruitment threshold of the user is at a first stimulation level (e.g., 5), and discomfort threshold levels starts at a second level (e.g. 9), and the comfort level used for therapy is between these (e.g. 7), then the sleep protocol uses the first stimulation level (e.g. 5) for the sleeping protocol. The start of stimulation, or adjustment of stimulation, is set to occur after the user has fallen asleep or for a selected sleep stage, using actigraphy or a time delay from when the user provides input to initiate the sleeping therapy session. Adjustment includes increasing stimulation intensity such as to the discomfort threshold (e.g. 7) of the awake protocol, or just below that. Assessment of initial protocol parameters set for the user during sleep includes a method which determines if the increase in intensity causes a user to wakes up (patient input or actigraphy data indicates this interruption). This assessment is repeated at least once more during the night. If intensity increase interrupt sleeps then the device decreases the stimulation level by 1. This process can be repeated until the user sleeps or until the stimulation level goes below the nerve recruitment threshold. In the case where the user is not able to tolerate the stimulation provided even at the recruitment threshold then the device provides notification that the sleep protocol is not suitable. The steps in the assessment procedure are defined in an initial-sleep-stimulation-assessment protocol. This protocol uses a defined protocol or the parameters can be adjusted by a physician.

Pain threshold 502*d* (intensity at which a user feels pain sufficient to be intolerable or very uncomfortable) can be influenced by physiological, electronic (e.g. impedance, electrode contact), psychological, and temporal factors (e.g. can rise as therapy continues). Accordingly, the system 8 can provide assessment 510 that includes a first assessment protocol before a therapy session begins and a second after therapy ends. The information from both assessment procedures is stored and used to set or adjust subsequent treatment. If one or more thresholds assessed at the end of therapy are different than those at the beginning then this information can be used to set or adjust stimulation intensity dynamically during a session (e.g. signal strength can increase in steps from start to end of therapy by 10%). Additionally, if a user increases stimulation intensity after therapy starts 522 then that information can be used to adjust intensity automatically during subsequent therapies in a time dependent fashion since the threshold at which discomfort occurs rises during a therapy session. A machine learning algorithm of the control module 40 may require that a user repeatedly increases the stimulation amplitude during therapy a minimum number of times prior to adoption or proposing the adoption of a time-incremented intensity adjustment in future therapy sessions. Unique assessment protocols can be used during assessment 510 to set stimulation parameter values for treatment protocols used for unique user states (e.g. sleeping, awake, walking, etc).

In an embodiment, each therapy session starts by assessment 510 including stimulating the user at the therapy intensity and then prompting the user to confirm a sensation radiating away from the electrodes down or up their leg. If user input fails to confirm this, then the system operates 512 to provide a stimulus that assists with identifying this sensation. A constant stimulus may be less well suited to allow user confirmation of recruitment than a dynamic stimulus. Accordingly, a protocol that contains intervals with no stimulation or one that varies the stimulation intensity between sensation and discomfort threshold is provided to the patient. If a user still does not confirm recruitment, then the system will instruct the user to move at least one electrode location, or may alter an electrode montage such as location, or polarity. Alternatively, in patients who feel pain during stimulation at intensities necessary to provide nerve recruitment, the system may suggest use of larger electrode pads or additional electrodes of an electrode array can be activated (i.e. the stimulation circuit can adjust to use one cathode and two anodes, rather than 1 anode, since this decreases current density).

In an embodiment, the data obtained during the assessment procedure as well as data related to duration and strengths (and all stimulation parameters) used in the provision of therapy are stored in the system and can be presented in graphical or tabular format.

In an embodiment, the frequency of the stimulation signal is configured to vary between 2 to 30 Hz, or 5 to 20 Hz, or 10 to 20 Hz (with approximately a uniform distribution or otherwise). As the frequency of stimulation varies, the amplitude is adjusted according to the frequency specific pain thresholds (e.g. 502*d*) that were determined during an assessment procedure 510. For example, assessment may be performed separately for frequencies that differ by 5, 10, 20, or more. In an embodiment, both 10 and 20 Hz are assessed in step 510 for amplitude associated with pain threshold. If one setting exhibits a pain threshold is larger (e.g. at least 2 "intensity units") than that frequency is selected and stored 520 to be used for therapy. The difference between recruitment threshold and pain threshold 504*d* can also be used to select the frequency used during stimulation.

As a session progresses, the stimulation thresholds may change with 'electrode settling". If a user increases or decreases stimulation amplitude during a portion of the therapy session and maintains this for the remainder, then this value is stored 520 and used during the subsequent therapy, or the system 8 prompts the user part way through therapy to assess if stimulation can be increased to this value. If the user confirms this is comfortable, then the system 8 can incorporate this inter-session increase in intensity.

In an embodiment, the method for determining a therapy stimulation amplitude includes applying electrical stimulation to the user at a first stimulation intensity, automatically increasing the intensity of the electrical stimulation applied to the user from the first stimulation intensity to a second intensity at which the electrotactile sensation threshold is identified by the user and increasing the intensity of the electrical stimulation applied to the user from the second stimulation intensity to a third intensity at which the electrotactile pain or discomfort threshold is identified by the user. The user will perform this procedure between 1 and 3 times. The method further including calculating a therapeutic stimulation intensity from at least one of the second and third intensity level or statistics computed thereupon. The method can be implemented as a therapy assessment program 510 implemented under the control of the control module 40. In an embodiment, the device is calibrated to the user's sensation threshold and/or discomfort threshold by an algorithm using at least ascending or descending method of limits. Since this may be different for left and right leg, the assessment 510 can be done for each leg and different results are stored 520 and used for each leg under control of the leg status module 64.

Stimulation at an intensity below the level of recruitment perception may not provide sufficient treatment of OAB, and the degree of therapy may be associated with the stimulation intensity and treatment session duration. Percutaneous stimulation of the posterior tibial nerve typically is provided at an intensity that feels "strong but comfortable" to the user, and this may also be the case for stimulation of the SAFN. The stimulation pulse characteristics should be sufficient to exceed the rheobase of the target nerve, in other words stimulation should exceed the nerve activation threshold.

Figure 10C:
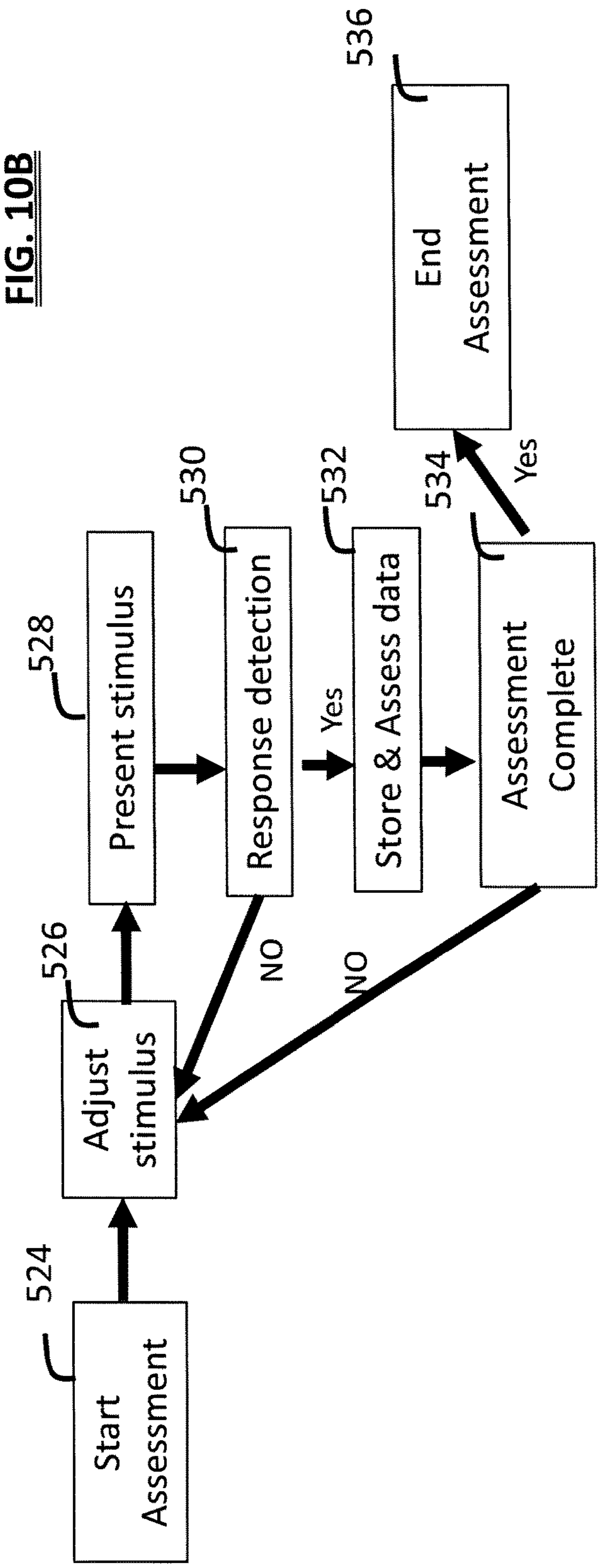
FIG. 10C is an information flow diagram of a method for assessing stimulation signals.

FIG. 10C shows an embodiment of the step of performing stimulation signal assessment 510 shown in FIG. 10B, and the stimulus adjustment functions depicted in FIG. 10A. In step 524 the assessment is started using an assessment protocol selected by a user, doctor, or by the device 12. The assessment protocol may dictate how many estimates for one or more thresholds should be obtained during the assessment and also includes assessment criteria such as how variable the threshold results can be with respect to one or more thresholds being assessed. For example the assessment protocol may dictate that the stimulus should be "ramped" repeatedly 2 or 3 times during the assessment, where a "ramp" is defined as the stimulus moving from a level below sensation threshold to at least one of the threshold levels shown if FIG. 10A. Additionally, the protocol may dictate that the intensity associated with nerve recruitment threshold should not differ by more than a 10% range, and if so the assessment should be repeated a fourth time. In step 526 the stimulus parameters are adjusted according to the assessment protocol. In step 528 the stimulus is presented to the user and in step 530 the response of the user is sensed or otherwise obtained. If the response is not detected the method returns to step 526 and the stimulus is adjusted according to the assessment protocol in the absence of a user response. For example, user input can be provided using the screen shown in FIG. 12A. If a response is detected the method moves to step 532 where the data about the response (e.g. the user input about the stimulation, the stimulus characteristics associated with the input). In step 532 summary statistics can be determined such as the mean or standard deviation of at least one threshold level that is being determined as a function of the assessment. If the assessment is determined to be incomplete in step 534, then step 526 is repeated with the stimulus adjustment occurring according to the assessment protocol (e.g., increasing to the maximum defined intensity of the assessment stimulus or starting below the sensation stimulus again). If the assessment is determined to be complete in step 534 (e.g., the selected number of stimulus assessment repetitions has occurred and the range of the nerve recruitment threshold is below the specified amount) then the assessment ends 536 and the assessment has the status of "successful". In the case of a success status, the assessment algorithm may also determine the therapeutic parameter values to use during treatment. If the assessment is determined to be complete in step 534 (e.g., (e.g., the selected number of stimulus assessment repetitions has occurred and the range of the nerve recruitment threshold failed to be below the specified amount) then the assessment ends 536 and the assessment has the status of "Failed". In embodiments, the assessment only assesses 1 or 2 of the sensation, recruitment, discomfort, and pain thresholds. Further, in the step of response detection 530 the user input can include a command to pause, halt, or exit the assessment.

In an embodiment, the method shown in FIG. 10C is used for determining characteristics of a treatment protocol for providing transcutaneous electrical nerve stimulation of a target nerve. The assessment method comprising the steps of operating a processor of a control module 40 to apply transcutaneous electrical nerve stimulation 528 to a user using a first set of stimulation parameter values that are set in step 526 and which are selected to create as stimulation signal that is below a user's sensory threshold. The method includes sensing a response such as user input 540 and automatically adjusting a characteristic of the stimulation waveform 526 until a nerve recruitment threshold is identified by the detection of user input response 530. If defined by the assessment protocol implemented by the method, the method continues 534 by automatically continuing to adjust a characteristic of the stimulation waveform until a discomfort threshold is identified; and then automatically continue 534 to adjust a characteristic of the stimulation waveform until a pain threshold is identified; and determining the therapeutic parameter values using those associated with the nerve recruitment threshold and at least one other thresholds when selecting or adjusting at least one stimulation protocol to be used during treatment.

Initial Setup and Electrode Calibration.

Figure 11A:
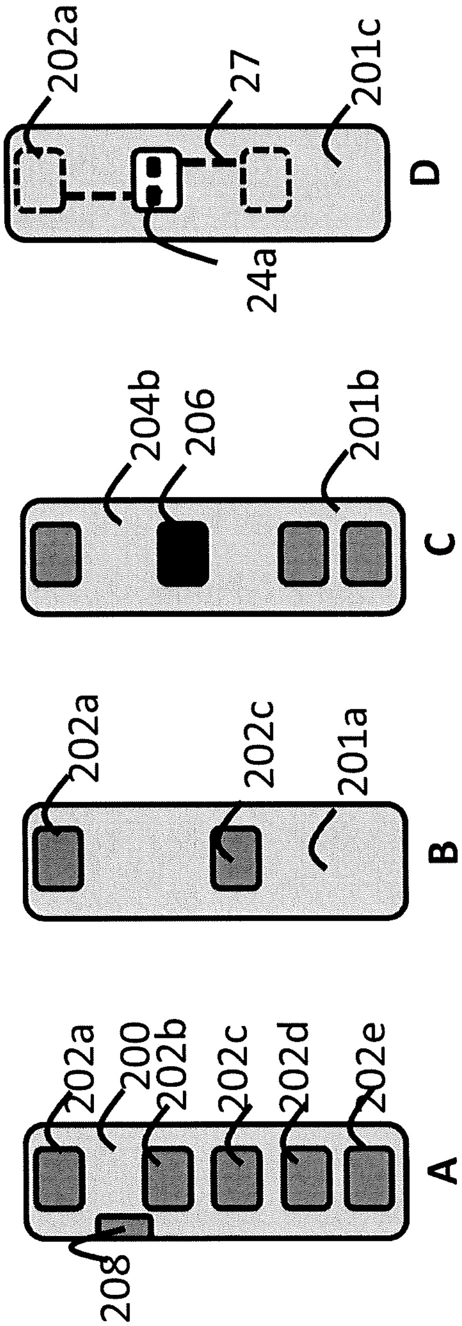
FIG. 11A illustrates four schematic views of electrode arrays used for assessment and treatment.

As shown in FIG. 11A, in an embodiment, 3 or more electrode pads 202*a-e* disposed on an array 200 and used to determine spacing for the electrode array. The array can be configured to work with a stimulation device or a stimulation assessment device 220 that connects to a control port 208 on the array or to the port 24*a* typically occupied by the device 12 during treatment. For example, during an assessment protocol 510 a user iteratively selects electrode pairs so that stimulation pads 202*a* and 202*b*, or #202*a* and #202*c*, or #202*a* and #202*d* or 202*e* are assessed. By selecting electrode pairs with greater inter-electrode distances, larger stimulation fields are assessed. If none of the pairs produce suitable stimulation of the target nerve, then additional combinations electrode pair can be assessed which adjust the vertical distribution of the stimulation field such as using stimulation pads #202*b* and #202*e* which moves the field lower on the leg. The user can perform the assessment manually or the device can provide different combinations to the user according to an algorithm. The device displays information about the electrode montage as it is adjusted so that the user knows what combinations were most successful. The user may use the user device 32 to indicate which combinations of stimulation were successful or preferred. In an embodiment, the system 8 allows the user or protocol to select electrode combinations with a first set of multiple electrode pads #202*d* and #202*e*, both provide the same signal (e.g. cathode) that is opposite to the signal applied at a second set of 1 or more electrodes (e.g. anode). Switching anode and cathode designations (polarity) is also allowed. When using biphasic stimulation pulses output by channels of the signal generator, these can be selectably routed to either the first or second pair.

In an embodiment, the assessment uses electrode array 200, which contains a plurality of electrodes 202 such as 5 which are used during an initial assessment 510 by a user. As shown in the electrode array 201*a*, labeled type "B", if assessment 510 indicates electrode pads 202*a* and 202*c* provided a suitable nerve recruitment, an electrode array type "B" is used during therapy having the corresponding inter-electrode spacing. The bottom surface can be comprised of non-conductive adhesive so that the electrode sticks to the user's skin across its entire bottom surface but only stimulates from a the pads 202*a,c* where the gel is conductive. As the distance between the electrode pads is increased the field may increase which may entrain a larger number of SAFN branches.

If the user experienced better recruitment using electrode pad 202*a* referenced to 202*d* and 202*e*, then type "C" array is used (the two pads 202*d* and 202*e* operated as a "single" pad). When inter-electrode distances are above a selected amount, the array 201*b* is configured with 206 adhesion pads to facilitate good adhesiveness with the user. Adhesion pads 206 only serve to increase skin-electrode coupling and are not configured to provide electrical stimulation. The type "D" array shows the top side of the array 201*c*, which is made of a non-conductive substrate that is configured with a first connector port 24*a* having contacts for receiving signals from a connector port 24*b* of a device 8*a* and conduits 27 for connection with a stimulation pads 202*a* on the user-side of the array 201*c*.

The non-conductive backlayer of the array 201*b* may be created from rubbers, cellulose-based materials, silicon-based products, polymers, neoprene, polyethylene, ethyl vinyl acetate, polypropylene, polyimide, polyester, polyethylene terephthalate, polyaryletheretherketone, polytetrafluoroethylene, polyethylene naphthalate, co-polymer plastics, as is well known. The non-conductive backlayer may also include materials such as foams or padding for comfort or for retaining shape. The electrodes may also be realized as part of a band or sock which is worn by a user and may be used as "dry" electrodes or with conductive paste/gel commonly used for TENS application.

The assessment procedure 510 may provide an assessment outcome operation which is to select the model ID for the electrode array and may automatically select and store 520 this type for use with shopping cart module 66 of the system 8 such as when the user device 32 is realized using software application of a user's smartphone. In addition to electrode configuration, electrode adhesion can alter treatment success. If an electrode array disconnects from a user more than a certain number of times per day or week during the provision of therapy the on-user module 49 may prompt the user to adjust the next order of the shopping cart module 66 to adjust to an electrode model type with greater adhesion or more adhesion pads. The system 8 may also prompt the user about whether the adhesion is sufficient or if they would like to try using an array with greater adhesion as part of the survey module 62.

Figure 11B:
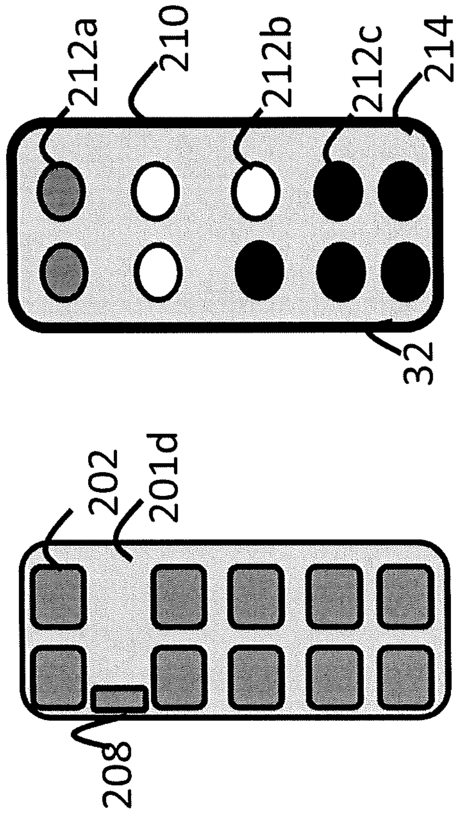
FIG. 11B is a schematic view of an electrode array and a user controller screen.

As shown in FIG. 11B, in an embodiment the assessment array 201*d* has two or more rows of stimulation pads. The shape of the assessment array 201*d* does not have to be rectangular, and the inter-pad distances, sizes, number and shapes of the electrode pads can vary greatly from that shown in this example embodiment without departing from the scope of the invention. A user device 32 is configured to control either a device 12 or an assessment device 220 in order to control the electrode pads 202 that are used during stimulation. For example, under control of the control module 40 implementing an assessment protocol 510, the user operates using virtual buttons 212 of the display screen 214 of the device 32 to select which electrodes are serving as anode or cathode. By pressing a virtual button once it is designated an anode 212*a*, tapping again causes the virtual control to indicate the corresponding electrode is not used during stimulation 212*b*, while tapping again will designate it as a cathode 212*c*. Rather than using display to present the user with virtual buttons, the user device 32 can be realized using a specialized device with physical controls.

Figure 12B:
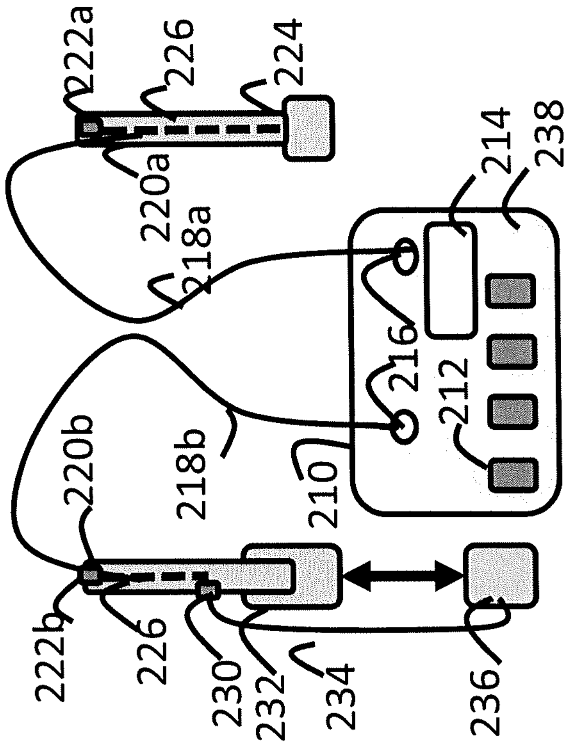
FIG. 12B is a schematic view of a stimulation assessment device to evaluate parameters and sites.
Figure 12A:
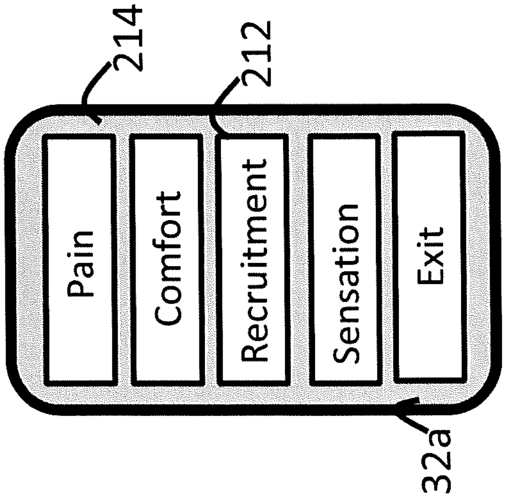
FIG. 12A is a schematic view of an alternative user controller screen.

As shown in FIG. 12A, in an embodiment, a second user device 32*a* has virtual buttons 212 presented on a display screen 214. When a doctor uses the first user device 32 to change the stimulation parameters, a patient may use a second user device 32*a* to provide patient input, such as can occur during assessment 510. In this example, the patient selects a virtual button indicating a threshold related to either pain, discomfort, recruitment, or sensation (at the stimulation site).

Using a second stimulation site may allow the stimulation to occur at a higher stimulation amplitude and also without pain, relative to a first stimulation site. In the case where the threshold for sensation is 3 and pain begins at 5, has the same sensation-to-pain difference 504*e* as a stimulation site where the threshold is at 5 and the pain begins at 7. The site that produces the largest sensation for the user at the peak intensity may be selected as the best combination, since the range of the two sites are the same. However, stimulation site where the threshold begins at 3 and pain begins at 9 may be better than one where the pain begins at 5 since the sensation-to-pain difference 504*e* has a larger range of 6 rather than 2. Alternatively, the criteria for selecting stimulation sites may be applied using the range between recruitment and pain 504*d* between recruitment and discomfort ranges 504*b*. The ranges can be assessed by having a user provide input on the second user device 32*a* while the system provides assessment waveform intensities 500 to indicate thresholds 502*a*-502*d* as part of stimulation signal assessment 510. After a site is selected, an appropriate model of an electrode array can be used that corresponds to a successful combination of stimulation sites.

As shown in FIG. 12B, in an embodiment, of an electrode site stimulation assessment device 210 having controls 212 that allow the user to select and adjust the stimulation signal protocols including adjustment of pulse width, pulse shape, polarity, monophasic/biphasic, symmetrical, asymmetrical, frequency and amplitude of the stimulus waveform. A display 214 shows information about the waveform being applied. The assessment device 210 has circuitry, software, memory, processors, amplifiers, power regulation, and signal conditioning circuitry needed to provide its functionality and incorporates all of the modules disclosed in FIG. 2 for the device 12. Rather than containing the display and controls on its housing 238, it can be configured to be operated from the user device 32, and can also communicate with the second user device 32*a*. The 216 connection ports allow for connection to plugs of first and second conduits 218*a*, 218*b*. The first conduit carries the stimulation signal from a port 216 to a plug 222*a* of a first handle 220*a* which is made of a non-conductive material and has a connector port 222*a* for receiving the conduit and transmitting the signal along conduit 226 to a base section 224 that serves as a stimulator. The base section is realized as a conductive element and may be realized in the form of a flat metallic pad or a ball-stimulator that rolls across the user's skin and delivers the electrical signal.

The second handle 220*b* communicates the stimulation signal from the plug 222*b* along the conduit 226 to a connector port 230 that receives the plug on one end of a lead 234 the other end of which is connected to a conventional TENS pad 236 (which is realized without adhesive on the conductive surface that contacts the skin of the patients leg 10). The TENS pad is configured with an adhesive gel on its top surface so that it may be attached to the base member 232 (or may be attached using other fastening means such as a snap-type connector that operates with a complementary connector on the base section 236). During operation the user positions the two handles 220*a*, 220*b* to assess different stimulation sites on the user's leg. In the case of the SAFN nerve the user may operate device 32*a* to provide feedback that is recorded by the system 8 or may verbally indicate when a particular threshold is reached. Pre-programmed stimulation subroutines can be implemented wherein the amplitude of the waveform is repeatedly ramped, and the assessment device may provide auditory cues such as tones at the beginning of each stimulus ramp when the intensity is lowest. In the case of stimulation of the PTN, at least one of the two handles can be positioned to stimulate the PTN, and the threshold for a motor response is associated with recruitment threshold for that stimulation site. The assessment device 210 can also be used to assess candidate sites for implantation of a device by stimulating an adjacent skin surface.

Figure 13:
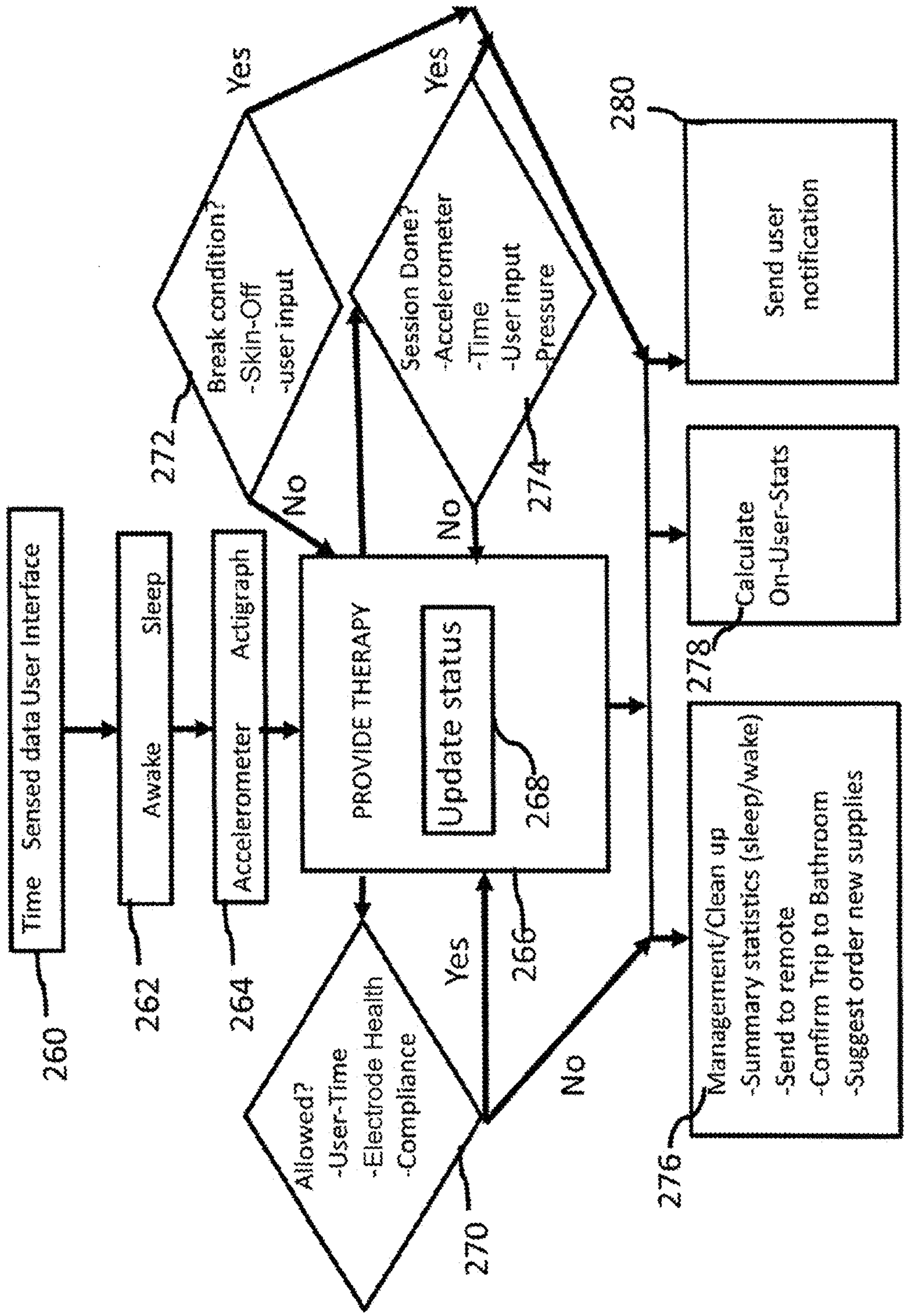
FIG. 13 is an informational flow diagram of a method for providing stimulation therapy.

As shown in FIG. 13, in an embodiment, a method of providing stimulation treatment with the system 8 includes, operating upon a therapy initiation trigger 260 to determine that a new therapy session should occur such as determining the date and clock time corresponding to a scheduled treatment, user input, or sensed data. The next step includes protocol selection 262 such as sleeping, awake, induction, maintenance, etc. The next step is the assessment of patient state 264 sensed data such as an accelerometer to provide actigraphy, and determining patient activity, state, and body position in order to further select or adjust the treatment protocol. In the next step the system 8 provides therapy 266 according to a therapy regimen of the control module 40. Periodically, or continuously, the system performs the step of updating status 268, which can entail for example, detection of an event-bathroom trip, change to a user's body position-standing up, or change in activity level-sleeping. This step includes performing steps such as determining if therapy allowed 270, determining if a break condition is detected 272, or determining if a session termination definition or condition is met 274 (which may also be a stimulation pause condition that causes the stimulation to be temporarily paused). If the rules implemented by the logic and algorithms of modules 270, 272, and 274 indicate that stimulation should continue, then step 266 is repeated, otherwise the operation is passed to steps which include management/clean-up 276 (e.g., computing summary statistics, sending data to remote computer, new supplies, survey user about events), calculating and updating the on-user statistics 278, and/or sending notification to user 280. Following steps 276, 278, or 280, the system may return to step 266 and stimulation is restarted if the condition that caused the stimulation to halt or pause changes status, if the user restarts stimulation or begins another session 260, or otherwise.

Kits and Instructions

Figure 14A:
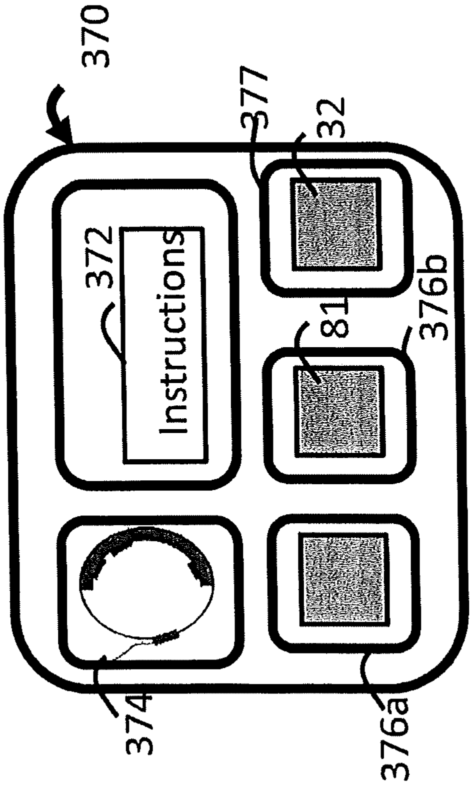
FIG. 14A is a schematic view of a TENS kit.

As shown in FIG. 14A, in an embodiment the system may be embodied as the provision of a kit 370 having a device compartment 374 configured for a stimulation device 12 with or without an electrode array 16; a first accessory compartment 376*a* configured for containing accessories 81 such as USB charger, an electrode array, a vibrator system component, a conventional TENS electrode that is configured to be attached to the system, etc; a second accessory compartment 376*b* containing an accessory 81 which may be a moisture sensor; a user device compartment 377 that contains a user device 32 such as a remote control that controls and communicates with the device 12 and at least one a remote computer 80; and, a compartment for holding instructions 372 such as a booklet, or a DVD or USB Flash memory key with instructions, instructional videos, etc. In embodiments, the instructions 372 are realized using different media. The instructions 372 may be physically present in a kit containing other system components, but can also be supplied separately. The instructions 372 can be embodied in separate instruction manuals, or in video or audio tapes, CD's, and DVD's. The instructions 372 for use can also be available through digitally realized instruction manuals and in content made available on a website, and provided on sites such as shopping, blog sites, company website, or product review websites.

Instructions 372 may instruct on the use of TENS, percutaneous, or implantable devices in treatment of OAB by using SAFN stimulation. Instructions can direct the use of system and method for the placement of at least one stimulator (e.g., electrode) for providing stimulation to the SAFN and its branches. Most typically slightly above or below the level of the patella, although other locations between the waist and foot are also viable. The instructions can provide for improved recruitment of the SAFN target, and therapeutic benefit by the placement of one or more leads or portion of the system such as an electrode array. The instructions can direct a user to use an assessment stimulation protocol which provides a non-constant (e.g., increases the stimulation intensity above, and then returns to, a sensation threshold of a user) stimulation during assessment or to allow the system to do so using an assessment protocol that includes step 510 which ramps intensity or adjusts other stimulation parameters. Using stimulation parameters which are designed to recruit a nerve, followed by parameters that do not recruit the nerve, allows a user to more easily discern whether they can confirm SAFN recruitment such as sensing paresthesia radiating away from (or distinct from) at least one of the electrode sites. In the leg, the radiation may reach a more distal area in the leg, such as the ankle, foot, or toes. A stimulation level at or above a first noticeable sensory threshold, or recruitment threshold, and/or below a discomfort stimulation level, can be described to users to aid them determining desired stimulation parameters of therapy.

The instructions 372 for use includes instructions for placing a lead, a stimulation pad, or an array to assess or successfully recruit a nerve such as the SAFN. These may also include methods of assessing or adjusting the location of at least one electrode to modulate the SAFN in the treatment of OAB (or other fecal or urinary disorder or symptom related to, for example, incontinence, urgency, or voiding frequency). The instructions include steps for setting and/or adjusting stimulation parameter values. The instructions may include information on recognition of sensations or stimulation threshold levels. For example, a first stimulation threshold level may be for recognizing a first type threshold related to sensation of stimulation, or a second for recognizing a stimulation level associated with recruitment of the SAFN. The instructions may also disclose how to use the system to measure treatment response, create a stimulation schedule, set reminder alarms, or track therapy progress. The instructions may include website addresses, videos, or features of mobile apps, that allow individuals to provide feedback on the therapy, respond to questions, and provide other input related to symptoms or user satisfaction.

Figure 14B:
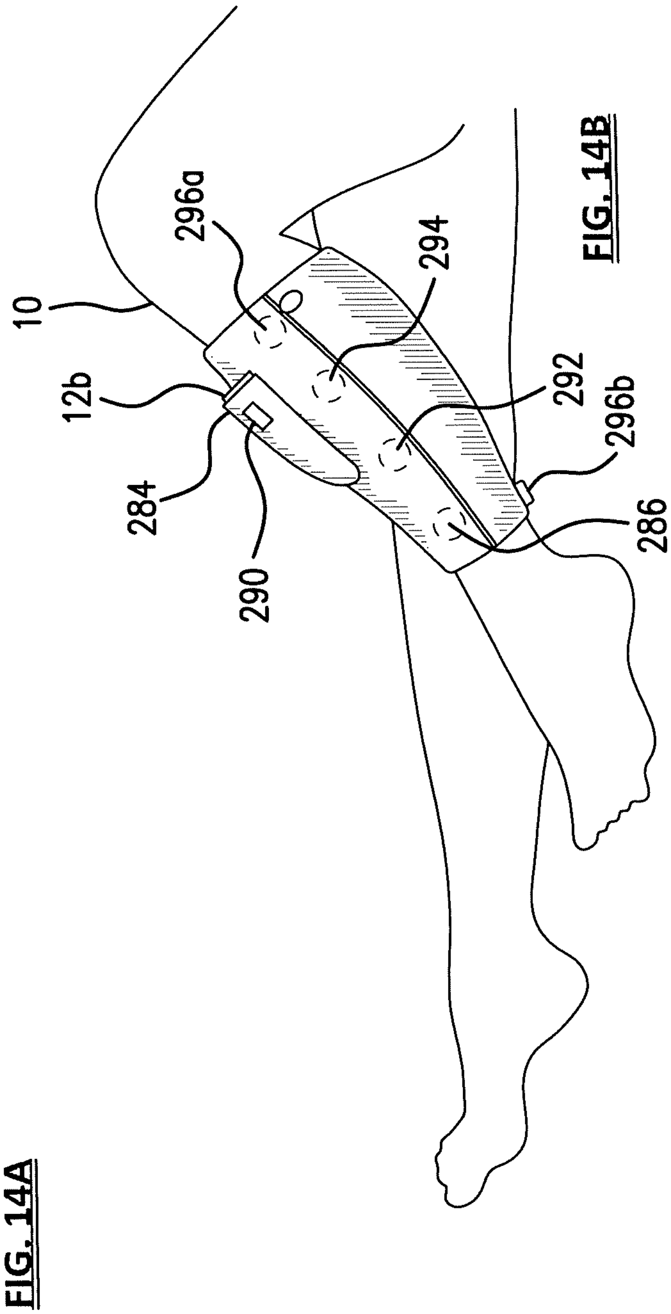
FIG. 14B is a illustrates a wearable stimulation system on a user's leg.

As shown in FIG. 14B, in an embodiment the system 8 is realized having a device 12*b* with a form factor similar to a portable MP3 player with a display and user controls (that may be disposed on the top surface that is not covered by the pocket 284 that is formed in a leg garment 286. The leg garment may be formed of a material used with compression leg sleeves to deliver a controlled amount of pressure in specific regions which can cause the stimulation electrode to be biased more tightly against a target nerve. This may assist in users with edema. The graduated compression patterns should allow for circulation, and the material should enable wicking moisture away from the skin and promote anti-microbial/anti-fungal effects to deter odor (microfiber nylon, or nylon/lycra blend) and/or maintain cleanliness. The sleeve is shaped-to-fit the intended area on which it will be worn. Additionally, the sleeve may be fitted with a cuff that can be inflated to increase the bias of one or more stimulation pads against the skin in order to move the stimulation closer to the target nerve. An aperture 290 allows the user to view the display or controls of the device 12*b*. A fastening means 292 such as Velcro™ allows the user to fasten or adjust the sleeve size and at least one fastener 294 may serve to lock the sleeve in a closed position. The illustrated sleeve shows a set of electrodes 296*a* oriented in a lateral fashion anterior to the midline (which would approximately align with the illustrated contour of the fasting means 286) to stimulate nerves in the leg such as the sural nerve, and a single electrode 296*b* that is posterior to the midline and most distal, which may stimulate, for example, the PTN. When used to stimulate the SAFN the set of electrodes 296*a* would be disposed on the medial aspect of the leg and anterior to the midline. The electrodes 286*a,b* are incorporated into one or more electrode arrays that reside on the inside of the sleeve 286 and communicate with the device 12*b* via conduits in the sleeve (not shown), or can be formed of dry electrodes, or realized in other manners as is well known. The locations of the electrodes may also be customized based upon an assessment 510.

In an embodiment, the leg garment 286 and/or electrode array is configured so that the device can be attached to calves of different sizes by user adjustment or can be selected from a group of different sizes to fit varying size calves. The band includes visual indication means to measure calf circumference, such as a ruler with markings printed on its surface. At least one characteristic of the stimulation protocol is modified according to user data input about calf circumference.

Rather than using a band, or leg garment the device can have an adhesive on the bottom surface of its housing, for removably securing the device to a user's leg. In an embodiment, the device is realized as a pad with a bottom surface having 2 electrodes that are spaced and configured for stimulation of the SAFN. In a disposable embodiment of the device, the device may approximate the look of a large Band-Aid and may be controlled through 2 or 3 buttons (off/on, increase intensity, decrease intensity) or by a user device 32. The device may be configured to be used for 2-10 times and disposed monthly. The user obtains a new device which may be paired with a user device 32 to exchange information related to usage, compliance, and/or stimulation parameters. While a more sophisticated device is good for long term use, a user may wish to have this relatively simpler device when travelling or for other reasons. The device can be configured to generate pulses of pulse width 0.01-3 msec between 1-100 V and 1-100 mA, at frequency that varies between 10 and 20 Hz. When the device is turned on it may provide a hard coded treatment protocol and the user simply adjusts intensity. The electrodes of the device may have an inter-electrode spacing of at least 1 mm or 1 inch, and preferably about 2 to 4 inches, and the signal is provided by a signal generator configured to stimulate at between 10 and 20 Hz.

Implantable Device Designs

Figure 15A:
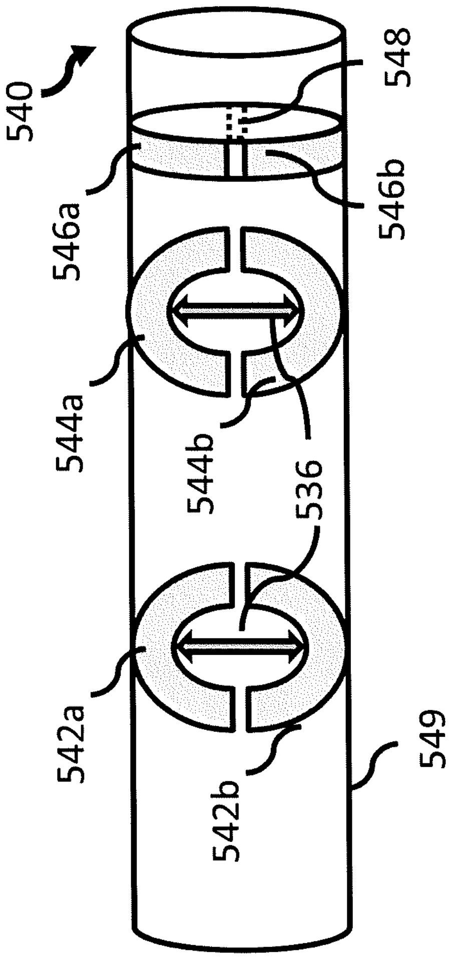
FIG. 15A is a schematic view of an implantable neurostimulator in a non-deployed state.
Figure 15B:
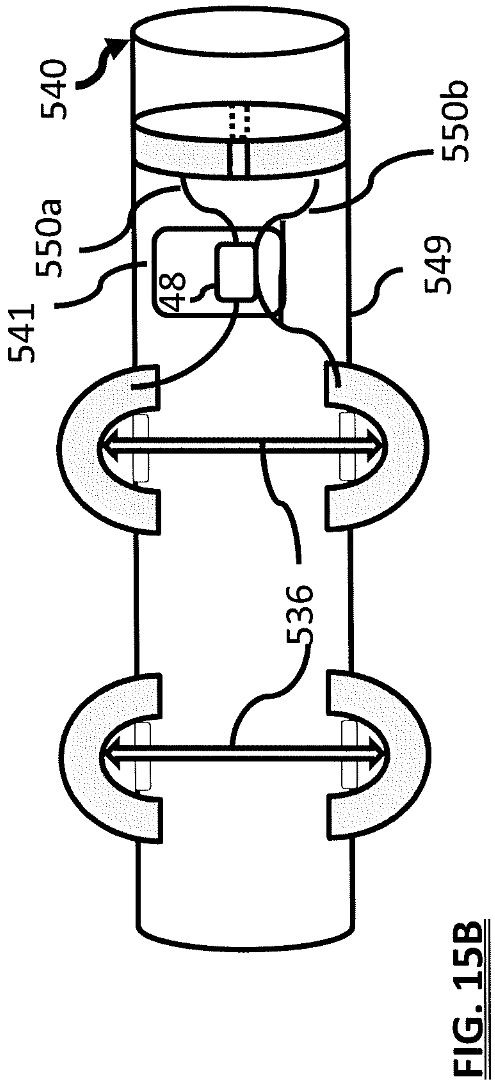
FIG. 15B is a schematic view of an implantable neurostimulator in a deployed state.

In an embodiment shown in FIG. 15A, an implantable device 540 is shown having a first anchor realized by a first portion 542*a* and second portion 542*b* which are biased to be pushed outwardly from the center of the neurostimulator through the housing 549 by a spring 536. Additional anchors can be provided within the neurostimulator 540, such as a second anchor realized by portions 544*a*, 544*b*, and spring 536. Additionally, the stimulator has at least one circumferential electrode 546 which may be formed into two or more stimulator surfaces 546*a*,546*b* using diametrically situated non-conductive gaps 548, to form an anode and cathode or to provide a circuit for delivering biploar stimulation pulses. FIG. 15B shows the neurostimulator in a deployed state with the anchor mechanisms 542*a-b* and 544*a-b* extended outward by their springs 536. When the anchors 542*a-b*, and 544 *a-b* are metallic or otherwise conductive, or have electrode surfaces disposed on their surface, these can also serve as electrode contacts and can be connected to a programmable stimulus generator which is part of the simulation module 48 that part of and under control of the implantable device control and stimulation module 541 (which contains the circuitry, power, memory, clocks, routing and communication circuitry, and other components well known to be used in implantable micro-neurostimulators) by conduits such as the conduits 550*a*, 550*b* which connect the module 48 to the stimulator surfaces 546*a*,546*b*.

Figure 16:
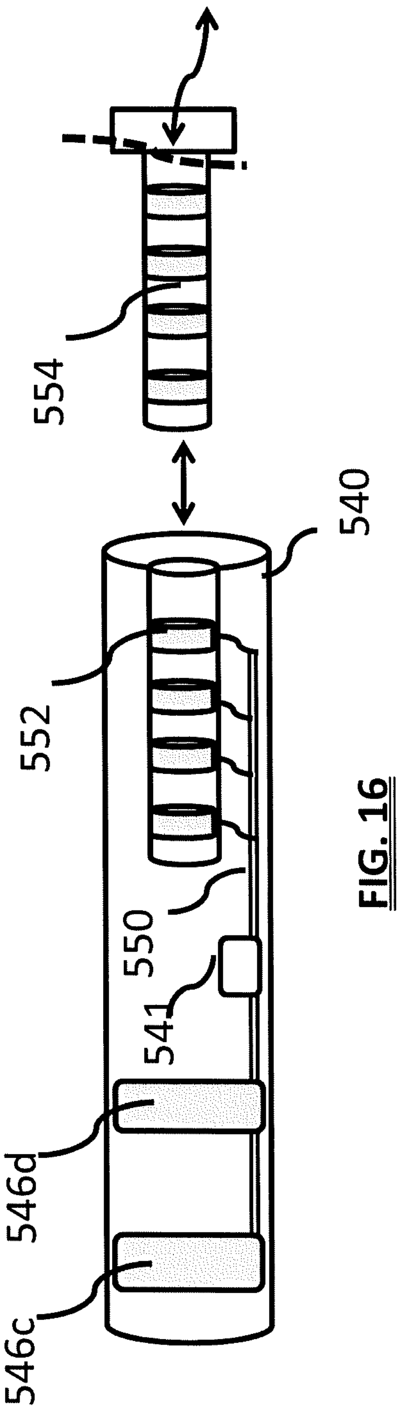
FIG. 16 is a schematic view of an alternative embodiment of an implantable neurostimulator and a lead.

In an embodiment, as shown in FIG. 16 a neurostimulator 540 has a first circumferential electrode 546*c* and second circumferential electrode 546*d* and a stimulus generator module 44 and a conduit 550 for communicating the stimulation signals from the implantable device control and stimulation module 541 to the electrodes 546*c-d* and to contacts of an IS1 or IS4 connector 552 which is configured for securing a stimulation electrode having an IS1 or IS4 connector 554. The implantable neurostimulator can stimulate along its length and/or be connected to flexible leads having different lengths for different applications. This flexibility obviates the need for neurostimulators having housings of various lengths for different applications. For example, the neurostimulator 540 can reside in an area under the knee and be connected to a lead that terminates in a portion having lead contacts which resides 3-6 inches lower in the leg.

Figure 17:
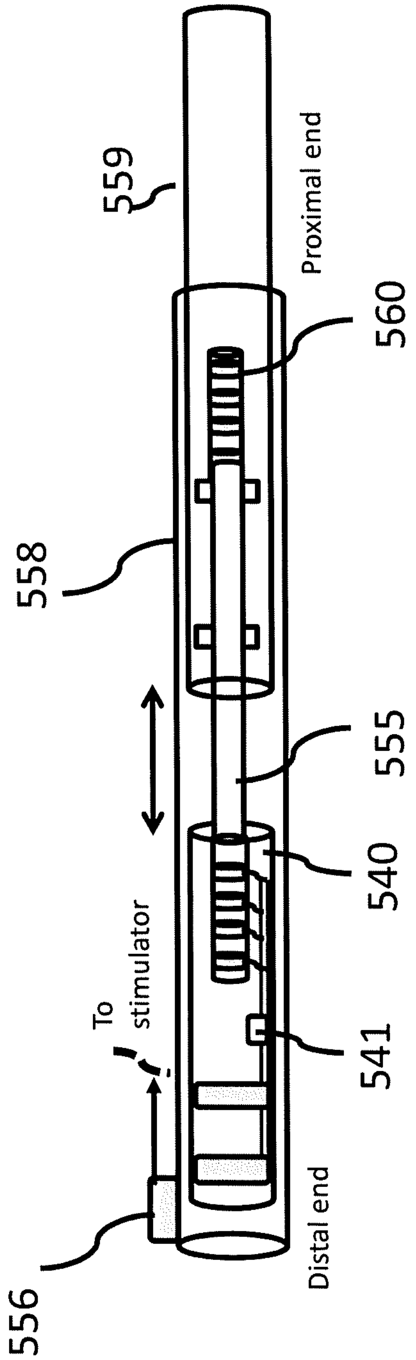
FIG. 17 is a schematic view of an implantable neurostimulator and a lead disposed within an introducer.

In an embodiment shown in FIG. 17 a neurostimulator 540 is shown residing in a delivery tube 558 that is part of an introducer tool for injecting neurostimulator into a patient. The introducer tool can have an electrode contact 556 that is electrically connected to stimulation circuitry of a stimulation test device (not shown) and which can stimulate the patient during implantation to assess candidate locations. The introducer tool may be configured to allow the neurostimulator to stimulate candidate tissue during implantation. In the embodiment shown an electrode 555 having an IS4 connector on one side for connection to the stimulator 540 and electrode contacts 560 on the opposite end is shown within the delivery tube 558. The neurostimulator 540 and the electrode 555 are both deployed into the patient by a surgeon using inner tube 559 and pushing the neurostimulator out of the distal end of the outer tube 558 and into the patient. Upon exiting the delivery tube 558, the first and second anchors will decrease migration of the neurostimulator 540.

Figure 18:
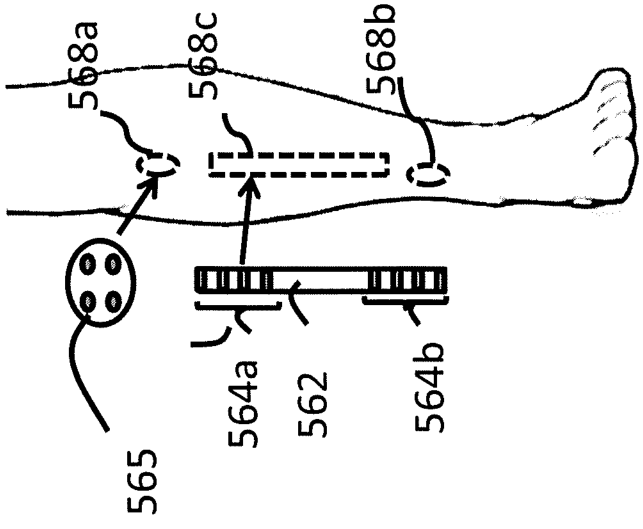
FIG. 18 is a schematic view of two neurostimulators and candidate implant sites on a patient's leg.

FIG. 18 shows embodiments of implantable neurostimulators, such as a neurostimulator 562 with at least a first set 564*a* of 2 or more electrode contacts and a second set 564*b* of 2 or more electrode contacts. When both a first set 564*a* and second set 564*b* of electrode contacts are used then each set may have a single contact. When only a first set of contacts is provided then the neurostimulator 562 can be implanted so that the set situated about 1-2 inches below the knee. When the second set 564*b* is also provided, then these may be located 3-4 inches below the first set of contacts 564*a* and operate with the first set to increase the size of the stimulation field and recruit more SAFN fibers. When the neurostimulator 562 is configured to work with a conduit as shown in FIG. 16, then second set of contacts 564*b* can be implanted near the patient's medial malleolus and deep to the tissue to stimulate the PTN or more superficially (and typically more proximal and/or anteriorly located) to stimulate the SAFN. When stimulating the SAFN or PTN, the surgeon may first assess candidate stimulation sites by mapping areas using either TENS or percutaneous stimulation, such as disclosed in FIGS. 10*a*-12*d*. The surgeon selected target sites that meet criteria such as where lower recruitment thresholds are found as evidenced by evoked sensory or motor response, or where evoked potentials are sensed.

A perifemoral location such as 4 cm below the inguinal crease and 0.5 cm lateral to the femoral artery (at a depth of about 2-4 cm) can be used to sense the evoked responses to stimulation at or below the knee. The nerve to the vastus medialis muscle runs alongside the SAFN and stimulating that can serve to help locate the SAFN which is only a sensory nerve because it will cause contraction of the medial aspect of the thigh and movement of the patella.

Alternatively, a coin shaped neurostimulator 565 can be implanted below or above the knee. When implanting above the knee it may be better to access the SAFN from the back of the leg, or alternatively a medial location is used where the infrapatellar branches are accessible. In the figure the round neurostimulator 565 is shown with implanted candidate locations of 568*a* which is about 1 to 4 inches below the patella and in the medial-anterior aspect of the leg, and 568*b* which is a site near the medial malleolus, and typically higher and more anterior in the leg. The position for neurostimulator 562 is shown as a site 568*c* that extends along the medial anterior portion of the leg. Regardless of candidate implantation regions, the actual target implantation/stimulation site should be determined by meeting criteria associated with successful treatment, and stimulation should be assessed at the site prior to implantation to ensure that a sensory or motor evoked response is obtained.

Figure 20:
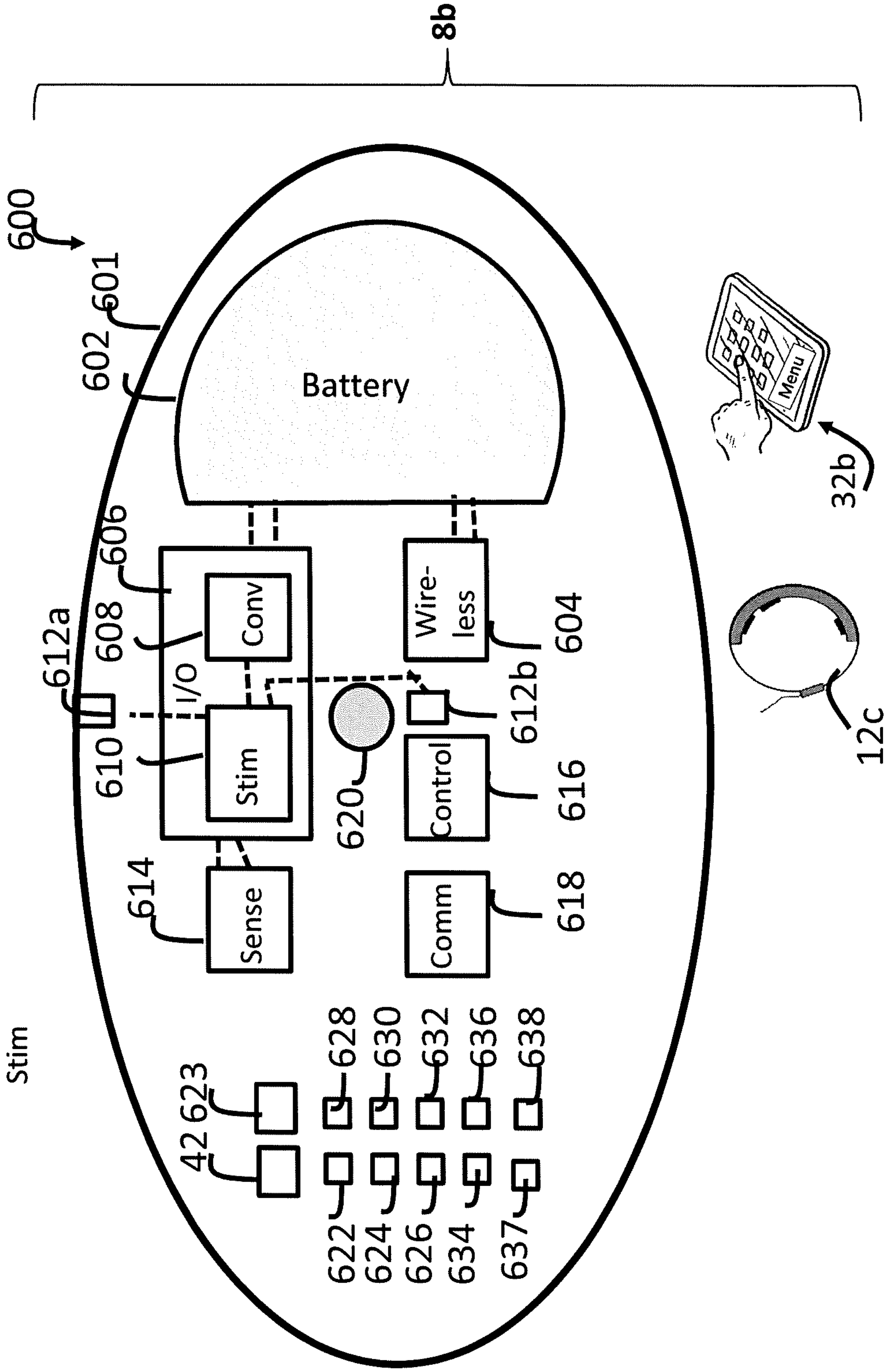
FIG. 20 is a schematic view a neurostimulation system including an implantable neurostimulator with modules and a power source, and an external stimulation device, and user device.

Implantable devices intended to stimulated the SAFN may use sites which have been found to be successful for SAFN block (Benzon H T, Sharma S, Calimaran, A Comparison of the Different Approaches to Saphenous Nerve Block Anesthesiology 3 2005, Vol. 102, 633-638). Implantation sites and procedures should account for anatomic variation reported across the population (Ertekin, Saphenous Nerve Conduction in Man, 1969; Wilmot V V1, Evans D J. Categorizing the distribution of the saphenous nerve in relation to the great saphenous vein. Clin Anat. 2013 May; 26(4):531-6.). FIG. 20 shows various sites where SAFN block has been successfully used and, while not limited by theory, the sites where SAFN may be successful should show correspondence. The pathway of the cutaneous nerve suggests that a stimulator configured to stimulate the L2, L3, and L4 dermatomes of the upper thigh in the treatment of pelvic floor disorders.

Figure 19A:
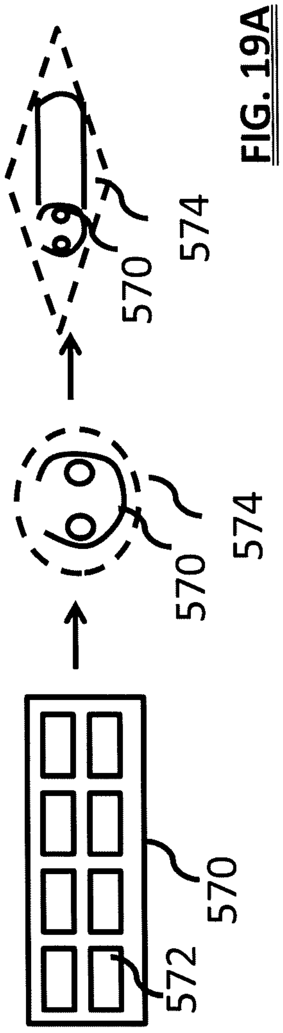
FIG. 19A is a schematic view of a mesh stimulator in a wrapped and unwrapped state.
Figure 19B:
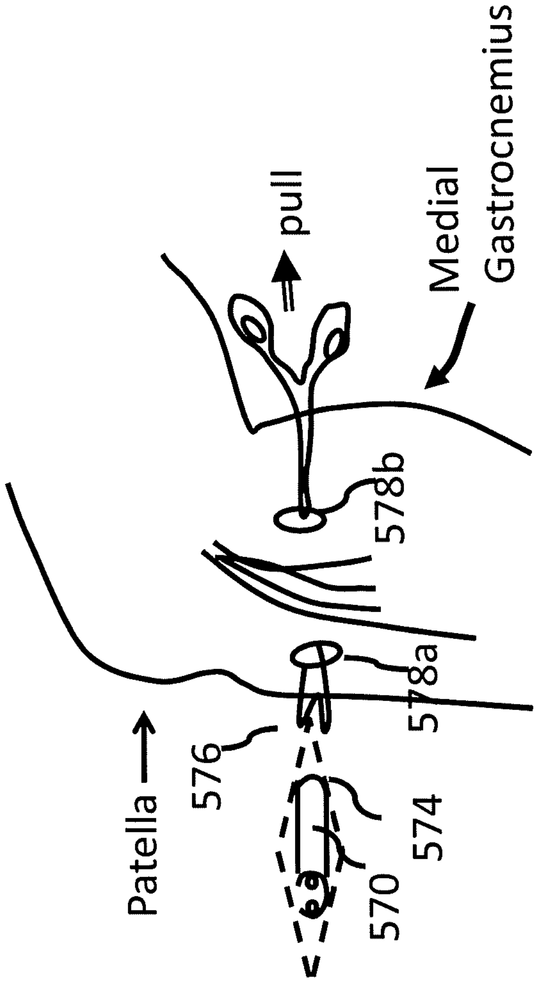
FIG. 19B is a schematic view a surgical paradigm for implanting the mesh stimulator.

FIG. 19A shows a schematic view of an implantable system for electrical stimulation of a nerve in the leg such as the SAFN. The system consists of a flexible and stretchable mesh material 570 (e.g, silicon-rubber) with multiple rows of embedded stimulator contacts 572 ("electrode array"). In the center panel a low-friction packaging material 574 (circular dashed-line) bundles the mesh material 570 into a folded state. The right panel of the figure shows a side-view of the mesh folded within the packing material. In the FIG. 19B, in a surgical embodiment, this occurs about 3 inches below the knee, but higher or lower may also be suitable. A pair of small vertical incisions are made (578*a*, 578*b*), approximately 4 cm apart and sufficient for a trocar to pass through each opening. The subcutaneous area between the incisions are blunt dissected such that (1) there is ample space for electrode array to be unfolded and (2) a trocar can be passed between the two incision points. A surgical tool such as a forceps is slid through the two incisions and grasps the mesh 570 to pull it back through the spaced between the two incisions to allow percutaneous "threading" of the mesh electrode array. The forceps is used to position the mesh 570 across the SAFN branches near the knee. Once the bundled mesh 570 has been pulled into a subdermal area, the opposite end of the mesh can be grasped using a second forceps (e.g. Kelly forceps), such that the low-friction packing material separates from the electrode array and is pulled out of the patient's leg. The electrode array mesh 570 is then allowed to unfold (flatten) within the subcutaneous space. The system provides a stable, long-term electrical stimulation of a peripheral nerve—such as the SAFN.

A main component of the system shown in FIG. 19A is a flexible planar sheet 570, within which multiple wirelessly powered neurostimulators are embedded (electrode array). Each stimulator may be a simple bipolar electrode with both contacts completely encircling different parts of the stimulator. The stimulator may have multiple channels such that electrical pulses can be applied to nervous tissue located above or below the planar sheet. The planar sheet 570 may consist of electrically-insulating material, and may form a continuous barrier (solid sheet) or have a porous surface (e.g., mesh). The planar sheet 570 will be flexible and may be designed such that it biases into a flat state (i.e., does not remain in a curved or folded when manipulated). At both ends of the electrode array, there will be several centimeters of absorbable suture connected to the planar sheet. Once the electrode array 570 is positioned within the leg, the suture will be used to close the surgical incisions, and also anchor the array within the surgically defined subcutaneous space by promoting rapid encapsulation.

Both sutures will be used to close both incision sites and also provide a method of stabilizing the electrode array until sufficient tissue encapsulation occurs. Appropriate types of suture material can be selected to control the time to complete or partial absorption. The suture material may be embedded or coated with organic or inorganic material to either speed up or increase the extent of post-implant tissue formation. The planar substrate of the electrode array may also include design factors—such as tines, hooks, organic glue—that will prevent migration of said implant away from the SAFN.

In an embodiment an implanted device can be similar to that disclosed by 20170135898 Implantable Electroacupuncture System and Method for Treating Dyslipidemia and Obesity, and can further be shaped into a or tapered cylindrical, ring, bullet shaped or full or half cuffed, with electrode anchoring features and various shaped electrodes at the end of a short pigtail lead or the device is leadless, with no leads or electrodes located at the distal end of leads. Alternatively, electrode contacts can be on both the implanted device body and also leads. For example, in an embodiment the coin shaped electrode can be positioned to stimulate the PTN and a conduit can relay a signal to at least one electrode located at the tip of the conduit which is positioned deeper in the tissue. The neurostimulator can also be used to stimulate the SAFN, such as the anterior branch of the SAFN near the medial malleolus. When realized with no leads the device can be implanted through a very small incision, e.g., less than 2-3 cm in length, directly adjacent a site which allows for stimulation of the SAFN to treat OAB.

FIG. 20 shows an embodiment of an implantable neurostimulator device 600 which is oval shaped, although it may be coin shaped, or rod shaped, if the internal components are modified to fit inside the housing 601. In embodiments, the neurostimulator device 600 (as well as those shown in FIGS. 15A to 19B) can incorporate all of the modules and functionality which has been described for the external device 12, including the modules disclosed in FIG. 2, but with appropriate miniaturization of the hardware. While example embodiments disclosed herein are for purposes of illustration and the operations, modules, and algorithms disclosed are understood to be applicable to systems using either implanted and external neurostimulators. The device is powered by a battery 602 which can be rechargeable or non-rechargeable. If rechargeable, this can be recharged using wireless power harvested by a wireless rechargeable module 604 having harvesting circuitry for receiving magnetic or RF based energy. An input/output module 606 contains stimulation module 610 having components such as signal/pulse generation, amplification, safety, regulation and control circuitry to provide output circuitry for stimulation to at least a first electrode 612*a* (which may be disposed on the annular wall of the housing 601, and at least a second electrode 612*b* which is disposed on the bottom surface of the device 600. A converter module 608 is provided for converting power to AC, DC, attenuation, or boost conversion of signals. A sensing module 614 provides sensing of electrical signals sensed by the electrodes 612*a*,612*b* and other sensors which are operated by the device. The control module 616 controls the operation of the device to provide stimulation therapy according to stimulation protocols and to control the communication of power and data signals with external devices using the communication module 618. The control module 616 is realized with microprocessors, clocks, timers, memory, and any other state-of-the-art electronic component that is used in microneurostimulators. A pressure sensor 620 is configured within the housing in order to sense changes in pressure applied to the housing and can also be configured to work with a button control that resides on the housing. In addition to the modules shown, any module described for the external stimulator 12 and the system 8, is also understood to be realized as a module of the implanted neurostimulator 600. Additionally, an external stimulation device 12 can provide both TENS stimulation and stimulation by the implanted device by sending power and/or control signals to the implanted device. When the external device 12 does not provide TENS it may be configured without the electrode arrays and other features which provide external stimulation and may simply provide a stimulation protocol by controlling the implanted neurostimulator 600. In an embodiment, the implanted stimulator may incorporate features of disclosed in U.S. Pat. No. 9,364,390, entitled, Implantable electroacupuncture device and method for treating obesity, incorporated by reference herein.

Data sensed by the pressure sensor 620, is processed by a button sensing module 622 which is configured to assess the number and duration of button presses over a given time period. This permits user input to include durations and patterns of button presses which serve as command signals that cause different adjustments of operation (e.g., pressing for two short durations can cause intensity to decrease). A gesture module 624 has an accelerometer and can process movement using algorithms such as the method of FIG. 7. A sonic signal can be sensed by a sensor on the housing 644 or a sound sensor within the housing provided as part of the sonic sensing/stimulation module 626, which can also operate as a sonic stimulation module that provides transdermal sonic alarms via a sonic transducer 623. A light sensor module 628 includes a light sensor that can sense signals received by a light sensor/transmitter 643 disposed on, or incorporated into, the housing 601 or through a transparent window 646 of the housing 601. This module may also allow the implanted device to measure blood oxygen. An EMG module 630 is configured to process EMG data and also to detect gestures (e.g. the user stomping their feet a selected number of times causes pre-defined muscle activity) which is interpreted by the module 630. The EMG module also allows detection of evoked motor activity by the implanted device to occur. The EMG data is sensed by the electrode contacts that typically supply stimulation, or by a pair of electrodes disposed on the housing 647*a*, 647*b*. A magnetic module 632 is configured to receive and process a magnetic signals sent by an external user device 32*b*, including magnetic communication and control signals. A wireless/RF module 634 is configured to process communicate using wireless/RF signals (e.g., ZigBee, Zarlink, Bluetooth, etc). An electric module 636 is configured to process electrical signals sensed by the sensors 647*a*,647*b* on the top of the housing 601. Communication of control and data signals can occur in conjunction with the TENS device that provides these signals instead of/in addition to treatment stimulation signals. Alternatively, a user device 32*b* is configured with two electrode contacts which are applied to the user's skin to control the implanted device 60. This may be advantageous for implantable neurostimulators which are close to the skin surface and can sense electric communication signals applied to the user's skin. A vibration module 637 includes a motor or mechanical actuator into order to provide vibration signals, such as those used to provide notification alerts. An event management module 638 is configured to store a record of all user input data including button presses, abort commands, and related data that are related to events such as stimulating starting or stopping. In an embodiment, the modules just disclosed, 622 to 638 may be realized across system 8*b* components. For example a user's smartphone can be figured to provide sonic signals (audible or inaudible frequency range) to communicate or control the implanted device so that if a user has forgotten their user device 32*b*, their phone can serve to control the implanted device. The modules and command signals defined in step 664 can be used by step 307 of FIG. 22. Either accelerometer, EMG, or microphone data can measure user activity and, embodiments that use one sensor may be substituted with another in different embodiments.

Figure 21C:
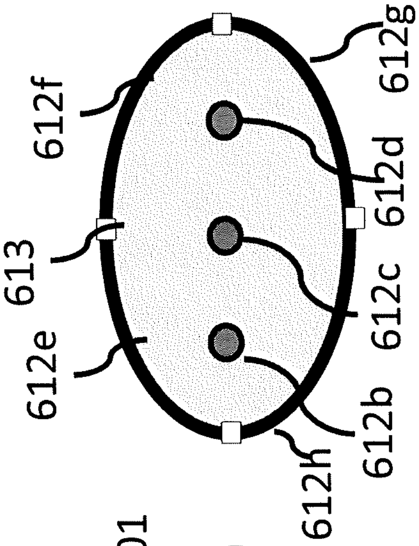
FIGS. 21A, 21B, and 21C show schematic views of a neurostimulator from the side, top, and bottom, respectively.
Figure 21B:
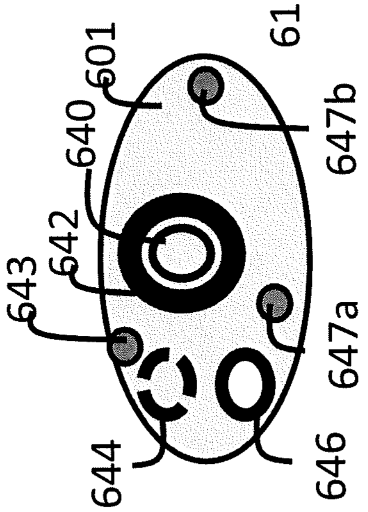
Figure 21A:
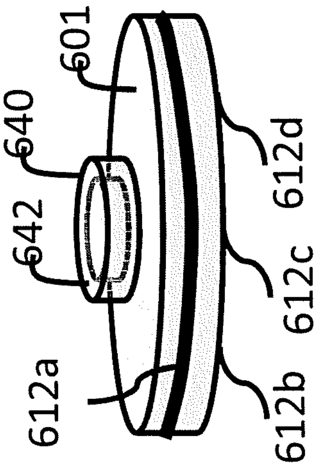

FIG. 21A shows a side view of an embodiment of a neurostimulator having a housing 601 with an annular electrode 612*a*, and three electrodes on its bottom surface 612*b*, 612*c*, 612*d* that faces the nerve being stimulated. There is also a low profile button control 640 disposed on the housing which is located over the pressure sensor 620. The button control can reside on top of the housing 601 or may intersect the housing so that it can contact the pressure sensor directly. The button control may be covered by a suitable material such as a silicone or rubber cover 642 (or other flexible and biocompatible material) that seals the button control against the housing. The button can be realized using a gap in the housing 601 that the silicone seals. The button can allow a user to press against their skin in order to send a command signal to the implanted device without having to use an external controller. FIG. 21B shows a top view of an embodiment of a neurostimulator having a housing 601 disposed with a button controller 640 and seal 642, and a sensor 644, and a clear window through which light can pass. FIG. 21C shows a bottom view of an embodiment of a neurostimulator having a housing 601 disposed with a three electrode contacts 612*b*, 612*c*, 612*d*, and four independently operable contacts along the annular edge 612*e,f,g,h* to allow "steering" of the stimulation field. Use of an oval rather than circular housing 601 can allow larger stimulation fields than a circular housing 601, and this may be especially useful in the stimulation of the SAFN when the oval is oriented to align with the axis of the user's leg.

When the button control 640 is realized as a deformable switch it can be used to obtain user input button presses that are processed by the button module to toggle the implantable device ON or OFF using button press patterns such as depressing the side of the device 2 or 3 times for 1 second to turn it on. Button presses can be used to activate the device rather than, or in addition to, relying upon a fixed schedule.

In an embodiment, a polymer enclosure surrounding at least a partial section of the housing 601 of an implantable device can include one or more suture holes, channels, perforations, or any other recession, channel, or inner surfaces that assists with placement of sutures, or other securing means. The polymer enclosure incorporating fixation members may extend over only a portion of the housing 602 and allow a user to toggle the state of the device via a button, while also provide for fixation of the implant Implantable Stimulator Therapy Initiation and Communication.

In an embodiment, the system provides users with warning prior to initiating stimulation such as scheduled stimulation or stimulation contingently provided based upon assessment of sensed data. An external neurostimulator such as a wearable TENS system, external controller, or an implantable neurostimulator is configured to provide at least one notification signal 304 such as anticipatory electrical stimulation according to an anticipatory stimulation notification protocol. The notice serves to provide advanced warning to a user so that stimulation does not start unexpectedly. The notification signal can be provided by a display/notification module 42 which provides the notification and operates according to a protocol which scans for user input in response to the notification. The protocol can include providing notification in the form of a sonic, auditory, visual, vibratory, electrical or other signal. After the notification signal (which may be a set of signals) is provided 304 an "abort interval" is defined during which the user can abort the pending stimulation. For example, the protocol uses a notification signal that includes stimulating an individual for at least one selected period such as 15 seconds followed by a 2-minute abort interval. Alternatively, the anticipatory stimulation includes presenting the stimulation protocol at a lower intensity level associated the user's sensory threshold, for a duration before increasing the stimulation to the intensity level used during stimulation. After the anticipatory stimulation protocol provides the notification signal and the abort interval completes then the stimulation therapy begins. The notification protocol may be programmably defined to have more than one notification and abort interval prior to triggering therapy initiation. In this example, if the protocol defines two notifications and abort intervals then the user is provided with at least 4 minutes to abort the stimulation prior to commencement. In an embodiment, the system 8*b*, includes a device 600, external user device 32*b*, and external stimulator 12*c* configured to provide stimulation in conjunction with the device 600.

Figure 22:
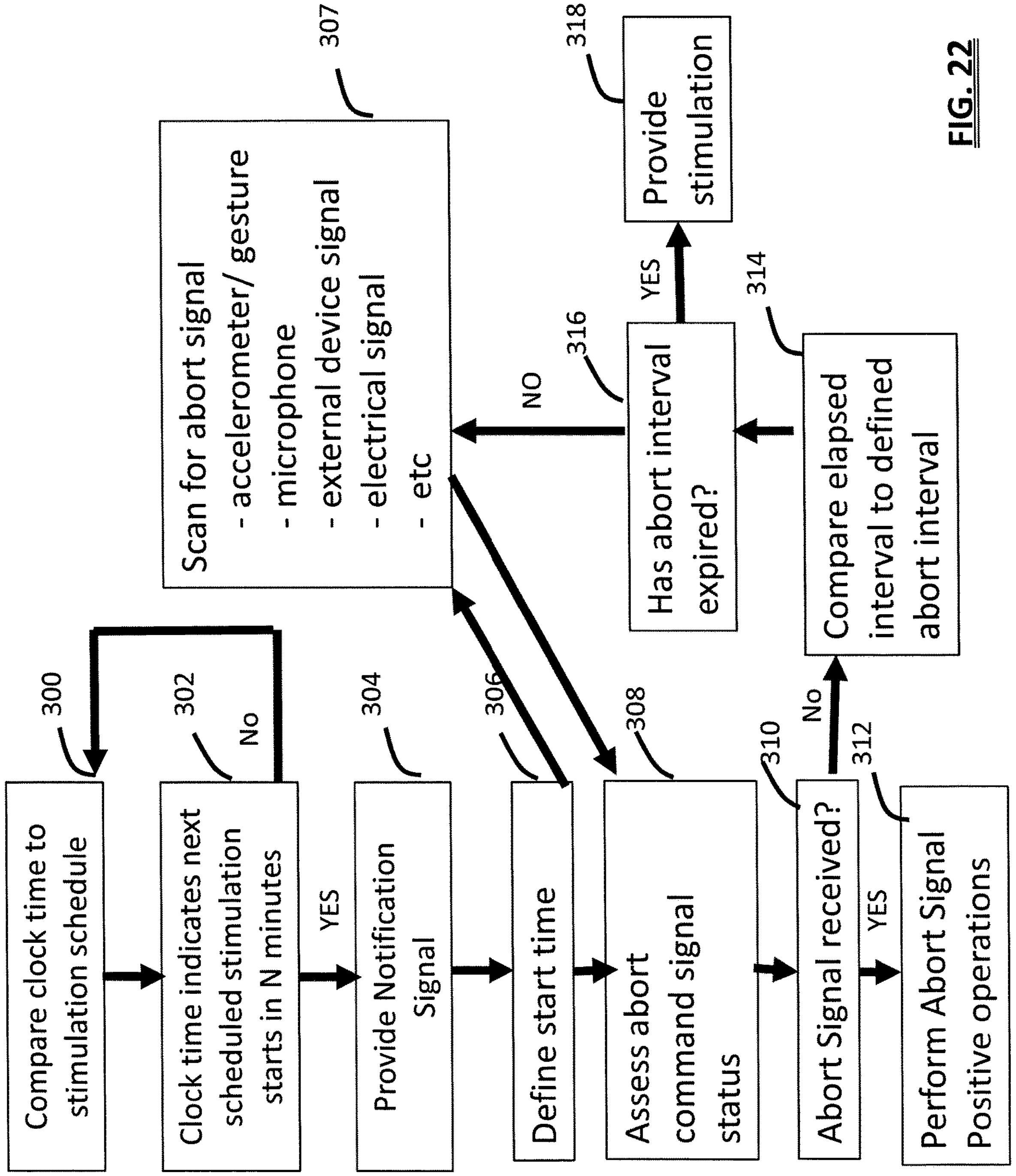
FIG. 22 is an information flow diagram of a method for providing advanced notification to a user.

FIG. 22 shows an embodiment of a method that is provided by a control module of system having at least one external or implanted neurostimulator device, although in this example, an implanted neurostimulator will be used as illustration. In step 300 the control module compares clock time to a stimulation schedule (or a timer to a duration criterion). If the clock time indicates that the next scheduled stimulation scheduled be triggered in step 302, then step 304 occurs (using the notification module 42) and a notification signal is provided to the user. If not, then the method returns to step 300 or enters a lower powered state for a given duration, or performs other operation as defined. In step 306 a start time for an "abort interval" duration is logged. In step 307 the control module 40 senses data from sensors of the sensing module 50 in order to scan for the presence of an abort signal. In step 308 the device assesses the sensor data and updates the abort signal status. In step 308 the step determines if the abort signal has been received (i.e. status=true or false). If the abort signal is received 310 then the method moves to step 312 and abort signal positive operations occur. If not then the method proceeds to step 314 and the duration of the abort interval is compared to the elapsed interval to determine if the abort interval has expired. In step 316, if the abort signal has expired then the method moves to step 318 and the system provides the stimulation. If in step 314 the abort interval has not expired, then the method moves to step 307 where the device again scans for an abort signal. When an abort signal is received, then in step 318 the device or external controller may reschedule therapy (e.g., for later that day) so that the user obtains a sufficient treatment dose over time.

In an embodiment, an implanted neurostimulator 600 operates to provide the method shown in FIG. 22 and provides a notification signal in step 304 such as a series of brief stimulation bursts (e.g. five to ten 300-msec bursts, which may be repeated 1 or more times). Alternatively, the implanted neurostimulator 600 can issue a sonic signal or vibration. The user is able to abort a scheduled stimulation using body movement or other means rather than using a user device 32, which may not be near the user.

In an embodiment, a neurostimulation system 8*b* for providing electrical stimulation and notification to a user comprises a neurostimulator that is adapted to provide electrical stimulation to a target nerve of a user, such as at a location on or in their leg. The system 8*b* is configured to operate to achieve the method shown in FIG. 22 in the following manner. A processor controlled control module 40 is mounted within said neurostimulator and is configured to operate in accordance with a predetermined stimulation protocol. The protocol is stored in control module 40 and uses a current clock time, and a scheduled time which is a next stimulation time that is defined for actuating the neurostimulator to provide stimulation therapy. The protocol also defines an abort time interval which exists between the current clock time and the next stimulation time. The neurostimulation system 8*b* also includes a processor controlled notification module 42 within the neurostimulator and coupled to the control module 40. The processor controlled notification module is configured to notify the user, that the neurostimulator will be actuated to provide stimulation at a predetermined clock time, as may be done using an electrical stimulation signal as a notification signal which can be provided by electrical contacts on the housing 647*a*,647*b*. The processor is also configured to determine whether a user abort command signal is sent (or sensed) within the abort time interval that expires prior to, or coterminous with, the next stimulation time and to actuate the neurostimulator to provide stimulation treatment using the stimulation module 48 at the next stimulation time if a user abort command signal is not sent within the abort time interval. In the case where the abort signal is sent by the user within the abort time interval, then processor will reschedule the next stimulation time by adjusting the treatment schedule data of the scheduling/compliance module 60 or terminate actuation of the neurostimulator that corresponds to the provision of treatment.

In embodiments the neurostimulation system uses either an implanted or external neurostimulator (i.e. TENS stimulator), or both, to provide the stimulation treatment. The user abort command signal can be defined in a number of manners including, a user gesture detected based upon data sensed by an accelerometer of the accelerometer/actigraphy module 47, or a user gesture detected in data sensed by a pair of electrodes such as may exist on the housing 647*a*,647*b*. An electrical signal sensed by a pair of electrodes 647*a*,647*b* and provided by an external user device 32*a* that applies an electrical signal to the skin may also serve as an abort command when this is defined as an abort command signal. The abort signal can also be a sonic signal provided by a user device or which is a user's voice that is sensed by a sonic transducer of sonic sensing module 626. The user abort command signal can be also be defined as a magnetic signal or RFID signal sensed by a magnetic module 632 or wireless/RF module 634, or as a light signal sensed through a light sensor disposed on the housing of an implanted neurostimulator which is sensed by a light sensor module 628. The user abort command signal can be also be defined as a button press of a button control 640 disposed on the housing 601 an implanted neurostimulator, or the user pressing on the housing of the implantable device sensed by a pressure sensor 620 disposed within housing of an implanted neurostimulator that is sensed by the button sensing module 622. The user abort command signal can also be defined as a button press of a button control disposed on the housing a neurostimulator which is a TENS device.

In embodiments the neuro stimulation system provides stimulation to a target nerve that is the SAFN or the PTN, or other nerve upon the disorder being treated. The stimulation of the target nerve may result in a motor evoked response or sensory evoked response when the stimulation results in nerve recruitment.

In embodiments, the notification signal sent in step 304 is an electric signal having a larger amplitude than the electrical stimulation which is provided to the user during stimulation treatment, and the amplitude has been selected in relation to a user's pain threshold 502*d*.

In one form, the notification signal is an electric signal having a smaller amplitude than the electrical stimulation which is provided to the user during stimulation treatment, and the amplitude has been selected in relation to a user's sensory threshold 502*a* and nerve recruitment threshold 502*b*.

Figure 23:
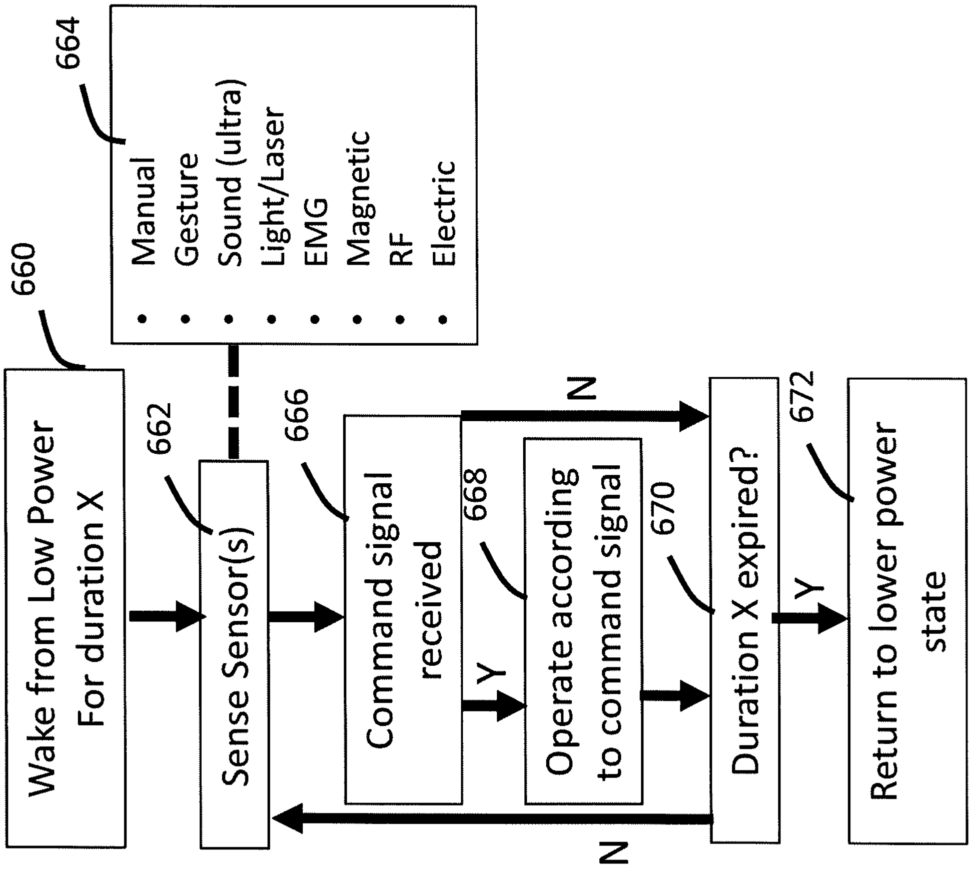
FIG. 23 is an information flow diagram of a method for obtaining user input to adjust device operation.

FIG. 23 shows an embodiment of a method that is provided by a control module of system having at least one external or implanted neurostimulator device, although in this example, an implanted neurostimulator will be used as illustration. The method allows the operation implanted device to be modified by user input or commands issued by the system 8*c*. The system performs a step such as step 300 where the control module compares clock time to a programmable interval value, or clock time, or other event that causes the device 600 to awake from a low power state 660. Alternatively, in the low power state the device 600 can include continuously providing power to a particular sensor such as an accelerometer.

After the method starts with step 660, in step 662 data is sensed from sensors according to protocols previously defined in step 664. For example, the sensors can include the registration of depressing of the button controller 640, which is sensed by the pressure sensor 620, and processed by a button sensing module 622. A gesture such as a "strong tap" can be sensed which is processed by a gesture module 624 having an accelerometer. A sonic signal can be sensed by a sensor on the housing 644 or a sound sensor within the housing provided as part of the sonic sensing module 626. A light signal can be sensed by a light sensor of the light sensor module 628, and the signal is received by a light sensor disposed on the housing 601 or through a transparent window 646 of the housing 601. This module may also allow the implanted device to measure blood oxygen. An EMG module 630 is configured to process gestures such as the user stomping their feet 3 times which causes pre-defined muscle activity to occur which is sensed by the electrode contacts that typically supply stimulation, or a pair of electrodes disposed on the housing 647*a*, 647*b*. A magnetic module 632 is configured to process a magnetic signals sent by an external user device 32*b*, that provides magnetic communication and control signals (using near field communication or Reed switch control paradigms). A wireless/RF module 634 is configured to communicate using wireless/RF signals (e.g., ZigBee, Zarlink, Bluetooth, etc). An electric module 636 is configured to process electrical signals sensed by the sensors 647*a*,647*b* on the top of the housing 601 which can be provided by the TENS device or by a user device 32*b* that has electrode contacts. This may be advantageous for implantable neurostimulators which are close to the skin surface and can sense electric communication signals applied to the user's skin. In an embodiment, the modules just disclosed, 622 to 636 may be realized across system 8*b* components. For example a user's smartphone can be figured to provide sonic signals (audible or inaudible frequency range) to communicate or control the implanted device so that if a user has forgotten their user device 32*b*, their phone can serve to control the implanted device. The modules and command signals defined in step 664 can be used by step 307 of FIG. 22. Either accelerometer, EMG, or microphone data can measure user activity and, embodiments that use one sensor may be substituted with another in different embodiments.

In step 666 the device 600 determines if a command signal has been received, and if so it may operate according to the command signal 668, while if the signal was not received then the method moves to step 670. In the case where the duration for scanning for a command signal has expired step 670 moves to step 672 and the method ends, while if the duration has not expired then the method returns to step 662 and additional data is sensed.

In an embodiment, during the notification period before the stimulation starts (steps 304 to 314) a device 12/600 operates its communication module to receive any commands issued by the user (e.g. abort or delay). A user device 32*b* can be used to send a signal to delay or abort the scheduled stimulation. Alternatively, when the device is provided with an accelerometer it is programmed to sense a behavioral gesture such as "striking" or "double tapping" by a user. For example, if a user spanks their leg near the device twice within 10 seconds after a notification which comprises providing warning stimulation then the device will delay the stimulation by an hour (at which point the anticipatory stimulation protocol may again be provided). A different number of "taps" (e.g. four) can be defined to abort the stimulation and the next stimulation will not occur until the next scheduled stimulation. Alternatively, the taps can be coded wherein if the user taps the device housing then this is defined to indicate (confirmation) to start the stimulation immediately. For increased safety, a "slap" detection can be defined to confirm that stimulation should be provided, while no "slap' indicates the scheduled stimulation should be aborted. The anticipatory stimulation of the notification signal can occur at the same intensity as the therapy stimulation or can be set higher (or use notification with a pattern selected to be noticeable such as five 300 msec bursts presented with 300 msec pauses) to increase the chance that the user will notice the warning signal. Other components of the system such as the patient/user controller 32*b* can work in collaboration to provide a multi-modal user alert and to obtain a user response. The notification protocol can also be programmed to attempt to provide notification by an external device, and if the external device does not provide an acknowledgement ("ACK" signal), then the implanted device provides notification without the external device (e.g., electric tickle).

In an embodiment, the implanted device 600 is provided with electrodes 647*a*,647*b* that sense EMG or other electrical signal from the body of a patient. The EMG module is configured to sense and detect command signals that are provided by the patient's body. In an embodiment, the device is configured to detect a behavioral gesture such a user "curling" and "releasing" their toes a selected number of times (e.g., 3) as a command signal or abort signal. The physiological response associated with the behavior can be recognized by the appropriate sensing module (e.g. EMG module) using signal processing algorithms such as template matching, machine learning, time-frequency analysis (e.g. the time-frequency spectrum can be analyzed for a selected number of bursts in a frequency range associated with muscle activity), or other well-known method. Alternative command signals can entail a programmably defined pattern of foot extension or flexion (which may also include rotation).

Patient Screening, Induction, and Maintenance Therapy

In an embodiment, in order to determine if a certain type of stimulation is appropriate for a patient, after stimulation parameters and at least one stimulation site is assessed/selected 678, a screening step 680 is performed. Screening can occur prior to using an at-home wearable stimulation device or before receiving an implantable device. In an embodiment patients are screened at a clinic using percutaneous stimulation during an "induction" period. Patients who respond to induction by showing a minimum change in improvement for at least one OAB measure are selected to continue using a home-based treatment system with a wearable stimulator. Stimulation parameters and sites determined to be successful clinical induction period can be used to select those used by the wearable. Screening of candidate patients for an implantable device can occur using at-home TENS or clinic-based percutaneous stimulation to determine successful candidates. Prior PTNS failure should not be used to exclude screening of a patient for SAFN stimulation. Better results can be obtained with SAFN stimulation which modulates different neural circuits. When testing or treating patients with SAFN or PTN stimulation, an insulated (rather than uninsulated) needle may provide less cutaneous discomfort and greater selectivity.

Figure 24:
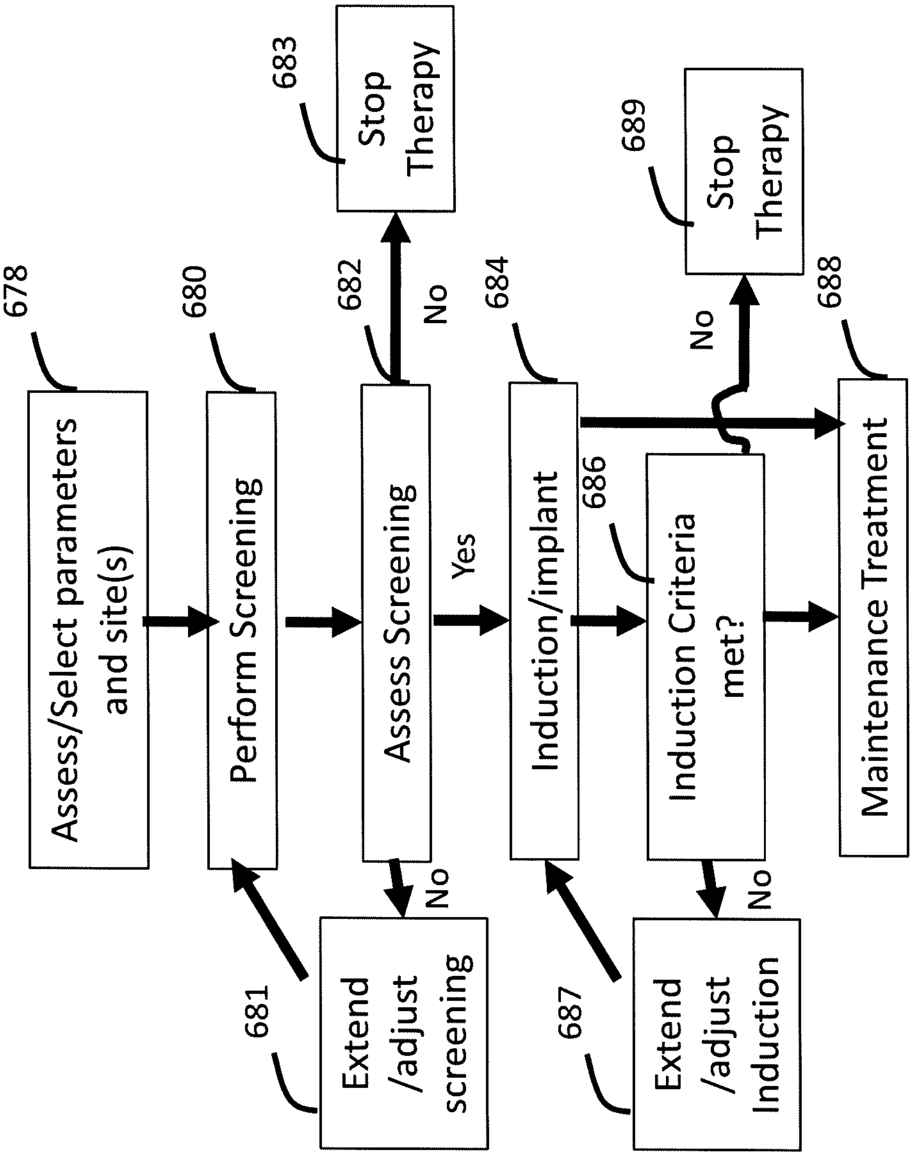
FIG. 24 is an information flow diagram of a method for contingently providing screening, induction, and treatment related to treating a user; and, FIG. 25 is an information flow diagram of a method for notifying a user of a therapy event and obtaining a response.

As shown in FIG. 24, in an embodiment, a screening 680 step includes using a temporary lead 676 coupled to an external pulse generator (which can be provided by device 12*a* that is worn by the patient, see FIG. 5). Alternatively, the pulse generator can be a specialized device worn on a belt or within a band secured to the upper calf for a screening period lasting between 1 and 6 weeks, but preferably 1-2 weeks. During screening stimulation can occur daily or otherwise. The temporary lead 676 has lead contacts 677 on its distal end that are implanted at the stimulation site and the incision is covered with a bandage. A surface electrode 28*e* can serve as a return electrode. Imaging (e.g., ultrasound, fluoroscopy, MRI) can be relied upon to improve implantation of the device or lead but it is not required.

In embodiments, when screening is done for the SAFN the temporary lead 676 can be inserted in the medial-anterior aspect of the leg between the knee and the medial malleolus. When screening is done for SAFN the percutaneous stimulator may be simply have its temporary lead 676 placed in the region located between the medial condyle of the tibia and the superior border of the medial gastrocnemius muscle, oriented in the anterior-posterior direction and a width of approximately 1.5 cm.

In the case of SAFN stimulation, patient sensation and feedback may improve lead placement but is not required as part of screening 680. Some patient's may not be able to sense the stimulation due to neuropathies, edema or disorders such as diabetes. In these patients, alternative assessment of location and stimulation parameters such as the recording of evoked responses in the user or changes in bladder activity or other measure can be used to assess stimulation parameters and location. The sensations reported by the patient may include sensory threshold, recruitment, discomfort, and maximum sensation levels, and qualitative measures related to pain, warmth, and or other descriptions of the sensations. As an alternative to relying only on perception of stimulation induced sensations and/or paresthesia, the ability of the stimulation to mask or reduce sensation of a sensory stimulus (e.g. pain/pressure stimulus) imposed on the medial aspect of the leg can be used to determine correct placement of a lead. Additionally, it is often possible to temporarily or acutely mask or reduce the evoked paresthesia by applying pressure (e.g., manually depressing skin) on parts of the lower leg that are distally located from the site of electrical stimulation. Alternatively, when the SAFN is recruited the sensory threshold for pain or pressure at a more distal site may be elevated. The presence, absence, or amount of sensory masking can be used to assess both candidate stimulation parameters and sites. In order to determine if a patient may not be able to sense the SAFN stimulation, various sensory tests can be done. For example, in a 2-point orientation discrimination test, the minimum distance between two contact points on the skin and its orientations (e.g., along or across the leg) is used to assess sensory acuity in patients. Other sensory tests can include assessing a patient using pressure or other tactile tests, assessing sensory masking by using two stimuli, etc. The inability to detect nerve recruitment by paresthesia does not indicate that a user will not benefit from SAFN stimulation. If a site cannot be found that allows subjective confirmation of nerve recruitment, then the user can still undergo induction to determine if treatment benefit is obtainable.

When screening is assessed 682 and the results are evaluated as is successful, the patient may proceed to step 684, which includes implantation and/or stimulation according to an induction schedule. If screening assessment 682 does not result in a positive outcome, then the screening step can be extended and/or the treatment stimulation parameters/site are adjusted 681, or the therapy stopped 683. When induction stimulation is provided 684, the patient response is assessed 686 and this leads to maintenance therapy schedule 688 if one or more induction criteria are met, while failure to meet induction criteria causes maintenance therapy to be adjusted or extended 687, or the therapy is stopped 689.

Therapy Adjustment

In embodiments, the therapy schedule is adjusted dynamically such as moving from an induction to treatment schedule after treatment response meets one or more criteria 686. Initially, an implantable device therapy schedule implemented by the control module occurs more frequently or longer during an induction period. An external stimulator 12*b* provides supplemental stimulation during this time in order to conserve the battery of the implanted device. For example, the implanted device is programmed to deliver 3 hours of stimulation per day for the first 2-4 weeks during induction and then automatically transitions to 30 minutes every other day. Alternatively, the external stimulator provides 3 hours of stimulation every day for the first 2-4 weeks and the implanted stimulator schedule of stimulation does not change, remaining at 30 minutes every other day. The stimulation amplitude required to activate a target nerve by surface stimulation can be reduced by strategically applying TENS at the location of the implanted stimulator. If the housing of the stimulator is comprised of an electrically-conductive material then this may enhanced the effects of the stimulation signal. We have previously described this system as eTENS (U.S. Pat. No. 9,884,187). This system and method could be used to conserve the battery life of an implantable neurostimulator, or may be used in lieu of the implant once the battery has been depleted, or the implanted device becomes non-functional.

As shown in FIG. 9, adjusting the stimulation schedule (e.g., moving from induction to maintenance) can be done by the system 8*a* assessing user response to surveys 488 (or induction can be assessed by a doctor). Surveys may prompt the user to assess symptom severity over a period such as the prior 24 hours. For example, users may interact with the user device 32*b* to provide a score of 1 to 10 with respect survey items related to “daytime incontinence”, “night time incontinence”, “daytime urgency”, “night time urge”, # diapers or pads used. If the patient response data obtained by the surveys indicates improvement from a baseline 496*a*, then selected operations occur 496*a* such as prompting for a decrease in number of stimulation sessions per week, or duration of each stimulation session. Alternatively, an increase in therapy may occur if assessment of survey data 494 related to the initial induction period (e.g., 3-5 weeks) indicates worsening 496. Alternatively, in step 496*b*, the treatment protocol of the control module 40 may define step 496*b* to include transmitting the patient survey response data to a remote computer 82 so that a physician can evaluate the data and then instruct the patient on how to change the therapy or the module changes the therapy remotely using a computer 82 that interacts with the system 8*b*. In an embodiment, if the patient does not report improvement after 3-5 weeks of an induction period 684, the therapy parameters may change so that the stimulation frequency changes, for example, from a constant frequency of 20 Hz to 10 Hz or one that alternates between 10 Hz and 20 Hz.

In an embodiment, an implantable device with a battery provides therapy during the first 2-4 weeks the stimulation scheduled to occur more frequently, such as once or twice per day (in morning and just before bed) for 0.5, 1, or 2 hours. This regimen can then automatically decrease (i.e. step 686 is skipped) the number of stimulation sessions per day, the length of each stimulation session, or the strength of the stimulation amplitude. After a second duration such as 2-4 weeks, this can be decreased further. Maintenance therapy schedules can also be decreased over time with a first schedule providing a greater “dose” of stimulation than the second. For example, the maintenance therapy schedule can be decreased to only 1, 2, or 3 times a week/month.

When an implantable device is powered and controlled externally rather than having a battery and providing scheduled therapy, then the user device 32*b* provides reminders when maintenance or induction therapy is scheduled so that the user operates the external stimulator. In embodiments, systems 8*b* that operate implantable devices rely upon the same modules and features disclosed for the wearable device. For example, the reminder schedule screen shown in FIG. 6A is used to determine a treatment schedule and associated reminders.

Figure 25:
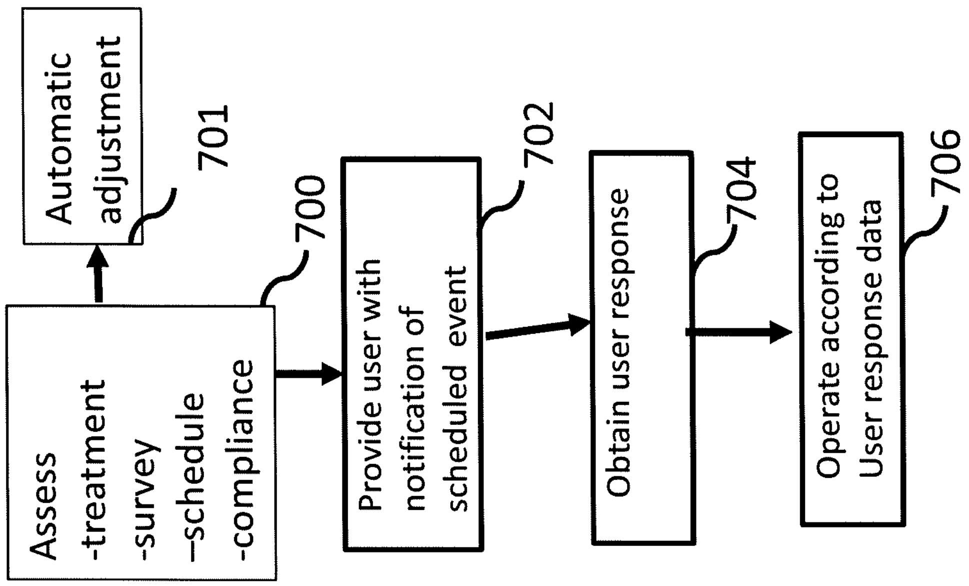

As shown in FIG. 25, in embodiments, the user device 32*b* assesses the schedule 700 that has been defined by a user for therapy events such as providing a minimum number of scheduled treatments, or responding to surveys, and this may be done in relation to compliance. For example, if a treatment session has already been provided on a day when it is scheduled then the notification for that day is cancelled. Alternatively, in the case where a user did not supply treatment after a reminder alarm was sent, step 700 proceeds to step 702 and the user device 32*b* provides a reminder survey prompt about a scheduled event such as a missed stimulation session. This may include a selected schedule adjustment (e.g., “It is Wednesday, and you were supposed to stimulate this morning. Remind you later today? “Y/N”). The user response is obtained 704 and the system operates according to the user response data 706. For example, in step 706, if the user input data indicates “YES”, then the user will be reminded 3 hours later if they have not provided a stimulation session prior to that time. If the user chooses “NO”, then in step 706 the reminder will stop or will stop until the next scheduled session is due. Alternatively, the user device 32*b* may be configured to automatically adjust a scheduled event (stimulation or survey) 701, and reschedule stimulation later in the day without surveying the user. Additionally, step 700 is configured to provide advanced notifications of an upcoming scheduled stimulation session (e.g., “It is Wednesday, and you are scheduled to stimulate later today. Remind you later today? “Y/N”). In step 706, if the user chooses “Yes”, then the user will be reminded 3 hours later if they have not yet provided a stimulation session prior to that time. If the user chooses "No", then this does not occur. In an embodiment the scheduling/compliance module 60 can be integrated with the user's calendar, such as an electronic calendar (outlook), and if the user schedules an appointment during a time when stimulation is scheduled, then in step 701 the scheduled stimulation is moved later in the day, or to a subsequent day, according to scheduling rules which may be user defined. In an embodiment, the scheduling/compliance module 60 can operate the survey module prompt the user whether there are any events in the upcoming week that may interfere with the provision of stimulation. The user may then be prompted to change the stimulation schedule for the upcoming week, after which the default schedule of stimulation will resume. Additionally, if the upcoming week contains a holiday or other event then the system 8 may prompt the user to consider adjusting the scheduled treatments. In an embodiment, the system 8 can obtain weather information from remote computer 80 operated by a service that provides weather information and the survey module may ask if a user wishes reminder notices about user behavior to be modified according to changes in whether. For example, during a heat wave, the user device 32 provide daily reminders about drinking too much water, or other behaviors that may worsen OAB symptoms.

In an embodiment, in step 700, the method is defined so that the user device **32*b* provides notifications about compliance failures based upon an failure to provide a selected number of scheduled treatment sessions (e.g., "It is Wednesday, and you have not stimulated in three days. Remind you later today? Y/N"). If the user provides patient input data indicating "YES", then the user will be reminded 3 hours later if they have not provided a stimulation session prior to that time. If the user chooses "NO", then the reminder will stop, will stop until the next scheduled session is due, or the system 8*b*** may perform other compliance failure operation.

In embodiments, during maintenance therapy 668 TENS provides the delivery of electricity across the surface of the skin to activate underlying nerves in a therapy session of generally 30 or 60 minutes for OAB treatment. Alternatively, a therapy session may last all night and may include both therapy-ON durations of 30-60 minutes followed by therapy-OFF session also of 30-60 minutes (or longer). Therapy can provide both acute (i.e. during stimulation) and prolonged (after stimulation) bladder modulation. When stimulation is provided throughout the night, the system 8 may provide ongoing acute stimulation to decrease the risk of bedwetting. Therapy provided during the day, or just before bed, can often extend to benefit during the night and for days or weeks afterwards. While increasing the therapy "dose" by increasing duration of the therapy session, amplitude of stimulation, and number of sessions each week may provide increased benefit, it may be that a stimulation session of 30-60 minutes once a week will be sufficient. In other words, increasing "dose" above some point of sufficiency may not provide additional benefit for a particular user. A treatment regimen may use a minimum duration of stimulation found to be sufficient to maintain therapy benefit, and can be decreased over time according to a predesignated schedule or according to user input indicating some level of benefit has been obtained. The assessment of benefit can also occur using sensed data, (e.g. biofeedback) obtained using either external or internal sensors configured to sense characteristics related to the condition such as bladder activity, pressure, or sphincter contraction. Sensed data can also be used to make adjustments in steps 681 and 687. The assessment may include review of patient response data, if patient response data meets a criterion, due to a time-based schedule, or a combination.

The adjustment of therapy can also occur within a stimulation session over time and can increase gradually to the target intensity such as over 30 seconds in the awake protocol, and can be longer (e.g., up to 5 minutes) in the sleeping protocol.

Candidate Stimulation Sites

When selecting sites for implantation 678 to provide electrical stimulation of the SAFN, sites (and methods used to confirm site location) previously used by others to provide SAFN block may serve as good candidate stimulation targets in the treatment of pelvic floor disorders such as OAB (e.g., Benzon H T, Sharma S, Calimaran, A Comparison of the Different Approaches to Saphenous Nerve Block Anesthesiology 3 2005, Vol. 102, 633-638, incorporated by reference). For example, a perifemoral approach includes the step of needle insertion 4 cm below the inguinal crease and 0.5 cm lateral to the femoral artery. To assist in detecting the SAFN, at a depth of 2-4 cm, the adjacent nerve which connects to the vastus medialis muscle is stimulated with a nerve stimulator at 0.4 mA or less (2-Hz frequency, 0.1-ms duration), resulting in the contraction of the medial aspect of the thigh and movement of the patella. This is used to identify the site of implantation when stimulating the SAFN.

Since the SAFN is purely a sensory nerve, and does not result in muscle-evoked activity, the nerve leading to the vastus medialis muscle runs alongside the SAFN and is used as a landmark to locate the SAFN. Alternative sites for needle insertion have been used on the line of the inguinal fold (e.g., Bouaziz H, Narchi P, Zetlaoui P J, Paqueron X, Benhamou D: Lateral approach to the sciatic nerve at the popliteal fossa combined with saphenous nerve block. Tech Reg Anesth Pain Manag 1999; 3:19-22, incorporated by reference). Implanting a neurostimulator/electrode using a transsartorial approach or at the medial femoral condyle location are also possible, but may be inferior due to increased movement/muscle in that area and increased risk of electrode migration. Not to be limited by theory, a below-the-knee implant may be preferable due to less muscle and easier access/identification of the SAFN.

In an embodiment, in step 678, sensed activity such as bladder activity is assessed in response to stimulation of different stimulation sites along the SAFN pathway. Site assessment can include measuring at least one of stimulation and post-stimulation changes in bladder activity/pressure, subjective, evoked neve activity or other measures. When assessing two or more candidate areas for implantation, a percutaneous electrode may be used to assess at least one of: a) nerve recruitment sensation threshold (e.g., choose site with lowest threshold), b) pain threshold (e.g., choose site with highest threshold, or largest difference between nerve recruitment and pain threshold), c) chose site with largest difference between recruitment and pain threshold, d) electrophysiological responses which occur rostral or distal to stimulation site (e.g., choose site with largest evoked response to a given stimulus, or with evoked response at lowest amplitude of stimulation signal), or a combination thereof. Assessment includes evaluating candidate sites and stimulation parameters for the SAFN or other nerves such as the tibial nerve or PTN, each of which may be used alone or in combination during treatment. In an embodiment, two nerves are assessed during combination stimulation. When a candidate implantation site is near the inguinal crease it can be assessed/confirmed by sensing evoked potentials at the SAFN or PTN at more distal locations between the knee and the malleolus. Although harder to access, at higher (rostral)

locations within the leg or pelvic area, the target nerve will be larger in diameter and thereby (contain a greater number of SAFN nerve fibers), and resultant modulation of bladder activity can be greater.

Stimulation of nerves related to the lumbar plexus, with a focus on the sensory fibers, may provide relief of OAB symptoms and or other pelvic floor disorders. Stimulation of the Iliohypogastric Nerve has been disclosed as treating painful bladder syndrome (e.g. U.S. Pat. No. 8,417,346), but has not been suggested for treating overactive bladder. The iliohypogastric nerve runs anterior to the psoas major on its proximal lateral border to run laterally and obliquely on the anterior side of quadratus lumborum. Lateral to this muscle, it pierces the transversus abdominis to run above the iliac crest between that muscle and abdominal internal oblique. It gives off several motor branches to these muscles and a sensory branch to the skin of the lateral hip. Its terminal branch then runs parallel to the inguinal ligament to exit the aponeurosis of the abdominal external oblique above the external inguinal ring where it supplies the skin above the inguinal ligament (i.e. the hypogastric region) with the anterior cutaneous branch. This may be most appropriate for modulation by an implantable neurostimulator near the inguinal ligament.

Alternative targets for treatment of OAB, or other pelvic floor disorders, are the Ilioinguinal nerve and the genitofemoral nerve, the lateral cutaneous femoral nerve, the obturator nerve notably its anterior branch contributes a terminal, sensory branch which passes along the anterior border of gracilis and supplies the skin on the medial, distal part of the thigh. The superior cluneal nerves which innervate the skin of the upper part of the buttocks, and are the terminal ends of lateral rami of the posterior rami, may also serve as targets for modulating OAB via their lumbar roots (L1, 2, 3) and/or participation in associated circuits that modulate central structures. These nerve targets have been stimulated to treat post-surgical hernia complications and lower back neuralgia, but not for treatment of OAB.

Identification of peripheral nerves such as the SAFN or PTN can be assisted by imaging methods such as, MRI or ultrasound. Alternatively, observation can also be used such as looking for foot twitch (evoked motor response), or sensing EMG activity, in the case of tibial or PTN stimulation. The EMG evaluation may involve examining time locked or evoked responses to the stimulation. F-waves can be evoked by a strong electrical stimulus which provides supramaximal stimulation to the skin surface above a distal segment of a nerve. The evoked impulse typically travels both distally (towards the muscle fiber, orthodromic) and proximally or distally (back to the associated motor neurons of the spinal cord, antidromic). When the orthodromic response reaches the muscle fiber, it elicits a strong M-response which reflects a muscle contraction. Antidromic stimulus reaches the motor neuron cell bodies, and then a smaller portion of the motor neurons backfire to produce an orthodromic wave that travels back down the nerve to the muscle. This "reflected" response evokes small proportion of the muscle fibers causing a small, second compound muscle action potential (CMAP) called the F-wave. Both M-wave and F-wave responses are among the evoked motor activity that can be measured in response to the PTN stimulation. While the SAFN does not provide the same notable muscle response, smaller evoked responses may be sensed by providing pulsed stimulation at a candidate stimulation site such as immediately above or below the knee and recording evoked activity from, for example, immediately proximal to the medial malleolus or the arch of the foot. The evoked neural activity can be measured with a surface electrode or a needle electrode positioned in close proximity to the SAFN or its branches. Somatosensory evoked responses or sensory nerve action potentials (SNAP) can also be used to detect successful stimulation of the SAFN, and typically electrodes are located over the sacrolumbar area to record responses to stimulation applied the lower limbs. The area just above the patella or the popliteal fossa (sometimes referred to as the "knee-pit") is a shallow depression located at the back of the knee joint and may also be used as a site to record averaged, SNAPs evoked by SAFN/TPN stimulation lower in the leg.

The feasibility of confirming electrical activation of the SAFN may be further tested in patients (i.e., screening test) by measuring the mechanical sensitivity of the skin innervated by SAFN fibers. The test would assess the patient's sensitivity to variables such as temperature and touch (e.g., 2-point discrimination test) and thereby predict appropriate stimulation parameters aimed at maximizing the clinical effects of SAFN stimulation.

Once a site is selected, it can be confirmed/assessed in a number of manners. For example, an evaluation signal which oscillates above and below the user's recruitment threshold may be used and the patient is asked about evoked sensation and paresthesia in an expected area of the body.

Stimulation Parameters, Protocols, and Signals

Using TENS to treat disorders can be problematic for users who experience cutaneous pain. This can occur during SAFN or PTN stimulation for treatment of OAB. Pain may limit the amplitude used during therapy leading to decreased benefit and can decrease compliance. High frequency stimulation signals or use of paired-pulse signals may decrease unwanted side-effects from co-activation of motor or pain fibers (e.g. see US Pub Nos. 20130090712 Functional Electrical stimulation device and system and use thereof, and 20160051817 Electrical Stimulation System with Pulse Control; U.S. Pat. No. 5,052,391 High frequency high intensity transcutaneous electrical nerve stimulator and method of treatment; U.S. Pat. No. 6,445,955 Miniature wireless transcutaneous electrical neuro or muscular-stimulation unit; US Pub No. 20120029591 Devices and methods for non-invasive capacitive electrical stimulation and their use for vagus nerve stimulation on the neck of a patient, all incorporated by reference here in). High frequency stimulation can cause earlier onset of muscle fatigue and may affect walking or leg movement/control.

As will be recognized by a person of skill in the art, characteristics of electrical pulse, including, without limitation, amplitude (pulse strength, referring to the magnitude or size of a signal voltage or current), type of power source (voltage or current), pulse duration, frequency, polarity, phase, relative timing and symmetry of positive and negative pulses in biphasic stimulation, and/or wave shape (e.g., square, sine, triangle, or variations or combinations thereof) may be varied to optimize results in any particular treatment, user, or class of users. Further bursts of high frequency pulses can be modulated at lower repetition rates (e.g. 50 kHz modulated or repeated at 20 Hz). For example, stimulation envelopes may range from approximately 0.5 Hz to approximately 500 Hz, although for treatment of OAB, typically 1-100 Hz is used, and 5-20 Hz is preferred, e.g., (5 Hz, 0.2 ms pulse width). In embodiments, pulse widths may vary from 0.01 to 3.0 msec.

The neurostimulation pulse may by monophasic, biphasic, and/or multi-phasic. In the case of the biphasic or multi-phasic pulse, the pulse may be symmetrical or asymmetrical. Its shape may be rectangular, exponential, or a combination of the two waveforms. In an embodiment, the stimulation waveform can be cathodic stimulation (although anodic is viable), biphasic, and asymmetrical. Pulses may be applied in continuous or intermittent trains (i.e., the stimulus frequency changes as a function of time). In the case of intermittent pulses, the on/off duty cycle of pulses may be symmetrical or asymmetrical, and the duty cycle may be regular and repeatable from one intermittent burst to the next or the duty cycle of each set of bursts may vary. Varying the stimulus frequency and/or duty cycle may decrease risk of habituation.

In embodiments, a range of from 1 to 20 V is used for TENS stimulation of peripheral nerves. When stimulating the PTN, the voltage used for foot stimulation is selected to be from 2 to 6 times the toe twitch motility threshold (2 T-6 T), seen as twitching or fanning of toes. In the case of the SAFN there is no direct motor evoked response. Stimulation strength may range between 2-3 times sensation threshold, and less than the level that causes pain. Current may be provided, for example, in a range of 5 mA to 60 mA. Biphasic paired stimuli are preferred, with the assumption being two or more pulses are of opposite polarity and substantially equal net charge (e.g., charge balanced) or asymmetrical. When two electrodes are used the proximal may be cathode and the distal is anode. However, the opposite stimulation montage may be set if this is found to provide increased comfort, or other advantage, to the user.

Biological systems typically do not use chronic signals and display variability. Not to be limited by theory, using a continuous stimulation may be less effective than stimulation that varies with respect to, for example duration and strength of pulses or stimulation windows. The stimulus may be applied intermittently e.g., a short (10 seconds) ON and 50 seconds OFF across a 30 minute interval. Roving of modulation rate within a range may also provide larger clinical effects than a non-changing (stationary) stimulation pattern.

Stimulation parameters can also include the stimulation pulse shape, amplitude, duration, pattern, bursting or tonic mode, and frequency. Increasing pulse amplitude or duration, or both, can provide increased pulse intensity or “strength”/“dosage” of the TENS therapy. With larger stimulation signals, issues related to electrode polarity and charge balancing may increase. Biphasic stimulation will typically decrease the risk for a concentration of ions building an alkaline or acid reaction under the skin of the anode and cathode, respectfully. Using charged balanced waveform, with a very short delay between positive and negative pulses, may be preferable as is well known.

In an embodiment, the TENS device or implanted device is configured to electrically stimulate nerves using asymmetric biphasic electrical pulses, a signal generator generates a voltage at an anode that is higher than a voltage at a cathode to bias current flow from the anode to cathode, wherein during each phase of the asymmetric biphasic electrical pulses, and wherein said signals deliver a larger amount of electrical charge in the second phase of the asymmetric biphasic electrical pulse than the amount of electrical charge delivered in the first phase while using the same anode voltage setting in both phases (using the electrical charge accumulated during the first phase).

Stimulation and Modulation for Normalization.

The system **8*b*** components and methods are effective to inhibit or excite bladder contractions and are expected to affect urological conditions including: OAB symptoms including bladder (detrusor) overactivity, urinary frequency/urgency, urinary incontinence (including bedwetting), interstitial cystitis (IC), urinary retention, and pelvic pain. Stimulation can provide modulation of gastrointestinal conditions, such as fecal incontinence, irritable bowel syndrome (IBS), and constipation and/or rectal contractions/activity. Stimulation can modulate the spinal, central, somatic, and autonomic nervous system. Not to be limited by theory, stimulation may provide a resetting or balance between excitatory and inhibitory neural circuits. For example, if the bladder is overactive, then stimulation will cause the CNS to inhibit bladder activity, while in the case of a person suffering from bladder retention, stimulation may cause the CNS (or other component of the pathways being modulated) to be more excitatory to the bladder to increase contraction or otherwise facilitate voiding. The stimulation to produce an opposite effect typically occurs at different intensities, frequencies, or durations, but may be the same. Since the bladder is an autonomic organ, modulation of OAB symptoms suggests that stimulation of peripheral targets in the leg (e.g. SAFN) may also modulate other autonomic organs.

While the SAFN is a primary target for modulation of OAB, other nerves can be stimulated to treat OAB or other indications including at least a portion of the superficial peroneal nerve and branches thereof (e.g. dorsal intermediate and dorsal medial cutaneous nerves), deep peroneal nerve, pudendal nerve, hypogastric nerve, pelvic nerve, sural nerve, and/or tibial nerve of a user. While most of the embodiments disclose stimulating the SAFN between the foot and the knee, superior locations are also within the scope of the invention, some of which will be disclosed.

The device 12 may be programmable, pre-programmed, non-programmable, or otherwise adapted to or configured to provide stimulation. In addition to the device being adjustable by a user, it can have multiple stored programs related to providing relief from various symptoms or disorders (pain, OAB, constipation). Limits which are defined for particular therapies and the type of user interaction and tracking can be defined differently for different treatments. For example, the survey questions presented to a user in the treatment of pain will be different than those used for treatment of OAB.

Combination Drug and Device Treatment and Trials.

Treatment can combine electrical stimulation with treatment using medication such as anti-OAB drugs to improve the size or prevalence of the treatment response or to lower the amount of drug relied upon (and potential resulting side-effects). The combination of stimulation and drug therapy can improve the number of responders to a drug when provide concomitantly. In an embodiment, stimulation of the SAFN is used in combination with a drug during an FDA trial and compared to the drug alone, drug at a different dose, or to a control group which is either sham or alternative therapy to show the benefit of SAFN in combination with the drug, compared to drug alone. The explored benefits may relate to dose, dose dependency, efficacy, and/or side effects. The trial may only have one group and may compare its results to other trials that assess drug or other intervention. The drug trial may be double-blind, single-blind, or un-blinded and may be a randomized clinical trial with appropriately matched cohorts. The drug trail may be related to treatment of OAB, or other urological/gastrointestinal disorder, pelvic floor or other disorder. The drug may be, for example, one of, or a combination of, a serotonin/norepinephrine reuptake inhibitor and/or a serotonin/norepinephrine receptor ($5HT_{1A}$) antagonist blocker and/or anti-muscarinic compound and/or opioid compound. Rather than drug, the use of SAFN stimulation may be evaluated in combination with other interventions provided by other medical devices or procedures.

In an embodiment, a method of treating a disorder of a lower urinary tract in a user comprises: positioning a device upon the skin surface of the user; generating one or more electrical impulses with the device; using electrodes to transmit the one or more electrical impulses transcutaneously from the device to SAFN fibers within the user; and wherein the one or more electrical impulses comprises one or more bursts of pulses sufficient to cause the SAFN fibers to generate one or more action potentials that at least partially relieve a symptom selected from a group of symptoms comprising urgent urination, frequency urination, urge incontinence, nocturia, ischuria, bladder discomfort and bladder pain.

Treatment and Modulation of Patient States and Conditions.

A central focus of this disclosure is the stimulation of the SAFN that can be provided to at least partially relieve a symptom selected from a group of symptoms comprising urinary urgency, urinary frequency, urge incontinence, mixed incontinence, enuresis, nocturia, ischuria, bladder discomfort, and bladder pain. The stimulation of the SAFN can also be done to treat dyslipidemia, obesity, and eating disorders. The stimulation may occur once a week, every day, multiple times per day, or in response to user request or sensed data.

The TENS or implantable stimulators disclosed herein can be considered electroacupuncture devices and can be used to treat disorders which have been treated by acupuncture at the same sites. For example, when implanted the device 600 can be insert to stimulate acupuncture points. For example, SP8, SP9 and/or LIV 6 is stimulated to provide stimulation at these points and/or the SAFN in OAB treatment.

Additionally, the systems and methods disclosed herein can be applied to treat a variety of disorders and conditions. For each condition, the stimulation parameters, survey questions, treatment schedules and other components of the treatment regimen may be adjusted to derive the desired results.

In an embodiment, when used to provide vagal nerve modulation, the system may be adapted as disclosed in US App No. 20120035680 entitled Systems and Methods for Respiratory-Gated Auricular Vagal Afferent Nerve Stimulation, and the stimulation is provided to the auricular area. Survey questions, sensed data, and treatment criteria may be related to assessment of pain, inflammation, or other disorder.

In an embodiment, when used to provide vagal nerve modulation, the system may be adapted as disclosed in US App No. 20140324118 entitled Devices and methods for treating medical disorders with evoked potentials and vagus nerve stimulation, and the stimulation is provided to the neck area. Survey questions sensed data, and treatment criteria may be related to assessment of migraine or other primary headaches, or fibromyalgia, or other disorder.

In an embodiment, when used to provide cardiovascular modulation, the system may be adapted as disclosed in U.S. Pat. No. 7,797,041 entitled Transcutaneous neurostimulator for modulating cardiovascular function, and the stimulation is provided to the neck area. Survey questions sensed data, and treatment criteria may be related to assessment of blood pressure, cardiovascular measures, or various disorders.

In an embodiment, when used to provide transcranial stimulation, the system may be adapted as disclosed in US App. No. 20160022981 entitled Electrode system for electrical stimulation, and the stimulation is provided to the head area. Survey questions sensed data, and treatment criteria may be related to assessment of cognitive state, cognitive performance, stroke, or other disorder.

In an embodiment, when used to provide stimulation for pain, the system may be adapted as disclosed in US App. No. 20180140834 entitled Transcutaneous electrical nerve stimulator with user gesture detector and electrode-skin contact detector, with transient motion detector for increasing the accuracy of the same, and the stimulation is provided to the leg. Survey questions sensed data, and treatment criteria may be related to assessment of pain, sleep, restless leg disorders, or other disorder.

In an embodiment, when used to provide stimulation for OAB or incontinence using either electrical or magnetic stimulation, the system may be adapted as disclosed in US App. No. 20160045731 entitled Non-Invasive electrical and magnetic nerve stimulators used to treat overactive bladder and urinary incontinence, and the stimulation is provided to the leg. Survey questions sensed data, and treatment criteria may be related to assessment of OAB, a pelvic floor disorder, or other disorder.

In embodiments, the system can be applied to provide treatment of, or modulation of, a psychiatric disorder such as anxiety, a cognitive disorder, stroke, performance, sleep or a sleep disorder, movement disorders or tremor, a cardiac condition, high or low blood pressure, dysmenorrhea, weight loss, obesity, a metabolic disorder, appetite, smoking, addiction, etc. The frequency and content of the survey items, and the stimulation related induction and maintenance schedules, are adjusted to be appropriate for the disorder or condition which is expected to change due to stimulation.

The above cited patents, patent applications, and references cited in this Specification are all incorporated by reference.

In this application, section titles are used for convenience only and do not limit the invention in any manner.

Although the disclosure is sufficiently detailed to enable those skilled in the art to practice the invention, the embodiments disclosed serve to exemplify the invention which may be otherwise embodied and the details may be changed without departing from the invention. Any elements described as singular can be pluralized (i.e., anything described as "one" can be more than one). The described configurations, elements and methods and their steps for carrying out the invention, and variations of aspects of the invention can be combined, and modified with each other, in any combination.

Additional changes in the details, materials, steps and arrangements of parts, which have been herein described and illustrated to explain the nature of the present invention, may be made by those skilled in the art while still remaining within the principles and scope of the invention.

Steps of the methods may be implemented in the order shown in the figures or may occur in different orders, may be omitted, or repeated. Steps from one method may be combined with steps from other methods as disclosed herein.

What is claimed is:

1. A method of improving symptoms related to nocturia in a person, the method comprising:

determining that a person suffering from nocturia has transitioned to a sleeping interval during which the person is likely to be in a sleep state, using at least one of time data and actigraphy data, said sleeping interval during which stimulation is governed by a sleep stimulation protocol;

establishing at least one sensor for sensing a set of sensed data at least during said sleeping interval;

establishing an electrical generator coupled to a neurostimulator;

providing a user device configured for communicating with said neurostimulator and accepting user input data at least after said sleep time interval;

operating at least one processor for receiving the set of sensed data, said at least one processor having further data defining a sleep stimulation protocol;

determining by said set of sensed data in accordance with said sleep stimulation protocol that a trigger event defining a nocturia condition has occurred related to said nocturia;

adjusting said sleep stimulation protocol and a resulting therapy regimen in response to the trigger event;

establishing a control module having a therapy regimen adapted to provide electrical or magnetic stimulation according to said sleep stimulation protocol to a nerve in the leg of said person at a location between an ankle and a knee of the person, the control module is further adapted to cause a monitoring module to analyze, using the at least one processor, at least one of said set of sensed data and said user input data in accordance with said therapy regimen and said sleep stimulation protocol to detect and log trigger events, wherein the trigger events include candidate bathroom events defined as out-of-bed events based on sensed data indicative of walking that occurred at least during said sleeping interval; and, presenting on said user device data of a log of stored candidate events and obtaining retrospective confirmation of out-of-bed events at least during at a time that is subsequent to said sleeping interval as bathroom voiding events to classify the number of out-of-bed events that were bathroom events, said time being an awake interval during which the person is likely to be in an awake state, using at least one of time data and actigraphy data.

2. The method of claim 1, wherein the determining the person suffering from nocturia is sleeping is selected from the group of at least one of: (1) assessing a clock time is within a defined sleep interval, (2) assessing a clock time is within a selected number of minutes of a time defined for a person to wake up, (3) assessing activity level of the person to be below a selected threshold, and (4) assessing a body position of said person as not-standing up.

3. The method of claim 1, wherein the trigger event is determined by detecting an urge to urinate by evaluation of said set of sensed data.

4. The method of claim 3, wherein the urge to urinate is assessed using said set of sensed data related to at least one bladder measurement.

5. The method of claim 3, wherein the urge to urinate is assessed using said set of sensed data related to a biometric measurement.

6. The method of claim 3, wherein the trigger event is assessed by evaluating electromyography (EMG) or accelerometer data related to leg activity.

7. The method of claim 1, wherein the trigger event is determining that a clock time value has occurred in relation to a time defined for when the person is scheduled to awake.

8. The method of claim 1, further comprising determining a sleep cycle of the patient and contingently adjusting the stimulation protocol based upon the sleep stage of the person.

9. The method of claim 1, wherein the providing of electrical or magnetic stimulation to the nerve of the person is automatically provided in response to a signal from bladder monitoring.

10. The method of claim 1, wherein the stimulation is defined to begin only after a time delay from a time of said determination that said person is sleeping and uses a gradually increasing stimulation amplitude, whereby stimulation is less likely to interfere with the onset of sleep.

11. The method of claim 1, wherein adjusting therapy in response to the trigger event includes increasing the voltage or current amplitude of said stimulation whereby improved acute inhibition of bladder activity is provided.

12. The method of claim 1, wherein the electrical or magnetic stimulation is provided to a saphenous nerve of the person.

13. The method of claim 1, wherein adjusting therapy in response to the trigger event includes pausing stimulation for a specified amount of time.

14. The method of claim 1, wherein the electrical or magnetic stimulation is provided by the neurostimulator that is a wearable neurostimulator configured with a set of electrodes displaced each from the other in a vertical direction to provide an electrical path therebetween.

15. The method of claim 1, wherein the therapy regimen further includes tracking of nocturia using data from the at least one sensor and the monitoring module configured to detect and log candidate bathroom events which are potential nocturia events which after confirmation are counted and tracked over time.

16. The method of claim 1, wherein a treatment protocol of said therapy regimen further includes operating the user device for interacting with the person to confirm at least one detected candidate bathroom event.

17. The method of claim 1, wherein a treatment protocol of said therapy regimen further includes operating the user device for interacting with the person to provide a score for urgency of at least one detected candidate bathroom event confirmed by the user operating the user device.

18. The method of claim 1, wherein the therapy regimen further includes providing the person with a scheduled behavioral coaching session including messages or reminders about behavior using a software application that is adapted to operate as a module of a software application of the user device which is designed to provide an ecosystem for a neurostimulation treatment.

19. The method of claim 1, wherein providing the therapy regimen adapted to provide electrical or magnetic stimulation according to said sleep stimulation protocol further includes providing stimulation intermittently throughout the night.

20. The method of claim 1, wherein the therapy regimen is further adapted to obtain confirmation of the number of voiding events by operating a survey module to present information to said person using said user device about detected out-of-bed events which are candidate bathroom events and to prompt the person to confirm the number of the out-of-bed events which should be correctly counted as voiding events.

21. The method of claim 20, wherein the user is prompted by the user device to provide information on urgency for out-of-bed events that are confirmed as voiding events.

22. The method of claim 20, wherein the user is prompted to provide information on incontinence for out-of-bed events that are confirmed as voiding events.

23. The method of claim 1, further including operating an accessory module configured to automatically log out-of-bed events including bathroom visits if the neurostimulator is in range of a “ping” signal provided by internet-of-things technology and according to protocols for achieving presence or proximity detection between two objects.

24. The method of claim 1, wherein at least one processor is configured to operate to assess and report sleep-related measures including sleep quality or sleep duration.

25. The method of claim 1, wherein said candidate bathroom events are included in data presented to a user on the user device for confirmation by the user.

26. The method of claim 1, further including adjusting said therapy regimen for operation of said processor subsequent to said trigger event being detected based upon said set of sensed data and additional user input data responsive to a query notification presented to the user on the user device of said trigger event being detected.

27. The method of claim 1, wherein said sleep stimulation protocol uses a lower intensity of stimulus than that used during the awake stimulation protocol.

28. The method of claim 1, wherein said sensed data are at least one of accelerometer data and EMG data which are used to detect potential walking events.

* * * * *